United States Patent
Shah et al.

(10) Patent No.: US 10,960,001 B2
(45) Date of Patent: Mar. 30, 2021

(54) OPIOID AGONIST / ANTAGONIST COMBINATION DOSAGE FORMS

(71) Applicant: KASHIV PHARMA LLC, Bridgewater, NJ (US)

(72) Inventors: Navnit H. Shah, Bridgewater, NJ (US); Wantanee Phuapradit, Montville, NJ (US); Dipen Desai, Whippany, NJ (US); Harpreet Kaur Sandhu, West Orange, NJ (US); Siva Ram Kiran Vaka, Piscataway, NJ (US); Chanchal Patel, Monmouth Junction, NJ (US); Roshan V. Tiwari, Hillsborough, NJ (US); Atsawin Thongsukmak, Piscataway, NJ (US)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 0 days.

(21) Appl. No.: 16/477,268

(22) PCT Filed: Jan. 12, 2018

(86) PCT No.: PCT/US2018/013601
§ 371 (c)(1),
(2) Date: Jul. 11, 2019

(87) PCT Pub. No.: WO2018/132725
PCT Pub. Date: Jul. 19, 2018

(65) Prior Publication Data
US 2019/0358221 A1    Nov. 28, 2019

Related U.S. Application Data

(60) Provisional application No. 62/446,240, filed on Jan. 13, 2017, provisional application No. 62/509,683, filed on May 22, 2017.

(51) Int. Cl.
| | | |
|---|---|---|
| *A61K 31/485* | (2006.01) | |
| *A61K 9/00* | (2006.01) | |
| *A61K 9/16* | (2006.01) | |
| *A61K 47/32* | (2006.01) | |
| *A61K 47/38* | (2006.01) | |

(52) U.S. Cl.
CPC .......... *A61K 31/485* (2013.01); *A61K 9/0053* (2013.01); *A61K 9/167* (2013.01); *A61K 47/32* (2013.01); *A61K 47/38* (2013.01)

(58) Field of Classification Search
None
See application file for complete search history.

(56) References Cited

U.S. PATENT DOCUMENTS 9,351,517 B2    5/2016    Bromley

FOREIGN PATENT DOCUMENTS

| EP | 1 897 544 A1 | 3/2008 | |
|---|---|---|---|
| EP | 1897544 A1 * | 3/2008 | ........... A61K 9/1652 |
| WO | WO 2005/097075 A2 | 10/2005 | |
| WO | WO-2005097075 A2 * | 10/2005 | ............ A61K 36/47 |
| WO | WO 2015/120201 A1 | 8/2015 | |
| WO | WO-2015120201 A1 * | 8/2015 | ............... A61K 9/48 |

OTHER PUBLICATIONS

Burris et al., "Legal Aspects of Providing Naloxone to Heroin Users in the United States," Int J Drug Policy 12:237-248 (2001).
Davis et al., "Expanded Access to Naloxone Among Firefighters, Police Officers, and Emergency Medical Technicians in Massachusetts," Am J Public Health. 104(8):e7-e9 (2014).
Evonik Industries: "Eudragit", Dec. 1, 2015 (Dec. 1, 2015), XP55288214, Retrieved from the Internet: URL:http://eudragit.evonik.com/sites/lists/HN/Documents/evonik-brochure-eudragit-EN.pdf [retrieved on Jul. 13, 2016] p. 14.
Hawk et al., "Reducing Fatal Opioid Overdose: Prevention, Treatment and Harm Reduction Strategies," Yale J Biol Med. 88:235-245 (2015).
International Search Report dated Mar. 28, 2018 in International Application No. PCT/US2018/013601.
Ngai et al., "Pharmacokinetics of Naloxone in Rats and in Man: Basis for its Potency and Short Duration of Action," Anesthesiology 44(5):398-401 (1976).
Robinson et al., "Intranasal naloxone administration for treatment of opioid overdose," Am J Health Syst Pharm. 71:2129-2135 (2014).
Wermeling et al., "A Response to the Opioid Overdose Epidemic: Naloxone Nasal Spray," Drug Delivery Transl. Res. 3:63-74 (2013).
Wermeling, "Review of naloxone safety for opioid overdose: practical considerations for new technology and expanded public access," Ther Adv Drug Safety 6(1):20-31 (2015).

* cited by examiner

*Primary Examiner* — Jake M Vu
(74) *Attorney, Agent, or Firm* — Kashiv BioSciences, LLC; Vandana Awasthi

(57) ABSTRACT

The presently disclosed subject matter provides a solid, immediate release, pharmaceutical multi-particulate dosage form containing at least one population of Opioid Particulates comprising one or more opioids; at least one population of Naloxone Particulates; and a population of Triggering Particulates. Each population of particulates is designed for a specific function to accomplish the desired combination of abuse deterrence and overdose protection.

6 Claims, No Drawings

OPIOID AGONIST / ANTAGONIST COMBINATION DOSAGE FORMS

CROSS-REFERENCE TO RELATED APPLICATION

This application is a U.S. National Stage Patent Application under 35 U.S.C. § 371 of International Application No. PCT/US2018/013601, filed on Jan. 12, 2018, which claims priority to U.S. Application Ser. No. 62/446,240, filed Jan. 13, 2017, and U.S. Application Ser. No. 62/509,683, filed May 22, 2017, the content and disclosures of which are herein incorporated by reference in their entireties.

FIELD

The presently disclosed subject matter relates to immediate release opioid agonist-antagonist combination dosage forms with abuse deterrent (AD) and overdose protection (ODP) properties/features, and processes of manufacture. In certain embodiments, the multiparticulate dosage forms comprise Opioid Particulates and Naloxone Particulates. In certain embodiments, Naloxone Particulates are enteric coated to enhance oral bioavailability of naloxone by saturating first-pass metabolism. In certain embodiments, oral bioavailability of naloxone is enhanced by improving naloxone solubility and avoiding first-pass metabolism of naloxone. In certain embodiments, Naloxone Particulates contain lipid-based naloxone compositions, or amorphous solid dispersions (ASDs) of naloxone, to avoid first-pass metabolism of naloxone, enhance naloxone solubility, and improve oral bioavailability of naloxone.

BACKGROUND

Drug overdose is the leading cause of accidental death in the U.S. and is a global public health issue (Wermeling et al. (2013) Drug Delivery Transl. Res. 3:63-74). Fatalities from opioid overdose have been increasing steadily over recent years. The majority of drug overdose deaths are unintentional or accidental (74.3%). Among opioid dosage forms, immediate release oxycodone is one of the drugs most prone to overdose.

Drug abuse often involves some physical or mechanical manipulation of a dosage form so that a large amount of immediately available drug can be taken orally, nasally, or by intravenous injection. Further, there are reports of people deliberately or mistakenly swallowing a number of intact dosage units despite instructions not to do so, and suffering serious adverse effects. Hence, there is a need for abuse deterrent opioid dosage forms that can also prevent, inhibit, or delay the adverse effects of an overdose caused by ingesting multiple units of the dosage form, either intentionally or unintentionally.

The U.S. Food and Drug Administration (FDA) describes the science of abuse deterrence as relatively new and rapidly evolving. The need remains for improved formulations that make it difficult, if not impossible, for individuals to abuse or misuse opioids, not only by crushing, grinding, cutting, chewing, snorting and/or extraction of drug, but also by ingesting multiple doses. In particular, new/improved immediate release pharmaceutical formulations and dosage forms are needed to prevent, inhibit, reduce, or delay the effects of overdose by ingesting multiple units of the dosage form, either intentionally or unintentionally. Such formulations should combine overdose protection and abuse deterrence in a single dosage form and thereby address multiple health-related concerns, especially regarding habit-forming opioid compounds, for which there is a high propensity for abuse and overdose. These dosage forms must also allow the opioid pharmaceutical ingredient to be soluble and absorbable in the gastrointestinal tract and have the desired pharmacological activity when ingested as directed. In the case of opioids, the pharmacological activity would be, for example, an analgesic effect.

There have previously been attempts in the art to control the abuse potential associated with opioid analgesics in an oral opioid dosage form, such as those that require the inclusion of an opioid antagonist that is not orally active but substantially blocks the euphoric (and analgesic) effect of the opioid if one attempts to dissolve the opioid and administer it parenterally. Prescription opioids (e.g., oxycodone, hydrocodone, oxymorphone, hydromorphone, codeine, fentanyl, and morphine) and heroin are opioid receptor agonists. They can effectively modify the perception of pain pathways within the brain and spinal cord. With larger doses, respiratory depression can occur, limiting adequate oxygenation of blood, which reduces oxygen availability to the brain and heart, leading to unresponsiveness, anoxia, cyanosis, and death. This respiratory depression is reversible until death occurs; for example, it can be reversed with a pharmacological antidote, e.g., naloxone. Naloxone displaces opioids from the opioid receptors and blocks the binding of opioids for 20-90 minutes (Hawk et al., 2015).

Naloxone has been used for in-hospital opioid reversal for more than 40 years, and although rare side effects have been reported, it has an excellent safety profile (Burris et al., 2001; Davis et al., 2014). Naloxone is readily transported across the blood-brain barrier and has a fast onset of action in reversing the effects of opioids (Nagi et al., 1976). As naloxone is devoid of agonistic activity at the µ-opioid receptor, it is generally regarded as a safe drug.

Naloxone appears to be reasonably well absorbed after oral administration, but its low bioavailability renders naloxone less suitable for this route of administration. Following oral administration, naloxone undergoes extensive hepatic metabolism, indicating high first-pass metabolism greater than about 95%). The elimination half-life of naloxone in plasma is approximately 30 minutes. Naloxone was first approved in the U.S. in 1971 (NARCAN® injection) as a sterile solution for intravenous (IV), intramuscular (IM), and subcutaneous (SC) administration. In November 2015, NARCAN® Nasal Spray (Adapt Pharma) became the first FDA approved noninjectable naloxone product for the treatment of opioid overdose. The safety profile of intranasal naloxone is comparable that of naloxone injection in the treatment of opioid overdose (Robinson and Wermeling, 2014). The opioid epidemic, along with the risk of blood-borne infections, reinforces the need for further alternative (noninjectable) routes of naloxone administration for the treatment of patients with suspected opioid overdose in the out-of-hospital setting. Even though intranasal administration would be the preferred route for a person unresponsive due to an opioid overdose, in some circumstances this route can be less than optimal.

There is an unmet medical need for user-friendly, needle-free, naloxone delivery systems for medical professionals, first-responders, and at-home family members (Wermeling 2015). There is an unmet need for oral dosage forms containing an opioid combined with an opioid antagonist (e.g., naloxone) that can prevent, inhibit, reduce, or delay the effects of an opioid overdose without any additional assistance required. Furthermore, there is an unmet need for oral opioid dosage forms that can prevent intentional or unintentional opioid overdose by releasing a therapeutically effective amount of naloxone in the event of overdose.

As discussed above, orally administered naloxone exhibits low bioavailability due to its degradation by first-pass metabolism in the liver. After oral administration, drugs pass through the small intestine and enter the portal vein or intestinal lymphatic system. As naloxone undergoes extensive first-pass metabolism, the lymphatic system is a preferred route of transport for naloxone. Naloxone free base has a poor solubility in water of about 1.4 mg/mL at 25° C. It is highly lipophilic and readily transported across the blood-brain barrier and, therefore, has a fast onset of action in reversing or blocking opioid effects and opioid agonist activity. The low solubility of naloxone leads to low dissolution and incomplete absorption, which results in low oral bioavailability. Additionally, the poor solubility of naloxone results in high inter- and intra-subject variability and lack of dose proportionality.

The present application addresses these issues and unmet needs. In certain embodiments, the lipid-based compositions of naloxone and amorphous solid dispersion compositions of naloxone provide enhanced solubility, absorption, and oral bioavailability. These lipid-based naloxone compositions and amorphous solid dispersions of naloxone are converted to solid intermediates, e.g., granules and pellets, by various techniques and combined with at least one opioid (e.g., Opioid Particulates) in hard gelatin capsules, or compressed into tablets after blending with at least one opioid and any suitable tableting excipients. In certain embodiments, oral, lipid-based naloxone formulations and amorphous solid dispersions (ASDs) of naloxone reduce food-dependent aspects of bioavailability and enhance oral bioavailability of naloxone. Such oral, lipid-based naloxone formulations and ASDs of naloxone can be used in abuse deterrent opioid formulations to provide multidose protection of oral administration of the opioid. In certain embodiments, crystalline solid dispersions of naloxone can be used in an abuse deterrent opioid formulation to provide multidose protection of the opioid.

SUMMARY OF THE INVENTION

The presently disclosed subject matter provides a multi-particulate, solid, oral, immediate release, opioid and naloxone combination dosage form with abuse deterrent and overdose protection properties comprising Opioid Particulates and lipid-based Naloxone Particulates. The Opioid Particulates comprise a therapeutically effective amount of at least one opioid or a pharmaceutically acceptable salt thereof, embedded in a polymer matrix, wherein the individual particulates are coated with an acid labile coat. The lipid-based Naloxone Particulates comprise naloxone or a pharmaceutically acceptable salt, a solid carrier, and at least one lipid. A pharmacologically effective amount of the naloxone is released with the opioid and reduces and/or prevents the effects of the opioid when three or more dosage units are consumed.

In certain embodiments, the opioid in the Opioid Particulates of the multi-particulate, solid, oral, immediate release, opioid and naloxone combination dosage form is oxycodone hydrochloride.

In certain embodiments, the Naloxone Particulates of the multi-particulate, solid, oral, immediate release, opioid and naloxone combination dosage form is naloxone hydrochloride. The Naloxone Particulates can be a lipid solution of naloxone hydrochloride adsorbed onto microcrystalline cellulose.

In certain embodiments, the at least one lipid in the lipid-based Naloxone Particulates of the multi-particulate, solid, oral, immediate release, opioid and naloxone combination dosage form can be one or more of oleic acid, glyceryl caprylate/caprate, propylene glycol monocaprylate, glyceryl monolinoleate, caprylic/capric triglyceride, caprylic/capric mono and diglyceride, polyoxyl castor oil, polyethoxylated castor oil, oleyl alcohol, caprylocaproyl polyoxyl-8-glycerides, glyceryl caprylate/caprate, corn oil, oleoylpolyoxyl-6-glycerides, propylene glycol monolaurate, castor oil, soy oil, soy lecithin, ricinoleic acid, and sesame oil.

In certain embodiments, the multi-particulate, solid, oral, immediate release, opioid and naloxone combination dosage form reduces and/or prevents the effects of the opioid by partially or completely reversing or blocking opioid activity.

In certain embodiments, the Naloxone Particulates in the multi-particulate, solid, oral, immediate release, opioid and naloxone combination dosage form provide enhanced oral bioavailability of naloxone. In certain embodiments, the pharmacologically effective amount of naloxone released from the Naloxone Particulates is independent of fed or fasted state of an individual.

In certain embodiments, the lipid-based Naloxone Particulates enhance the solubility of naloxone. In certain embodiments, the enhanced solubility is an improved solubility of naloxone in a lipid-based composition compared to a composition that is not lipid-based.

In certain embodiments, the Opioid Particulates and/or the Naloxone Particulates in the multi-particulate, solid, oral, immediate release, opioid and naloxone combination dosage form comprises an antioxidant. In certain embodiments, the antioxidant can be ascorbic acid and its salts, α-tocopherol, sulfite salts, sodium sulfide, butylated hydroxyanisole, butylated hydroxytoluene, ascorbyl palmitate, or propyl gallate.

In certain embodiments, the Naloxone Particulates in the multi-particulate, solid, oral, immediate release, opioid and naloxone combination dosage form are coated with at least one functional coat layer comprising at least one anionic polymer selected from the group consisting of a copolymer of methacrylic acid and methyl methacrylate (1:1), a copolymer of methacrylic acid and methyl methacrylate (1:2), a copolymer of methacrylic acid and ethyl acrylate (1:1), hydroxypropyl methylcellulose acetate succinate, hydroxypropyl methylcellulose phthalate, cellulose acetate phthalate, crosslinked polyacrylic polymers, and polyvinyl acetate phthalate. In certain embodiments, the anionic polymer is a copolymer of methacrylic acid and methyl methacrylate (1:1).

In certain embodiments, the abuse deterrent characteristics of the multi-particulate, solid, oral, immediate release, opioid and naloxone combination dosage form comprise resistance of the opioid to syringeability and extractability in aqueous and/or hydro-organic solvents.

In certain embodiments, the abuse deterrent characteristics of the multi-particulate, solid, oral, immediate release, opioid and naloxone combination dosage form comprise resistance to crushability and grindability of the Opioid Particulates.

The presently disclosed subject matter also provides a multi-particulate, solid, oral, immediate release, opioid and naloxone combination dosage form with abuse deterrent and overdose protection characteristics comprising Opioid Particulates and lipid-based Naloxone Particulates. The Opioid Particulates comprise a therapeutically effective amount of an opioid or a pharmaceutically acceptable salt embedded in a polymer matrix comprising a high molecular weight polyethylene oxide, wherein individual particulates are coated with an acid labile coat. The lipid-based Naloxone Particulates comprise naloxone or a pharmaceutically acceptable salt thereof, a solid carrier, and at least one lipid. The abuse deterrent characteristics comprise resistance of the opioid to syringeability and extractability in aqueous and/or hydro-organic solvents, and resistance to crushability and grindability of the Opioid Particulates. The overdose protection characteristics comprise releasing a pharmacologically effective amount of naloxone or a pharmaceutically acceptable salt with the opioid or a pharmaceutically acceptable salt and reducing and/or preventing an effect of opioid overdose when three or more dosage units are consumed.

The present disclosure further provides a multi-particulate, solid, oral, immediate release, opioid and naloxone combination dosage form with abuse deterrent and overdose protection characteristics comprising Opioid Particulates and Naloxone Particulates. The Opioid Particulates comprise a therapeutically effective amount of at least one opioid or a pharmaceutically acceptable salt, embedded in a polymer matrix, wherein the individual particulates are coated with an acid labile coat. The Naloxone Particulates comprise an amorphous solid dispersion of naloxone or a pharmaceutically acceptable salt, copovidone, and a solid carrier. A pharmacologically effective amount of the naloxone is released with the opioid and reduces and/or prevents the effects of the opioid when three or more dosage units are consumed. In certain embodiments, the amorphous solid dispersion is coated onto the solid carrier. In certain embodiments, the solid carrier is microcrystalline cellulose pellets. In certain embodiments, the Naloxone Particulates in the multi-particulate, solid, oral, immediate release, opioid and naloxone combination dosage form are coated with at least one anionic polymer based on methacrylic acid and methyl methacrylate.

The present disclosure further provides a multi-particulate, solid, oral, immediate release, opioid and naloxone combination dosage form with abuse deterrent and overdose protection characteristics comprising Opioid Particulates, Triggering Particulates and Naloxone Particulates. The Opioid Particulates in the multi-particulate, solid, oral, immediate release, opioid and naloxone combination dosage form comprise a therapeutically effective amount of at least one opioid or a pharmaceutically acceptable salt, embedded in a polymer matrix, wherein the individual particulates are coated with an acid labile coat. The Triggering Particulates in the multi-particulate, solid, oral, immediate release, opioid and naloxone combination dosage form comprise an alkaline agent. The Naloxone Particulates in the multi-particulate, solid, oral, immediate release, opioid and naloxone combination dosage form comprise naloxone or a pharmaceutically acceptable salt. The Naloxone Particulates in the multi-particulate, solid, oral, immediate release, opioid and naloxone combination dosage form are enteric coated. When three or more units of the multi-particulate, solid, oral, immediate release, opioid and naloxone combination dosage form are consumed together by a subject, a pharmacologically effective amount of naloxone is available from the dosage units to block binding of the opioid to central opioid receptors for about 20 to about 90 minutes.

In certain embodiments, the opioid in the Opioid Particulates of the multi-particulate, solid, oral, immediate release, opioid and naloxone combination dosage form is oxycodone hydrochloride, and the Naloxone Particulates of the dosage form comprise naloxone hydrochloride. In certain embodiments, the pharmacologically effective amount of naloxone hydrochloride comprises a plasma concentration of about 0.7 ng/ml to about 2 ng/ml. In certain embodiments, the pharmacologically effective amount of naloxone hydrochloride comprises a plasma concentration of about 0.88 ng/ml.

In certain embodiments, the ratio of oxycodone hydrochloride to naloxone hydrochloride is in the range of about 4:1 to about 1:4. In certain embodiments, the ratio of oxycodone hydrochloride to naloxone hydrochloride is about 1:2.5.

In certain embodiments, the oxycodone hydrochloride is present in an amount of about 5 mg, about 10 mg, about 15 mg, or about 20 mg, and naloxone hydrochloride is present in an amount of about 4 mg to about 12.5 mg.

In certain embodiments, the enteric coated Naloxone Particulates provide dose-dependent oral bioavailability of naloxone hydrochloride comprising an increase in oral bioavailability of naloxone hydrochloride per dosage unit, when three or more units of the dosage form are consumed together.

In certain embodiments, the opioid is embedded in a polymer matrix comprising a cationic copolymer based on dimethylaminoethyl methacrylate, butyl methacrylate, and methyl methacrylate.

In certain embodiments, the enteric coated Naloxone Particulates comprise an enteric coating of at least one polymer selected from the group consisting of a copolymer of methacrylic acid and methyl methacrylate (1:1), a copolymer of methacrylic acid and methyl methacrylate (1:2), a copolymer of methacrylic acid and ethyl acrylate (1:1), hydroxypropyl methylcellulose acetate succinate, hydroxypropyl methylcellulose phthalate, cellulose acetate phthalate, crosslinked polyacrylic polymers, and polyvinyl acetate phthalate. In certain embodiments, the enteric coating comprises a copolymer based on methacrylic acid and methyl methacrylate (1:1).

In certain embodiments, the naloxone hydrochloride is not co-released with the oxycodone hydrochloride when one or two dosage units are consumed together.

In certain embodiments, the naloxone hydrochloride is co-released with at least a portion of the oxycodone hydrochloride when three or more dosage units are consumed together.

In certain embodiments, the abuse deterrent characteristics of the dosage form comprise resistance to syringeability and extractability of the opioid in aqueous and/or hydro-organic solvents, and resistance to crushability and grindability of the Opioid Particulates.

The presently disclosed subject matter also provides a multi-particulate, solid, oral, immediate release, opioid and naloxone combination dosage form with abuse deterrent and overdose protection characteristics comprising Opioid Particulates, Triggering Particulates, and Naloxone Particulates. The Opioid Particulates in the multi-particulate, solid, oral, immediate release, opioid and naloxone combination dosage form comprise a therapeutically effective amount of at least one opioid or a pharmaceutically acceptable salt, embedded in a polymer matrix, wherein the individual particulates are coated with an acid labile coat. The Triggering Particulates in the multi-particulate, solid, oral, immediate release, opioid and naloxone combination dosage form comprise an alkaline agent. The Naloxone Particulates in the multi-particulate, solid, oral, immediate release, opioid and naloxone combination dosage form comprise naloxone hydrochloride, wherein individual particulates are enteric coated. When three or more dosage units are consumed together by a subject, naloxone hydrochloride is co-released with at least a portion of the opioid, and a pharmacologically effective amount of the naloxone hydrochloride is available to block binding of the opioid to central opioid receptors. In certain embodiments, when three or more dosage units are consumed together, the enteric coated Naloxone Particulates saturate first-pass metabolism in the subject and increase oral bioavailability of naloxone hydrochloride, thereby making available a pharmacologically effective amount of naloxone to block binding of the opioid to central opioid receptors.

DETAILED DESCRIPTION

To date, there remains a need for improved immediate release pharmaceutical dosage forms that make it difficult, if not impossible, for individuals to suffer the consequences of taking the dosage forms in a manner other than intended by the manufacturer. The presently disclosed subject matter provides an abuse deterrent and/or overdose resistant immediate release opioid agonist/antagonist pharmaceutical dosage forms. In certain embodiments, the pharmaceutical dosage form is a single particulate, or a multi-particulate dosage form containing at least one opioid, e.g., oxycodone hydrochloride, and an opioid antagonist, e.g., naloxone hydrochloride.

Naloxone is ineffective at low oral doses. Under normal circumstances, it has little effect when taken by mouth. The presently disclosed subject matter utilizes this principle and provides an opioid agonist/antagonist combination dosage form that contains the opioid antagonist, e.g., naloxone hydrochloride, in an amount such that dosage units as prescribed (e.g., one or two dosage units) provide a low and ineffectual oral dose of the antagonist. However, if an excessive number of dosage units (e.g., three or more dosage units) is consumed, the antagonist will block the opioid effect and, inter alia, prevent, inhibit, reduce, and/or delay the effects of overdose in an individual. Abuse deterrent solid oral dosage forms of the disclosure comprising a combination of opioid and naloxone can be considered a complete treatment program for drug abuse that can prevent, inhibit, reduce, or delay the effects of opioid overdose, e.g., when three or more dosage units are consumed, by (1) pH-triggered modulation of pore formation in the functional coat; and/or (2) providing naloxone in a pharmacologically effective amount to reverse opioid effect. In the latter, naloxone from three or more dosage units, e.g., in an amount that is sufficient to cross blood-brain barrier, displaces opioids from the opioid receptors, and blocks the binding of opioids for 20-90 minutes. In certain embodiments, the opioid/naloxone combination dosage form contains Naloxone Particulates providing enhanced oral bioavailability of naloxone. In certain embodiments, Naloxone Particulates are enteric coated to provide a bolus of naloxone in the intestine, thereby saturating first-pass metabolism and enhancing naloxone oral bioavailability. In certain embodiments, the Naloxone Particulates comprise a lipid-based naloxone composition that bypasses first pass metabolism and enhances naloxone solubility. In certain embodiments, the Naloxone Particulates comprise an amorphous solid dispersion of naloxone that enhances naloxone solubility.

In certain embodiments, the presently disclosed subject matter provides improved solid oral immediate release opioid agonist/antagonist particulate/multi-particulate dosage forms containing at least one population of particulates, e.g., particulates comprising an opioid, or particulates comprising an opioid and an opioid antagonist, e.g., naloxone. In certain embodiments, the presently disclosed subject matter provides improved solid oral immediate release pharmaceutical multi-particulate dosage forms containing at least two populations of particulates, e.g., (1) Opioid Particulates containing an opioid(s) (and, optionally, an opioid antagonist(s)), and (2) Triggering Particulates containing an alkaline agent(s) and/or a pH-stabilizing agent(s). In certain embodiments, the immediate release pharmaceutical multi-particulate dosage forms contain at least three different populations of particulates, e.g., (1) Opioid Particulates containing an opioid(s), (2) Triggering Particulates containing an alkaline agent(s) and/or a pH-stabilizing agent(s), and (3) Naloxone Particulates containing naloxone hydrochloride. In certain embodiments, the immediate release pharmaceutical multi-particulate dosage forms contain at least four, at least five, or at least six different populations of particulates.

In certain embodiments, the presently disclosed subject matter provides an oral immediate release opioid agonist-antagonist combination dosage form comprising one or more opioid agonists and one or more opioid antagonists (e.g., naloxone hydrochloride), wherein the antagonist shows dose-dependent bioavailability. The bioavailability of antagonist increases when multiple units of the opioid agonist-antagonist combination dosage forms are consumed, i.e., bioavailability of the antagonist increases when higher doses (three or more dosage units containing, e.g., about 12.5 mg of naloxone/unit)) are consumed/administered. The nonlinearity is most probably due to saturation of first-pass metabolism at higher plasma antagonist concentration achieved when three or more dosage units are consumed than when two or less dosage units are consumed.

In certain embodiments, the presently disclosed subject matter provides an oral immediate release opioid agonist-antagonist dosage form comprising oxycodone hydrochloride and naloxone hydrochloride in about a 16:1 ratio to about a 1:8 ratio, with oxycodone hydrochloride being present in an amount of about 2.5 mg to about 20 mg and with naloxone hydrochloride being present in an amount of about 1.25 mg to about 20 mg. In certain embodiments, the oxycodone hydrochloride to naloxone hydrochloride ratio is about 16:1, about 8:1, about 4:1, about 3:1, about 2.5:1, about 2:1, about 1.75:1.25, about 1:1, about 1.25:1.75, about 1:2, about 1:2.5, about 1:3, about 1:4, or about 1:8. In certain embodiments, naloxone is present in an amount such that two or less dosage units are not enough to provide pharmacologically y effective amount of naloxone to reverse opioid effects.

In certain embodiments, naloxone does not behave as an antagonist when the dosage form is consumed as intended, e.g., one or two dosage units being consumed. In certain embodiments, naloxone behaves as opioid antagonist when three or more dosage units are consumed. Naloxone provides built-in overdose protection because naloxone is minimally bioavailable, e.g., about 2%, with oral ingestion, and the amount of naloxone present in two or less dosage forms is not enough to provide a pharmacologically effective amount to block and/or reverse an opioid effect.

In certain embodiments, the presently disclosed subject matter provides an oral immediate release opioid agonist-antagonist combination dosage form comprising one or more opioids and naloxone hydrochloride, wherein the naloxone is present at such a level that it will not block the action of the opioid agonist when one or two intact dosage units are consumed. However, there is sufficient naloxone hydrochloride present in the dosage form to block the opioid effect, if three or more dosage units are consumed. Patients who do not abuse their medications or accidentally overmedicate would not experience diminished analgesia and/or opioid withdrawal symptoms from, e.g., a sequestered agonist-antagonist combination. Naloxone that is present in the solid oral dosage form of the presently disclosed subject matter, because of its reduced bioavailability, does not act as an antagonist when one or two dosage units are consumed. However, in the event of overdose, e.g., three or more dosage units being consumed, a pharmacologically effective amount of naloxone is available from the dosage units to bind with the opioid receptors centrally and block the binding of opioids for about 20 to about 90 minutes. In one embodiment of the presently disclosed subject matter, the pharmacologically effective amount is the amount of naloxone in blood that is comparable to the amount when administered as IV or IM injection. In one embodiment of the presently disclosed subject matter, a sufficient amount of naloxone is not present in blood to cross blood-brain barrier and bind with sufficient μ-receptors when one or two dosage units are consumed.

In certain embodiments, the presently disclosed subject matter provides an oral immediate release opioid agonist-antagonist dosage form comprising Opioid Particulates comprising oxycodone hydrochloride and enteric-coated Naloxone Particulates comprising naloxone hydrochloride. In certain embodiments, when one or two units of the opioid agonist-antagonist dosage form are consumed, the enteric coat on the Naloxone Particulates is sustained until the Naloxone Particulates reach the small intestine; this delays the release of naloxone such that a sufficient amount of naloxone is not available for absorption with the opioid to reverse the opioid effect. In certain embodiments, when three or more units of the opioid agonist-antagonist dosage form of the presently disclosed subject matter are consumed, the naloxone is released from the enteric-coated Naloxone Particulates while still in the stomach (as the pH has been raised by the Triggering Particulates present in three or more dosage units); this improves the bioavailability of naloxone by providing an uncoated reservoir/bolus of naloxone reaching the small intestine. This increased amount of naloxone available for absorption saturates the hepatic first-pass metabolism, thereby providing an amount of unmetabolized naloxone in the plasma sufficient to block opioid receptors centrally, i.e., in the CNS, and reverse the effects of an opioid, e.g. in an opioid overdose event. In other words, this saturation of hepatic first-pass metabolism when three or more units of the opioid agonist-antagonist dosage form are consumed provides a higher plasma concentration of naloxone (i.e., improves bioavailability of naloxone).

In certain embodiments, the presently disclosed subject matter provides an oral immediate release opioid agonist-antagonist dosage form comprising Opioid Particulates comprising oxycodone hydrochloride and Naloxone Particulates comprising naloxone hydrochloride.

In certain embodiments, when one or two units of the opioid agonist-antagonist dosage form are consumed, the naloxone hydrochloride and oxycodone hydrochloride are released simultaneously in the stomach and reach the small intestine at essentially the same time. Naloxone is metabolized more extensively by the hepatic first-pass effect than oxycodone. In certain embodiments, when one or two dosage units are consumed, a sufficient amount of naloxone is not available in the plasma for binding with the opioid receptor to reverse the opioid effect. This is because the hepatic first-pass metabolism is not saturated by relatively small amounts of naloxone (i.e., the amount of naloxone in one or two dosage units); thus, in certain embodiments, all or almost all of the naloxone from one or two dosage units will be metabolized. In certain embodiments, the amount of naloxone present in three or more units of the opioid agonist-antagonist dosage form of the presently disclosed subject matter is sufficient to saturate the hepatic first-pass metabolism. In other words, the amount of naloxone present in a single dosage unit is an amount such that three (or more) units of the opioid agonist-antagonist dosage form of the presently disclosed subject matter is sufficient to saturate the hepatic first-pass metabolism. In certain embodiments, when three or more units of the opioid agonist-antagonist dosage form of the presently disclosed subject matter are consumed, the larger amount of naloxone is able to saturate the hepatic first-pass metabolism, resulting in larger amounts of naloxone in the plasma relative to the amount presented to the small intestine by consumption of three or more dosage units. Thus, a sufficient amount of naloxone is available for absorption with the opioid to reverse the opioid effect. In certain embodiments, the improved bioavailability of naloxone, when the first-pass metabolism is saturated, provides an amount of unmetabolized naloxone in the plasma sufficient to block opioid receptors centrally, i.e., in the CNS, and reverse the effects of an opioid overdose. In other words, the saturation of hepatic first-pass metabolism when three or more units of the opioid agonist-antagonist dosage form are consumed provides a higher plasma concentration of naloxone (i.e., improves bioavailability of naloxone).

In certain embodiments, oxycodone hydrochloride and naloxone hydrochloride (from enteric coated or non-enteric coated Naloxone Particulates) are present in about a 4:1 ratio to about a 1:4 ratio, with oxycodone hydrochloride being present in an amount of about 2.5 mg to about 20 mg and with naloxone hydrochloride being present in an amount of about 1.25 mg to about 20 mg. In certain embodiments, the oxycodone hydrochloride to naloxone hydrochloride ratio is about 4:1, about 3:1, about 2.5:1, about 2:1, about 1.75:1.25, about 1:1, about 1.25:1.75, about 1:2, about 1:2.5, about 1:3, or about 1:4.

In certain embodiments, Naloxone Particulates comprise lipid-based naloxone or amorphous solid dispersions of naloxone. In certain embodiments, such Naloxone Particulates provide enhanced oral naloxone bioavailability by avoiding first-pass metabolism of naloxone and/or by improving naloxone solubility.

In certain embodiments, the dosage form contains a Triggering Particulate population (e.g., Triggering Granule) containing an alkaline agent that increases the pH of the aqueous or nonaqueous solution to above about pH 5.0 in the presence of three or more dosage units. The Triggering Particulate can also contain a pH-stabilizing agent that maintains the increased pH above about 5.0 for up to five minutes, up to ten minutes, up to 15 minutes, up to 30 minutes, up to 45 minutes, up to one hour, up to 1.5 hours, or up to two hours or more. In certain embodiments, the increase in pH above about 5.0 reduces the dissolution of the functional coat (e.g., one or more functional coat layers), and thereby prevents or slows the release of the opioid agent from the Opioid Particulates.

In certain embodiments, the immediate release pharmaceutical dosage forms comprise a Viscosity Enhancing Particulate population (e.g., Viscosity Enhancing Granules) containing a viscosity-building polymer(s) that increases the viscosity of the aqueous or nonaqueous solution if tampered with or taken in doses above those prescribed or in a manner inconsistent with the manufacturer's instructions.

In certain embodiments, the dosage form contains a population of Ion Exchange Resin Particulates comprising at least one ion exchange resin, e.g., AMBERLITE, sodium polystyrene sulfonate, or a combination thereof.

In certain embodiments, the pharmaceutical compounds for use in the presently disclosed subject matter are those at risk for accidental (e.g., unintentional) or intentional overdose via, for example, the oral route, or misuse via, for example, the oral/intravenous/nasal/smoking route(s).

1. Definitions

The terms used in this specification generally have their ordinary meanings in the art, within the context of the presently disclosed subject matter and in the specific context where each term is used. Certain terms are discussed below, or elsewhere in the specification, to provide additional guidance to the practitioner in describing the compositions and methods of the presently disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 15%, up to 10%, up to 5%, or up to 1% of a given value. Alternatively, particularly with respect to biological systems or processes, the term can mean within an order of magnitude, preferably within five-fold, and more preferably within two-fold, of a value.

The term "active agent," "drug," "compound," "active pharmaceutical ingredient," or "API" refers to a pharmaceutically active substance which includes, without limitation, drugs susceptible to abuse and/or overdose. In certain embodiments, the active agent is an opioid analgesic.

The term "opioid" or "opioid analgesic" includes single compounds and a mixture of compounds selected from the group of opioids that provide, e.g., an analgesic effect. For example, opioids can include, without limitation, an opioid agonist, a mixed opioid agonist-antagonist, or a partial opioid agonist. In certain embodiments, the opioid can be a stereoisomer, ether, salt, hydrate or solvate thereof. The terms opioid and opioid analgesic are also meant to encompass the use of all such possible forms as well as their racemic and resolved forms thereof, and all tautomers as well. The term "racemic" refers to a mixture of equal parts of enantiomers.

The term "immediate release" or "IR" refers to dosage forms that are formulated to allow the drug to dissolve in the gastrointestinal contents/fluids with no intention of delaying or prolonging the dissolution or absorption of the drug when taken as prescribed or in a manner consistent with manufacturer's instructions.

The terms "naloxone" and "naloxone hydrochloride" can be used interchangeably.

The terms "oxycodone" and "oxycodone hydrochloride" can be used interchangeably

The term "particulate" refers to a discrete, small, repetitive unit of particles, granules, or pellets that include at least one excipient and, optionally, an active agent (e.g., an opioid agonist or opioid antagonist).

The term "multi-particulate" refers to at least two different populations of particulates.

The term "dosage form" refers to an oral particulate solid drug delivery system that, in the present technology, includes at least one or two populations of particulates.

The term "dosage unit" refers to a single tablet (e.g., tablet, tablet-in-tablet, bilayer tablet, multilayer tablet, etc.), capsule, pill, or other solid dosage form.

The term "coat" refers to a coating, layer, membrane, film, etc. applied to a surface, and, in certain embodiments, can partially, substantially, or completely surround, envelop, cover, enclose, or encase the surface of a particulate, granule, drug, dosage unit, or the like to which it is applied. For example, a coat can cover portions of the surface to which it is applied, e.g., as a partial layer, partial coating, partial membrane, or partial film, or the coat can completely cover the surface to which it is applied.

The terms "acid labile coat" or "functional coat" (or "coatings") refer to a coat comprising a component(s) that will dissolve or degrade (partially or completely) in an acidic environment (e.g., in a solution with an acidic pH). In certain embodiments, the acidic pH can be, for example, below about 7.0, below about 6.0, below about 5.0, below about 4.0, below about 3.0, or below about 2.0, or below about 1.0. Typically, the pH at which an acid labile coat/functional coat of the presently disclosed subject matter will dissolve is in the normal physiological pH (e.g., the range of normal physiological pH values) of the stomach, such as from about 1 to about 5, from about 1 to about 4, or from about 2 to about 3. Typically, the acid labile coat/functional coat dissolves or degrades more slowly, or to only a small extent, when present in a solution with a pH that is considered not acidic (e.g., nonacidic and/or less acidic; e.g., at a pH above about 5, above about 6, or above about 7). It will be understood that the acid labile coat/functional coat can be prepared and designed to dissolve or degrade (partially or substantially) within any desired pH range, and to not dissolve or degrade (partially or substantially) within any desired pH range. For example, the acid labile coat/functional coat can be designed to dissolve at any pH, e.g., below about 5; above that level, dissolution is inhibited, reduced or slowed. As the pH increases, the dissolution/degradation can slow further, and can stop nearly completely. The acid labile coat/functional coat affects the rate of release, in vitro or in vivo, of an opioid(s). Such coatings or coats are sometimes referred to as "rate-limiting" or "rate-controlling"; the particular polymer(s) responsible for affecting the rate of release in the coating or coat can also be referred to as "rate-limiting" or "rate-controlling." An acid labile coat/functional coat can comprise one or more functional coat layers.

The term "enteric coat" refers to a coat that is stable in the highly acidic pH environment of the stomach, but breaks down/dissolves at less acidic (relatively more basic) pH. For example, an enteric coat will not dissolve in the stomach but will break down/dissolve in the basic pH environment of the small intestine. In addition, an enteric coat will break down/dissolve in the stomach if the environment of the stomach becomes less acidic (i.e., relatively more basic), as can occur in the presently disclosed subject matter when sufficient Triggering Particulates release sufficient alkaline agent (e.g., when three or more dosage units containing Triggering Particulates are consumed). Materials used for enteric coating include hydroxypropyl methylcellulose acetate succinate (HPMCAS), hydroxypropyl methylcellulose acetate phthalate (HPMCAP), cellulose acetate phthalate (CAP), polyvinyl acetate phthalate (PVAP), and anionic copolymers based on methacrylic acid and methyl methacrylate. Examples of anionic polymers include EUDRAGIT L and EUDRAGIT S, which are referred to as enteric polymers and can be any anionic copolymer based on methacrylic acid and methyl methacrylate. Examples include Eudragit L 100, Eudragit L 12.5, Eudragit S 12.5, and Eudragit S 100. The ratio of free carboxyl groups to ester groups is approximately 1:1 in Eudragit L 100 and approximately 1:2 in Eudragit S 100.

The term "alkaline agent" can be used to refer to an excipient that acts to increase the pH of, e.g., the gastric fluid (e.g., roughly pH 1.2-4.5) to a pH greater than about 5.0. For example, alkaline agent can refer to substances that are capable of increasing the pH to greater than 4.5, greater than 5.0, greater than 5.5, etc. It also refers to basic substances and substances that can convert an acidic environment to a less acidic or a basic environment. Typically, these agents, when present in a sufficient amount, are able to raise the pH of the stomach to beyond physiological levels and thereby prevent, reduce, or inhibit dissolution of an acid labile substance or coat. Examples of alkaline agents include: aluminum hydroxide, sodium hydroxide, potassium hydroxide, calcium hydroxide, magnesium hydroxide, aluminum oxide, sodium oxide, potassium oxide, calcium oxide, magnesium oxide, calcium carbonate, sodium carbonate, potassium bicarbonate, sodium bicarbonate, ammonia, tertiary sodium phosphate, diethanolamine, ethylenediamine, N-methylglucamine, L-lysine, and combinations thereof.

The term "pH-stabilizing agent" refers to salts of weak acids/weak bases that act to maintain or stabilize the elevated pH of gastric fluid caused by the alkaline agent. For example, a pH-stabilizing agent(s) maintains the pH of the gastric fluid at a pH greater than 5.0 for a finite time.

The term "viscosity-building polymer" as used herein refers to a polymer or group of polymers that increase the viscosity of a solution if the dosage form is tampered with or taken in doses above those prescribed or in a manner inconsistent with the manufacturer's instructions.

The term "nonionic polymer" refers to a nonionic pH-independent polymer.

The term "water-insoluble nonionic polymer" refers to a nonionic polymer generally insoluble in water, physiological fluids, and ethanol.

The term "water-soluble nonionic polymer" refers to a nonionic polymer generally soluble in water, physiological fluids, and ethanol.

The term "cationic polymer" refers to a cationic pH-dependent polymer, generally soluble in a particular pH range, e.g., gastric fluid or simulated gastric fluid (SGF) (e.g., a polymer, containing one or more cationic groups, soluble in, e.g., gastric fluid or SGF).

The term "mini-tablet" refers to a tablet with a diameter equal to or smaller than 4 mm. They can be filled into a capsule or compressed into a larger tablet.

The term "abuse-deterrent formulation," "abuse-deterrent composition," "abuse-resistant formulation," "abuse-resistant composition," or "ADF" are used interchangeably to refer to a dosage form that reduces the potential for abuse but delivers a therapeutically effective dose when administered as directed. For example, these terms refer to a dosage form that can be at least resistant, with or without heat treatment or freezing, to crushing, grinding, melting, cutting, extracting, dose dumping (e.g., alcohol dose dumping), and solubilizing for injection purposes. Improper administration includes, without limitation, tampering with the dosage form and/or administering the drug by any route other than that instructed. For example, and without limitation, improper administration includes snorting after grinding, administration after heat treatment, oral administration after crushing, or parenteral administration after extraction with a solvent such as water, ethanol, isopropanol, acetone, acetic acid, vinegar, carbonated beverages, and the like, and combinations thereof.

The term "abuse" means the intentional, nontherapeutic use of a dosage form or active agent, to achieve a desirable psychological or physiological effect. For example, these terms refer to tampering with the dosage form and/or administering the drug in a manner inconsistent with the manufacturer's instructions. Methods of tampering or abuse include, but are not limited to, crushing, grinding, melting, cutting, heating, freezing, extracting, dose dumping (e.g., alcohol dose dumping), and solubilizing for injection purposes.

The term "in a manner inconsistent with the manufacturer's instructions" is meant to include, but is not limited to, consuming amounts greater than amounts described on the label or prescribed by a licensed physician, and/or altering by any means (e.g., crushing, breaking, milling, melting, separating, etc.) the dosage forms such that the active agent can be crushed, ground, melted, cut, extracted, dose dumped (e.g., alcohol dose dumping), and/or solubilized for injection purposes.

The term "syringeability" refers, for example, to the ability of an agent (e.g., an opioid) to be extracted from a product formulation or dosage form into a syringe, i.e., the agent is in a syringeable form. For example, a solid dosage form can be dissolved/suspended in water, and an agent present in the dosage form can be extracted from the resulting liquid into a syringe in the form of a syringeable liquid.

The term "available in syringeable form," as used herein, refers to availability of an agent (e.g., an opioid) to be extracted into a syringe from a solution/suspension of a solid dosage form. The amount or percentage of such extracted agent could be termed as the amount or percentage available in syringeable form, or available as a syringeable liquid, or the like.

The term "crush resistant" or "resistant to crushing" means, for example, a granule or particulate (e.g., an Opioid Granule) that can deform but does not break into powder form when pressure greater than 500 N is applied, when using a suitable hardness tester. Such resistance to crushing deters the abuse of the dosage form.

The term "grinding" refers to a process of reducing, or attempting to reduce, one or more tablets into small fragments, e.g., in the form of powder, following a specific grinding pattern (e.g., two minutes grinding/one minute rest/two minutes grinding) using, for example, an electrical grinding means (e.g., coffee grinder or IKA grinder).

The terms "resistant to alcohol extraction" and "resistant to alcohol dose-dumping" are used to refer to two or more dosage units (e.g., any form(s) of tablets or capsules) that at least fulfill the condition that in vitro dissolution, characterized by the percentage of active agent released at, e.g., 30 minutes or 60 minutes of dissolution, when measured in a USP Apparatus 1 (basket) at 100 rpm in 900 ml simulated gastric fluid comprising 40% ethanol at 37° C., deviates no more than 20% from the corresponding in vitro dissolution measured at the same time point in the same apparatus at the same speed in 900 ml SGF without ethanol at 37° C. Such resistance to alcohol dose dumping deters the abuse of the dosage form.

The term "overdose protection" or "ODP" refers to an oral dosage form that reduces the potential for overdose but delivers a therapeutically effective dose when administered as directed or ordered by a licensed physician.

The term "overdose" refers to the administration of the dosage form in amounts or doses above those considered therapeutic (e.g., three or more dosage units; more than two dosage units); in a manner inconsistent with manufacturer's instructions; or in a manner not prescribed. Overdose can be intentional or unintentional (e.g., accidental).

The term "solid carrier," "substrate," or "carrier" refers to a carrier of an active ingredient (e.g., opioids, amorphous solid dispersion (ASD) of naloxone, lipid-based naloxone) and/or excipients (e.g., lipids, water soluble polymer) in a solid oral dosage form.

As used herein, the phrase "therapeutically effective amount" or "pharmaceutically effective amount" means an amount that provides the specific response for which the agent is administered to a subject in need of such treatment, for whatever reason. It is emphasized that a therapeutically effective amount will not always be effective in treating the target conditions/diseases, even though such amount is deemed to be a therapeutically effective amount by those of skill in the art. For illustration only, exemplary doses and therapeutically effective amounts are provided below with reference to adult human subjects. Those skilled in the art can adjust such amounts in accordance with standard practices as needed to treat a specific subject and/or condition/disease.

As used herein, the phrase "pharmacologically effective amount" refers to an amount that will elicit a desired effect in the subject not directly related to treatment of a condition and/or disease. For illustration only, related to naloxone, the exemplary desired response is to reverse/prevent an opioid effect by blocking the binding of opioid to central opioid receptors.

As used herein, the phrase "pharmaceutically acceptable salts" should be ascribed its customary meaning and includes, but is not limited to, inorganic acid salts such as hydrochloride, hydrobromide, sulfate, phosphate, and the like; organic acid salts such as formate, acetate, trifluoroacetate, maleate, tartrate, and the like; sulfonates such as methanesulfonate, benzenesulfonate, p-toluenesulfonate, and the like; amino acid salts such as arginate, asparaginate, glutamate, and the like; metal salts such as sodium salt, potassium salt, cesium salt, and the like; alkaline earth metals such as calcium salt, magnesium salt, and the like; and organic amine salts such as triethylamine salt, pyridine salt, picoline salt, ethanolamine salt, triethanolamine salt, discyclohexylamine salt, N,N'-dibenzylethylenediamine salt, and the like.

The phrase "hydro-organic solvent" refers to a mixture of two solvents, usually defined in volume to volume (v/v) concentration, in which an organic solvent is measured and diluted by water up to a final volume.

The term "amorphous solid dispersion" refers to dispersion of a drug in a solid matrix where the matrix is either a small molecule or polymer. The dispersed state includes the drug in amorphous form.

As used herein, use of phrases such as "decreased," "reduced," "diminished," or "lowered" is meant to include at least a 10% change in, e.g., the release of an active agent, with greater percentage changes being preferred for reduction in abuse potential and overdose potential. For example, but without limitation, the change can be greater than 25%, 35%, 45%, 55%, 65%, 75%, 85%, 95%, 96%, 97%, 98%, 99%, or increments therein.

2. Opioid Particulates

Opioid Particulates contain at least one opioid agonist agent. In certain embodiments, the Opioid Particulates are Opioid Granules, Opioid Pellets, or a combination thereof.

2.1. Opioid Agents

In certain embodiments, the Opioid Particulates contain at least one opioid agent, e.g., oxycodone hydrochloride. The Opioid Particulates can be coated with at least one functional coat layer (e.g., FC 1). In certain embodiments, FC 1 includes a nonionic polymer that is insoluble in water and a cationic polymer that behaves as a pore former at a pH from about 1.2 to about 4.5 or about 5.0 and is insoluble in fluids with a pH above about 5.0 (e.g., at a pH of about 5.0 or greater). Surprisingly, it has been found that a functional coat (e.g., at least one functional coat layer present in Opioid Particulates) containing, e.g., an 80:20, or higher, wt % ratio of nonionic polymer to pore former provides much better ODP compared to a functional coat with, e.g., a 60:40 wt % ratio of nonionic polymer to pore former, while maintaining a therapeutically acceptable immediate release of, e.g., an opioid(s) when taken in a manner consistent with manufacturer's instructions, or in a manner prescribed (e.g., one or two dosage units are taken as intended).

In certain embodiments, the pharmaceutically active opioid agent is present in the dosage form in an amount effective for the intended therapeutic purpose. These amounts are well known in the art. Indeed, the doses at which any of the presently known opioid agents embraced by the presently disclosed subject matter can be given safely and effectively for the intended therapeutic purpose are known to those of skill in the art. In certain embodiments, the opioid is present in an amount of about 0.1% to about 95% w/w of the Opioid Particulate before the addition of the (optional) seal coat, or any functional coat layer(s) (i.e., about 0.1% to about 95% w/w of the polymer matrix embedded with the opioid). In certain embodiments, the opioid is present in an amount of about 0.2% to about 90%, about 0.3% to about 85%, about 0.4% to about 80%, about 0.5% to about 75%, about 0.6% to about 70%, about 0.7% to about 65%, about 0.8% to about 60%, about 0.9% to about 55%, about 1% to about 50%, about 2.5% to about 45%, about 5% to about 40%, about 7.5% to about 35%, about 10% to about 30%, about 12.5% to about 25%, or about 15% to about 20% w/w of the polymer matrix embedded with the opioid. In certain embodiments, the opioid is present in an amount of at least about 0.1%, at least about 0.2%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% w/w of the polymer matrix embedded with the opioid.

In certain embodiments, the opioid analgesic can be oxycodone, hydrocodone, tapentadol, codeine, oxymorphone, hydromorphone, or pharmaceutically acceptable salts thereof. In certain embodiments, the opioid is oxycodone, hydrocodone, oxymorphone, hydromorphone, or codeine. In certain embodiments, the opioid is a pharmaceutically active salt of oxycodone, hydrocodone, oxymorphone, hydromorphone, or codeine.

Examples of pharmaceutically acceptable salt include, but are not limited to, citrate, oxalate, acetate, maleate, malonate, fumarate, succinate, tosylate, mesylate, hydrochloride, hydrobromide, sulfate, phosphate, methanesulfonate, toluenesulfonate or mixtures and/or forms thereof. Additional pharmaceutically acceptable salts can be found in P. H. Stahl and C. G. Wermuth, editors, Handbook of Pharmaceutical Salts: Properties, Selection and Use, Weinheim/Zürich:Wiley-VCH/VHCA, 2002.

2.2. Opioid Pellets

In certain embodiments, the Opioid Particulates are Opioid Pellets. In certain embodiments, the Opioid Pellets include an opioid and a functional coat layer(s). In certain embodiments, at least one of FC 0, FC 1, and FC 2 contain at least one cationic polymer and, optionally, a nonionic water-insoluble polymer. In certain embodiments, the Opioid Pellets can further include a seal coat (optional) between the polymer matrix (or alternate core) and a functional coat layer(s). In certain embodiments, the Opioid Pellets further include an over coat, comprising a water-soluble nonionic polymer, on top of the outermost functional coat layer(s). In certain embodiments, a functional coat, e.g., FC 1, includes a water-insoluble nonionic polymer, and a cationic polymer that is soluble in gastric fluids (e.g., at a pH less than about 5.0). The cationic polymer behaves as a pore former at a pH below about 5.0, but swells and becomes permeable at a pH above about 5.0 (e.g., in intestinal fluids), thereby substantially preventing release of the opioid at a higher pH.

In certain embodiments, the core of the Opioid Pellets can be preformed pellets. By way of example, but not limitation, the pellet core can be made from microcrystalline cellulose (MCC) and/or alkaline agents/ion exchange resins. In certain embodiments, the pellet core comprises MCC cellets containing cured PEO.

In certain embodiments, the shape of the pellets can be round, oval, or oblong.

In certain embodiments, that pellet core has a density of about 0.3 to about 1.0 mg/cm$^3$.

In certain embodiments, the pellet core can be about 25 mg to about 500 mg. In certain embodiments, the pellet core can be about 50 mg to about 475 mg, about 75 mg to about 450 mg, about 100 mg to about 425 mg, about 125 mg to about 400 mg, about 150 mg to about 375 mg, about 175 mg to about 350 mg, about 200 mg to about 325 mg, about 225 mg to about 300 mg, or about 250 mg to about 275 mg.

In certain embodiments, the pellet core can be about 25% to about 90% w/w of the uncoated Opioid Pellet, i.e., the Opioid Pellet before being coated with an (optional) seal coat and/or a functional coat layer(s). In certain embodiments, the pellet core can be about 27.5% to about 87.5%, about 30% to about 85%, about 32.5% to about 82.5%, about 35% to about 80%, about 37.5% to about 77.5%, about 40% to about 75%, about 42.5% to about 72.5%, about 45% to about 70%, about 47.5% to about 67.5%, about 50% to about 65%, about 52.5% to about 62.5%, or about 55% to about 60% w/w of the uncoated Opioid Pellet.

In certain embodiments, Opioid Pellets contain an opioid in an amount of about 0.1% to about 95% w/w of the uncoated Opioid Pellets. In certain embodiments, e.g., Opioid Pellets contain the opioid in an amount of about 0.2% to about 90%, about 0.3% to about 85%, about 0.4% to about 80%, about 0.5% to about 75%, about 0.6% to about 70%, about 0.7% to about 65%, about 0.8% to about 60%, about 0.9% to about 55%, about 1% to about 50%, about 2.5% to about 45%, about 5% to about 40%, about 7.5% to about 35%, about 10% to about 30%, about 12.5% to about 25%, or about 15% to about 20% w/w of the uncoated Opioid Pellet. In certain embodiments, the Opioid Pellets contain the opioid in an amount of at least about 0.1%, at least about 0.2%, at least about 0.3%, at least about 0.4%, at least about 0.5%, at least about 0.75%, at least about 1%, at least about 2.5%, at least about 5%, at least about 7.5%, at least about 10%, at least about 12.5%, at least about 15%, at least about 17.5%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% w/w of the uncoated Opioid Pellet.

In certain embodiments, the opioid is oxycodone, or a pharmaceutically acceptable salt thereof. In certain embodiments, the opioid is oxycodone hydrochloride. In certain embodiments, the Opioid Pellets contain an opioid and an opioid antagonist, e.g., naloxone hydrochloride.

In certain embodiments, the opioid and, optionally, naloxone hydrochloride can be absorbed by the pellet core. In certain embodiments, the opioid and, optionally, naloxone hydrochloride can be coated onto the pellet core. In certain embodiments, the opioid and, optionally, naloxone hydrochloride can be dissolved into a suitable solvent system to either be absorbed by the pellet core or sprayed onto the pellet core. In certain embodiments, the solvent is water, an alcohol, an organic liquid, or a combination thereof. In certain embodiments, the alcohol is a dehydrated alcohol. In certain embodiments, the solvent is a mixture of water and an alcohol. In certain embodiments, the solvent is a mixture of water and a dehydrated alcohol. In certain embodiments, the components of a solvent mixture can be added at the same time or in different steps or stages.

In certain embodiments, solvents that can be used in processes of preparing dosage forms (e.g., dosage forms comprising Opioid Pellets) include, but are not limited to, water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and any mixtures thereof.

In certain embodiments, the Opioid Pellet coating can also contain additives such as coloring agents, talc and/or magnesium stearate, which are well known in the coating arts. In certain embodiments, the excipients added to the active agent solution can include, but are not limited to hydroxypropylmethylcellulose (HPMC) (e.g., methocel E5 Premium LV), lactose, polyvinylpyrrolidone (PVP), magnesium stearate, and talc. In certain embodiments, the excipients can be present in an amount of about 0.1% to about 30% w/w of the uncoated Opioid Pellet. In certain embodiments, the Opioid Pellets contain excipients in an amount of about 0.2% to about 27.5%, about 0.3% to about 25%, about 0.4% to about 22.5%, about 0.5% to about 20%, about 0.6% to about 17.5%, about 0.7% to about 15%, about 0.8% to about 12.5%, about 0.9% to about 10%, about 1% to about 7.5%, or about 2.5% to about 5% w/w of the uncoated Opioid Pellet. In certain embodiments, the Opioid Pellets contain excipients in an amount of at least about 0.1%, at least about 0.2%, at least about 0.5%, at least about 1%, at least about 5%, at least about 10%, at least about 15%, at least about 20%, at least about 25%, or at least about 30% w/w of the uncoated Opioid Pellet.

In certain embodiments, Opioid Pellets can be made by coating the opioid and, optionally, naloxone upon the pellet core.

2.3. Opioid Granules

In certain embodiments, the Opioid Particulates are Opioid Granules. In certain embodiments, the Opioid Granules include an opioid, a polymer matrix that in some embodiments can include hydrophilic polyoxyethylene (PEO) polymer, a cationic polymer or a nonionic polymer, an antioxidant, a plasticizer and a surfactant. In certain embodiments, the Opioid Granules can include a seal coat and at least one functional coat layer(s) (e.g., FC 1). In certain embodiments, the seal coat is optional. In certain embodiments, Opioid Granules containing, e.g., FC 1 can further include FC 0 between the polymer matrix and FC 1. In certain embodiments, the Opioid Particulates include FC 2 over FC 1. In certain embodiments, the Opioid Particulates include an over coat, comprising a water-soluble nonionic polymer, surrounding the outermost functional coat layer(s). In certain embodiments, at least one of FC 0, FC 1, and FC 2 includes a water-insoluble nonionic polymer (e.g., generally not soluble in physiological fluids and commonly used organic solvents such as ethanol) and a cationic polymer. The latter behaves as a pore former at a pH below about 5.0, but swells and becomes partially permeable at a pH above 5.0 (e.g., in intestinal fluids, or in gastric fluids with an elevated pH), thereby substantially preventing release of the opioid at higher pH.

In certain embodiments, the Opioid Granules include an opioid and an opioid antagonist, e.g., naloxone hydrochloride.

In certain embodiments, Opioid Granules can contain a plasticizer in the polymer matrix, the outer coatings (e.g., the seal coat, the functional coat layer(s), and/or the over coat), or both the polymer matrix and the outer coatings. In certain embodiments, the Opioid Granules can contain a surfactant in the polymer matrix, the outer coatings, or in both the polymer matrix and the outer coatings.

In certain embodiments, Opioid Granules contain an opioid in an amount of about 0.1% to about 95% w/w of the uncoated Opioid Granules, i.e., the Opioid Granules before being coated with the (optional) seal coat and/or any functional coat layer(s).

In certain embodiments, the opioid is oxycodone, or a pharmaceutically acceptable salt thereof. In certain embodiments, the opioid is oxycodone hydrochloride. In certain embodiments, the opioid is hydrocodone, or a pharmaceutically acceptable salt thereof. In certain embodiments, the opioid is hydrocodone bitartrate. In certain embodiments, the opioid is hydromorphone, or a pharmaceutically acceptable salt thereof. In certain embodiments, the opioid is hydromorphone hydrochloride. In certain embodiments, the opioid is oxymorphone. In certain embodiments, the opioid is codeine, or a pharmaceutically acceptable salt thereof.

In certain embodiments, the polymer matrix comprises a nonionic polymer and/or a cationic polymer. Representative cationic polymers include, but are not limited to, (meth)acrylic polymers and (meth)acrylic copolymers (e.g., copolymers of alkyl (meth)acrylates and copolymers of alkylamino(meth)acrylates); quarternary ammonium (meth)acrylic polymers.

Representative nonionic polymers include, but are not limited to, a nonionic copolymer of ethyl acrylate, methyl methacrylate and a low content of methacrylic acid ester with quaternary ammonium groups (ammonium methacrylate copolymer, Type A, NF) (e.g., EUDRAGIT® RL 100, RS100 (Evonik)); and nonionic polymers such as hydroxypropylcellulose (e.g., KLUCEL®, L, J, G, M and H grades (Ashland)), hydroxypropyl methylcellulose (HPMC) (e.g., METHOCEL® E, F, J, and K (Dow Chemicals)), hydroxyethylcellulose (e.g., NATRASOL L, G, M, and H grades (Ashland)), ethylcellulose (e.g., ETHOCEL® 7FP, 10FP, 45FP, and 100FP (Dow Chemicals) and N7, N10, N14, N22, N50, and N100 grades (Ashland)), cellulose acetate butyrate (e.g., CAB-381-0.5 (Eastman)), and cellulose acetate (CA-398-3, CA-398-6, CA-398-100, and CA-398-30 (Eastman)); polyvinyl acetate polymers (e.g., polyvinyl acetate-polyvinylpyrrolidone (Kollidon SR) and polyethylene oxide polymers (e.g., POLYOX® WSR coagulant, POLYOX® WSR-301, POLYOX® WSR-303). Exemplary polyoxyethylene oxide polymers include POLYOX™ WSR N-80, POLYOX™ WSR N-750, POLYOX™ WSR N-3000, POLYOX™ WSR-205, POLYOX™ WSR N-1105, POLYOX™ WSR N-12K, POLYOX™ WSR N-60K, POLYOX™ WSR N-301, POLYOX® WSR Coagulant, POLYOX™ WSR N-303. The exemplary polyoxyethylene oxide polymers provide different viscosities in an aqueous solution. In certain embodiments, the exemplary polyethylene oxide has an average molecular weight of about 1,000,000 (WSR-N-12K), about 4,000,000 (WSR-301), about 5,000,000 (WSR Coagulant), or about 7,000,000 (WSR-303).

Representative pH-dependent polymers include, but are not limited to, cationic pH-dependent release polymers that are soluble in gastric fluid, but swell and become permeable at a pH above 5.0. In some embodiments, the cationic pH-dependent polymer matrix comprises EUDRAGIT® E PO which has a molecular weight about 47,000 and a glass transition temperature about 48° C.

The polymer matrix (i.e., the polymer matrix without the opioid agonist/(optional) opioid antagonist embedded within) can be present in the Opioid Granules in a range of about 1.0% to about 95% w/w based on the total weight of the uncoated Opioid Granule, in some embodiments, from about 15% to about 90% w/w based on the total weight of the uncoated Opioid Granule, and in other embodiments, from about 30% to about 75% w/w based on the total weight of the uncoated Opioid Granule. In certain embodiments, the polymer matrix can be present in an amount of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% w/w based on the total weight of the uncoated Opioid Granule.

In certain embodiments, a plasticizer can be added to increase the elasticity of the polymer in Opioid Granules. In certain embodiments, the plasticizer makes the Opioid Granule crush-resistant. In certain embodiments, the plasticizer is soluble in both aqueous and nonaqueous solvents that are commonly used to extract opioids and other abuse-prone drugs from commercial formulations. In certain embodiments, the plasticizer acts as an aversion agent. In certain embodiments, the plasticizer acts as a tissue irritant that causes discomfort if administered in conjunction with an opioid with which it is coextracted.

Representative plasticizers include, but are not limited to liquid esters, (e.g., triethyl citrate, propylene glycol, polyethylene glycols, triacetin, diethylene glycol monoethyl ether, dibutyl sebacate, and diethyl phthalate). In certain embodiments, the dielectric constant values of the plasticizer are in a range of about 5 to about 60. In other embodiments, the dielectric constant values of the plasticizer are in a range of about 10 to about 40.

In certain embodiments, the plasticizer can be present in an amount that is sufficient to make the Opioid Granules substantially crush-resistant, but not in quantities that negatively impact the dissolution of the opioid agent when taken in a manner consistent with the manufacturer's instructions or in a manner not prescribed. In certain embodiments, the plasticizer can be present in amounts that result in discomfort to the abuser when the plasticizer is co-eluted with the opioid and administered in a manner inconsistent with the manufacturers and/or physicians instructions. In certain embodiments, the amount of plasticizer provides an adequate rubbery state and elongation property to the polymer to achieve crush-resistance, making it difficult to pulverize the Opioid Granules into a fine powder, thereby deterring abuse.

In certain embodiments, the plasticizer can be present in a range of about 0.1% to about 30% w/w of the uncoated Opioid Granules. In certain embodiments, the plasticizer can be present in a range from about 2.0% to about 15% w/w of the uncoated Opioid Granules. In certain embodiments, the plasticizer can be present in an amount of about 0.2% to about 27.5%, about 0.3% to about 25%, about 0.4% to about 22.5%, about 0.5% to about 20%, about 0.6% to about 17.5%, about 0.7% to about 15%, about 0.8% to about 12.5%, about 0.9% to about 10%, about 1% to about 7.5%, or about 2.5% to about 5% w/w of the uncoated Opioid Granule. In certain embodiments, the plasticizer can be present in an amount of at least about 0.1%, at least about 0.2%, at least about 0.5%, at least about 1%, at least about 5%, at least about 10%, at least about 15%, at least about 20%, at least about 25%, or at least about 30% w/w of the uncoated Opioid Granule. In certain embodiments, the plasticizer can be present in an amount of about 2%, about 3%, about 4%, about 6%, or about 8% w/w of the uncoated Opioid Granule.

In certain embodiments, the Opioid Granule matrix further comprises at least one surfactant. In certain embodiments, the pharmaceutically acceptable surfactants that are useful in the practice of the presently disclosed subject matter have solubility in oils, co-solvents, or aqueous media. In certain embodiments, the surfactant component helps in modulating the solubility of the opioid. In certain embodiments, the surfactant helps to reducing the abuse potential by a dual mechanism. First, it elicits the irritant response when administered "as is" by nasal or injection routes, and second, by co-eluting with the drug when extracted with the commonly used solvents such as aqueous and organic solvents. Surfactants produce tissue irritation when applied to nasal mucosa and will cause local irritation at an injection site. Further, docusate sodium is commonly used as a stool softener/laxative, so while providing some relief for opioid-induced constipation at the intended dose, it can cause undesirable gastrointestinal effects if large quantities are ingested. Similar gastrointestinal effects can be obtained by ingesting other surfactants. In certain embodiments, the surfactant is present in an amount that results in discomfort to the abuser when the surfactant is co-eluted with the pharmaceutically active agent. The hydrophilic-lipophilic balance ("HLB") values of the surfactants are in a range of about 4 to about 30.

Types of surfactants that can be useful in the practice of the presently disclosed subject matter include nonionic surfactants (e.g., esters of fatty acids, especially of C8-C24 and preferably of C16-C22, and fatty acid esters of polyols such as glycerol or sorbitol); sorbitan fatty acid esters ethoxylated with from 2 to 30 moles of ethylene oxide; polyethylene glycol fatty acid esters; polyethyleneglycol esters and polyethyleneglycol ethers; and polyethoxylated carboxylic acids (e.g., PEG-35 castor oil, PEG-40 castor oil, steareth-2 (e.g., Brij 72, Uniqema), steareth-21 (e.g., Brij 721, Uniqema), ceteareth-25 (e.g., Cremophor A25, BASF Cooperation), PEG-7 hydrogenated castor oil (e.g., Cremophor WO7, BASF Cooperation), and PEG-30 dipolyhydroxystearate (e.g., Arlacel P 135, Uniqema)); block copolymers based on ethylene oxide and propylene oxide (e.g., PLURONIC® (e.g., 188 or 407 (BASF)); dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; and polyoxyl 40 stearate. Anionic surfactants (e.g., alkyl ether sulfates and sulfosuccinates) can also be useful. Alternatively cationic and amphoteric surfactants such as phospholipids, lysophospholipids, and pegylated phospholipids can also be used. Additional useful surfactants include, vitamin E and derivatives thereof (e.g., PEGylated derivatives of vitamin E such as tocopherol PEG succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate, and tocotrienol polyethylene glycol phthalate). See, e.g., USPAP 2014/0271593, hereby incorporated-by-reference in its entirety herein).

In certain embodiments, the surfactant can be present in a range of about 0.01% to about 15% w/w of the uncoated Opioid Granules. In certain embodiments, the surfactant can be present in a range from about 0.15% to about 5% w/w of the uncoated Opioid Granules. In certain embodiments, the surfactant can be present in an amount of about 0.025 to about 12.5%, about 0.05% to about 10%, about 0.075% to about 7.5%, about 0.1% to about 5%, about 0.25% to about 2.5%, or about 0.5% to about 1% w/w of the uncoated Opioid Granules. In certain embodiments, the surfactant can be present in an amount of about 0.2%, about 0.5%, about 2%, or about 2.2%, w/w of the uncoated Opioid Granules.

In certain embodiments, certain combinations of aversion agents (e.g., plasticizer and surfactant) can be used to deter abuse. Examples of such combinations include, but are not limited to, triethyl citrate and docusate sodium (DOSS™); propylene glycol and DOSS™; polyethylene glycol (PEG-400) and DOSS™; and PEG-400 or PEG-40 hydrogenated castor oil. In certain embodiments, surfactants are used as aversion agents. Examples of such surfactants include, but are not limited to, Polyoxyl 40 hydrogenated castor oil (Cremaphor RH40), PEG 35 castor oil, and Polyoxyl 35 hydrogenated castor oil (Cremaphor EL). In certain embodiments, plasticizers are used as aversion agents. Examples of such plasticizers include, but are not limited to, PEG-3350 and PEG-6000.

In certain embodiments, the Opioid Granules further contain an antioxidant. In certain embodiments, the antioxidants are present in an amount sufficient to suppress degradation of high molecular weight PEO upon hot melt extrusion (HME). Polymer degradation can result in an uncontrolled release profile, particularly when active material is embedded in a matrix of PEO; this can be another cause of oxidative degradation of pharmacologically active ingredients by, e.g., radicals. When adding an excipient, such as butylated hydroxytoluene (BHT), in order to attempt to stabilize high molecular weight PEO polymer, it should be taken into consideration that such an excipient should be stable at elevated temperatures, e.g., hot-melt extrusion temperatures used during manufacture of Opioid Granules. Antioxidants for use in the presently disclosed subject matter include, but are not limited to, ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. In certain embodiments, the antioxidant can be present in a range of about 0.01% to about 2% w/w of the uncoated Opioid Granules. In certain embodiments, the antioxidant can be present in a range of about 0.025% to about 1%, about 0.05% to about 0.75%, about 0.075% to about 0.5%, or about 0.1 to about 0.75% w/w of the uncoated Opioid Granules. In certain embodiments, the antioxidant can be present in about 0.2%, about 0.3%, about 0.4%, or about 0.5% w/w of the uncoated Opioid Granules.

In certain embodiments, the Opioid Granules can be prepared in several ways known to those in the art, including HME, film melt, granulation, melt granulation, extrusion spheronization, or rotor or roller compaction. In certain embodiments, the Opioid Granules, containing PEO polymers, prepared by granulation, extrusion (e.g., HME), spheronization, rotor, or roller compaction process can require curing at a temperature above the melting point of the PEO polymers. In certain embodiments, the Opioid Granules can be prepared by an HME process. In an HME process, a thermoplastic carrier polymer (e.g., nonionic polymer and/or cationic polymer) is combined with an opioid, a plasticizer, a surfactant, as well as any optional ingredients (e.g., an ion exchange polymer, alkaline buffering agent, and/or viscosity-building agent) to form a powdery mixture. The mixture is introduced into one or two rotating screws that convey the powder into a heated zone where shear forces compound the materials until a molten mass is achieved. Hot-melt extrusion equipment typically includes an extruder, auxiliary equipment for the extruder, downstream processing equipment, and other monitoring tools used for performance and product quality evaluation. The extruder is typically composed of a feeding hopper, barrels, single or twin screws, and the die and screw-driving unit. The auxiliary equipment for the extruder mainly includes a heating/cooling device for the barrels, a conveyer belt to cool down the product, and a solvent delivery pump. The monitoring devices on the equipment include temperature gauges, a screw-speed controller, an extrusion torque monitor and pressure gauges. In certain embodiments, different shaped dies can be used. For example, extrudates can be produced by extruding the material through round-shaped dies into cooled rolls, wherein the extruded strands are cut into short cylinders using a pelletizer.

The pelletized extruded strands are subjected to an appropriate size reduction process(es) using co-mill or fitz mill or micropulverizer with coolant processing aids such as dry ice or liquid nitrogen.

In certain embodiments, the sizes of Opioid Granules, before or after attempted grinding, are large enough to prevent the granules from being snorted. In certain embodiments, the mean size distribution of the Opioid Granules can be from about 125 µm to about 1000 µm (1 mm), and in some embodiments from about 250 µm to about 750 µm (as measured by weight frequency distribution using sieving method). In certain embodiments, the mean particle size of the Opioid Granules is about 400 µm to about 600 µm. In certain embodiments, the mean particle size of the Opioid Granules is about 500 µm.

2.4. Seal Coat

In certain embodiments, the Opioid Particulates can be seal coated. The seal coat can be disposed between the inner polymer matrix core (i.e., the polymer matrix with an opioid embedded within) and the at least one functional coat (i.e., FC 1). In certain embodiments, the seal coat can be made with a nonionic water-soluble polymer. In certain embodiments, the nonionic water soluble polymer that can be included in the seal coat is a cellulose ether polymer (e.g., a water-soluble methylcellulose and/or hydroxypropylmethylcellulose polymer). In certain embodiments, the amount of the polymer ranges from about 5% to about 100% w/w of the total weight of the composition of the seal coat (also noted within as "seal coat composition"), in some embodiments from about 30% to about 95% w/w based on the total weight of the composition of the seal coat and in some embodiments from about 50% to about 75% w/w based on the total weight of the seal coat composition. In certain embodiments, the amount of the polymer ranges from about 10% to about 95%, about 15% to about 90%, about 20% to about 85%, about 25% to about 80%, about 30% to about 75%, about 35% to about 70%, about 40% to about 65%, about 45% to about 60%, or about 50% to about 55% w/w of the total weight of the seal coat composition.

In certain embodiments, the composition of the seal coat can also include additional excipients such as an anti-tacking agent (e.g., talc, magnesium trisilicate, colloidal silicon dioxide (e.g., CAB-O-SIL®)) and a plasticizer; the plasticizer can be the same as or different from the plasticizer(s) that can be present in Opioid Particulates. In certain embodiments, the amount of the additional excipients, when present, can range from about 0.1% to about 40% w/w of the total weight of the seal coat composition, and in some embodiments from about 0.5% to about 10% w/w based on the total weight of the seal coat composition. In certain embodiments, the additional excipients are present at about 0.5% or about 4% w/w based on the total weight of the seal coat composition. In certain embodiments, the additional excipients are present at about 0.25% or about 35%, about 0.5% or about 30%, about 0.75% or about 25%, about 1% or about 20%, about 2.5% or about 15%, or about 5% or about 10% w/w based on the total weight of the seal coat composition.

In certain embodiments, the seal coat composition can also include an amount of an opioid, which can be therapeutically effective in and of itself, as well as the plasticizer and/or the surfactant, as well as other excipients and ingredients such as one or more solvents (both aqueous and organic, e.g., ethanol), as well as other excipients that can also be included in the seal coat composition.

In certain embodiments, the seal coat can be present in a range of about 0.1% to about 40% w/w of the uncoated Opioid Particulates, i.e., the Opioid Particulates before being coated with the (optional) seal coat, the Functional Coat(s), and the over coat. In certain embodiments, the seal coat can be present in a range from about 5% to about 25% w/w of the uncoated Opioid Particulates. In certain embodiments, the seal coat can be present in an amount of about 5% or about 15% w/w of the uncoated Opioid Particulates. In certain embodiments, the seal coat can be present in a range of about 0.2% to about 37.5%, about 0.3% to about 35%, about 0.4% to about 32.5%, about 0.5% to about 30%, about 0.6% to about 27.5%, about 0.7% to about 25%, about 0.8% to about 22.5%, about 0.9% to about 20%, about 1% to about 17.5%, about 2.5% to about 15%, about 5% to about 12.5%, or about 7.5% to about 10% w/w of the total weight of the uncoated Opioid Particulates. In certain embodiments, the seal coat can be present in an amount of at least about 0.1%, at least about 0.2%, at least about 0.5%, at least about 1%, at least about 5%, at least about 10%, at least about 15%, at least about 20%, at least about 25%, at least about 30%, at least about 35%, or at least about 40% w/w of uncoated Opioid Particulates.

2.5. Functional Coat Layers

In certain embodiments, the Opioid Particulates are coated with a functional coat layer(s) (e.g., FC 0, FC 1, and/or FC 2). In certain embodiments, one or more functional coat layers, e.g., FC 1, include a water insoluble nonionic polymer (such as a polymer that is not soluble in physiological fluids and common organic solvents such as ethanol) and a cationic polymer (such as a polymer that is soluble in gastric fluids) that behaves as a pore former at pH below about 5.0.

In certain embodiments, functional coat layer(s) of the Opioid Particulates can comprise at least a water-insoluble nonionic polymer, e.g., cellulose acetate, cellulose acetate-based polymers (e.g. OPADRY® CA, cellulose acetate butyrate, cellulose acetate propionate, and the like), polyvinyl acetate polymers, polyvinyl acetate-based copolymers (e.g., KOLLIDON® SR), ethylcellulose (e.g., ETHOCEL™), EUDRAGIT® RL 100, EUDRAGIT® RL PO, EUDRAGIT® RS 100, EUDRAGIT® RS PO, EUDRAGIT® NE 30 D, EUDRAGIT® NE 40 D, and the like, or a blend thereof; and a pH-dependent, cationic copolymer (e.g., dimethylaminoethyl methacrylate, butyl methacrylate, and methyl methacrylate copolymer (e.g., EUDRAGIT® E PO)).

In certain embodiments, the functional coat layer(s) comprises at least cellulose acetate and a copolymer based on dimethylaminoethyl methacrylate, butyl methacrylate, and methyl methacrylate. In certain embodiments, the dimethylaminoethyl methacrylate, butyl methacrylate, and methyl methacrylate-based copolymer is EUDRAGIT® E PO.

In certain embodiments, cellulose acetate ("CA") and/or CA-based polymer blends, together with the pH-dependent pore former, becomes almost impermeable at a pH greater than about 5.0, thereby reducing drug release. In certain embodiments, the ratio of CA to pore former (i.e., CA:pore former) can be from about 50:50 to about 98:2 wt % ratio, or from about 70:30 to about 98:2 wt % ratio. In certain embodiments, the ratio of CA to pore former can be from about 72.5:27.5 to about 95:5, about 75:25 to about 92.5:7.5, about 77.5:22.5 to about 90:10, about 80:20 to about 87.5: 12.5, or about 82.5:17.5 to about 85:15 wt % ratio. In certain embodiments, the ratio of CA to pore former can be about 71:29, about 72:28, about 73:27, about 74:26, about 75:25, about 76:24, about 77:23, about 78:22, about 79:21, about 80:20, about 81:19, about 82:18, about 83:17, about 84:16, about 85:15, about 86:14, about 87:13, about 88:12, about 89:11, about 90:10, about 91:9, about 92:8, about 93:7 about 94:6 about 95:5, about 96:4, about 97:3, or about 98:2 wt % ratio. In certain embodiments, the ratio of CA to pore former can be about 80:20 wt % ratio.

In certain embodiments, the nonionic water-insoluble polymer is a polyvinyl acetate polymer ("PVA polymer") or a PVA-based polymer or copolymer. In certain embodiments, the PVA-based polymer along with the pH-dependent pore former becomes almost impermeable at pH greater than 5.0, thereby reducing drug release. In certain embodiments, the ratio of PVA-based polymer to pore former (i.e., PVA-based polymer:pore former) can be from about 70:30 to about 98:2 wt % ratio. In certain embodiments, the ratio of PVA-based polymer to pore former can be from about 72.5:27.5 to about 95:5, about 75:25 to about 92.5:7.5, about 77.5:22.5 to about 90:10, about 80:20 to about 87.5:12.5, or about 82.5:17.5 to about 85:15 wt % ratio. In certain embodiments, the ratio of PVA-based polymer to pore former can be about 71:29, about 72:28, about 73:27, about 74:26, about 75:25, about 76:24, about 77:23, about 78:22, about 79:21, about 80:20, about 81:19, about 82:18, about 83:17, about 84:16, about 85:15, about 86:14, about 87:13, about 88:12, about 89:11, about 90:10, about 91:9, about 92:8, about 93:7 about 94:6 about 95:5, about 96:4, about 97:3, or about 98:2 wt % ratio. In certain embodiments, the ratio of PVA-based polymer to pore former can be about 80:20 wt % ratio.

In certain embodiments, if three or more dosage units are taken, release of the opioid from the dosage form is reduced. In certain embodiments, the release is reduced by 25%, 35%, 45%, 55%, 65%, 75%, 85%, 95%, 96%, 97%, 98%, 99%, or increments therein. In certain embodiments, the release is reduced from about 30% to about 90%, about 40% to about 80%, or about 50% to about 70%.

In certain embodiments, the composition of the functional coating can also include an anti-tacking agent (e.g., talc, magnesium trisilicate, colloidal silicon dioxide (e.g., CAB-O-SIL®)) and/or a plasticizer.

In certain embodiments, the functional coating prevents the extraction of the opioid in water and in water/alcohol mixtures.

In certain embodiments, FC 1 can be present in a range of about 5% to about 70% w/w of the uncoated or seal coated Opioid Particulates (e.g., the polymer matrix with an opioid embedded within, also including the optional seal coat, if present). In certain embodiments, the FC 1 can be present in a range of about 10% to about 65%, about 15% to about 60%, about 20% to about 55%, about 25% to about 50%, about 30% to about 45%, or about 35% to about 40% w/w of the uncoated or seal coated Opioid Particulates. In certain embodiments, FC 1 can be present in a range of about 5% to about 10%, about 5.25% to about 9.75%, about 5.5% to about 9.5%, about 5.75% to about 9.25%, about 6% to about 9%, about 6.25% to about 8.75%, about 6.5% to about 8.5%, or about 6.75% to about 8.25% w/w of the uncoated or seal coated Opioid Particulates. In certain embodiments, FC 1 can be present in a range from about 10% to about 35%, or about 15% to about 25% w/w of the uncoated or seal coated Opioid Particulates.

In certain embodiments, the functional coated Opioid Particulates can be further coated with an additional functional coat layer(s) (e.g., FC 2 and/or FC 0) to further enhance ODP features. In certain embodiments, FC 2 and/or FC 0 can comprise a cationic polymer (e.g., EUDRAGIT® E PO). In certain embodiments, FC 2 and/or FC 0 can comprise a cationic polymer and a nonionic polymer.

In certain embodiments, the composition of the FC 2 and/or FC 0 can also include an anti-tacking agent (e.g., talc, magnesium trisilicate, colloidal silicon dioxide (e.g. CAB-O-SIL®)) and/or a plasticizer.

In certain embodiments, Opioid Particulates can comprise one, two, or three functional coat layer(s) (e.g., FC 1, or FC 1 and FC 0 and/or FC 2). In certain embodiments, Opioid Particulates can comprise more than three functional coat layers (e.g., four or five functional coat layers). In certain embodiments, any one or more of the functional coat layers can comprise a cationic polymer(s) in the absence of a water-insoluble nonionic polymer. In certain embodiments, any one or more of the functional coats can comprise a cationic polymer(s) in the presence of a water-insoluble nonionic polymer; in such embodiments, the ratio of nonionic polymer to cationic polymer can be from about 0.1:99.9 to about 99.9:0.1.

2.6. Over Coat

In certain embodiments, the functional coated Opioid Particulates (i.e., with or without FC 2) include an over coat to prevent/minimize the interaction of EUDRAGIT® E PO (e.g., in FC 1 and/or FC 2) with the alkaline agent present in the Triggering Particulates. The over coat can include a nonionic polymer (e.g., hydroxypropyl methylcellulose).

In certain embodiments, the composition of the over coat can also include additional excipients such as an anti-tacking agent (e.g., talc, magnesium trisilicate, colloidal silicon dioxide (e.g., CAB-O-SIL®)) and a plasticizer; the plasticizer can be the same as or different from the plasticizer(s) that can be present in Opioid Particulates.

In certain embodiments, the over coat can be present in a range of about 5% to about 50% w/w of the functional coated Opioid Particulates (i.e., the polymer matrix with an opioid embedded within, (optional) seal coat, and one or more functional coat layers). In certain embodiments, the over coat can be present in a range of about 10% to about 50%, about 10% to about 45%, about 10% to about 35%, about 10% to about 30%, about 15% to about 40%, about 15% to about 25%, about 20% to about 35%, or about 25% to about 30% w/w of the functional coated Opioid Particulates.

2.7. Crush and Extractability Resistance

In certain embodiments, the Opioid Granules are at least partially crush-resistant, nongrindable, and nonextractable. In certain embodiments, they are substantially noncrushable, nongrindable, and nonextractable, thereby making the opioid difficult to abuse. For example, the Opioid Granules resist abuse via, but not limited to, crushing and swallowing; crushing and insufflating/inhaling nasally ("snorting"); crushing and smoking; or crushing, dissolving, and injecting (subcutaneously (i.e., skin popping), intravenously, or intramuscularly). In certain embodiments, the Opioid Granules cannot be ground or crushed into particles small enough to be effectively snorted or injected. In certain embodiments, the Opioid Granules cannot be pulverized into fine powder by mechanical grinding.

The crush-resistance of the Opioid Granules can be determined by a measurement of crushing strength required to deform the granules without any evidence of fragmentation, or breaking into smaller pieces or powder using an Instron Tester or equivalent. In some embodiments, the Opioid Granules can withstand a crushing strength ranging from 300-1000 N. Abuse deterrence can be tested by examining the mean particle size following the physical and/or mechanical manipulation, with or without thermal pretreatment, of the Opioid Granule. For example, the Opioid Granules can be subjected to grinding/crushing in a coffee grinder, mill, mortar and pestle, a food processor, a blender, etc. For example, Opioid Granules can be placed in a coffee grinder (e.g., Hamilton Beach Coffee Grinder) and ground for several cycles (e.g., at a 10 cup setting for 8 cycles of 30 seconds each).

The mean particle size of the granules after grinding can be measured using sieve analysis that gathers granules of the same size into groups based on particle size. The weight of the particles in each group can be measured and compared to an unground sample.

In certain embodiments, the mean particle size after grinding the Opioid Granules is about 500 µm (with a range of about 250 µm to about 1000 µm), as measured by weight frequency distribution using sieving method. In certain embodiments, the mean particle size after grinding the Opioid Granules is greater than about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 475 µm, about 500 µm, about 525 µm, about 550 µm, about 575 µm, about 600 µm, about 625 µm, about 650 µm, about 675 µm, or about 700 µm.

Abuse deterrence can be tested by examining the syringeability of the Opioid Granules either before or after grinding. For example, syringeability can be tested by examining the difficulty of drawing a solution of the dosage form, dissolved in varying types of solvents (e.g., water) and volumes of solvent (e.g., 2-10 ml) through, e.g., an 18 gauge syringe needle. The syringeability can also be tested by determining the amount of active ingredient present in the withdrawn liquid.

Abuse deterrence can also be tested by examining the extractability of opioid from the Opioid Granules before and after grinding.

3. Triggering Particulates

In certain embodiments, the Triggering Particulates can be Triggering Granules. In certain embodiments, the Triggering Granules can contain a combination of at least one alkaline agent (e.g., magnesium hydroxide (increases pH from 1.6 to greater than 5.0)) and/or at least one pH-stabilizing agent (e.g., di- and/or tricalcium phosphate (maintains the elevated pH of greater than 5.0 for up to about 30 minutes, about one hour, or about two hours)). In certain embodiments, ingestion of one dosage unit (e.g., one tablet or capsule) results in little or no increase in pH of the gastric fluids. In certain embodiments, ingestion of multiple dosage units (e.g., three or more) results in the alkaline agent increasing the pH very rapidly above about 5.0. In certain embodiments, the pH-stabilizing agent acts to maintain or stabilize the increased pH caused by the alkaline agent. For example, ingestion of multiple dosage units results in (a) a rapid increase in pH caused by the alkaline agent; (b) modulation of pore formation in the functional coat; and (c) a decrease in the rate of release of the opioid from the Opioid Particulate. In certain embodiments, upon ingestion of multiple dosage units (e.g., three or more), the pH of the gastric fluid increases very rapidly above a pH of about 5.0 (e.g., in about one to about five minutes). In certain embodiments, the increase in the pH of the gastric fluid upon taking multiple dosage units occurs in about two to about three minutes.

In certain embodiments, the alkaline agent for use in the Triggering Granules include, but are not limited to, aluminum hydroxide, sodium hydroxide, potassium hydroxide, calcium hydroxide, magnesium hydroxide, calcium carbonate, sodium carbonate, potassium bicarbonate, sodium bicarbonate, sodium oxide, calcium oxide, magnesium oxide, aluminum oxide, potassium oxide, ammonia, tertiary sodium phosphate, diethanolamine, ethylenediamine, N-methylglucamine, L-lysine, and combinations thereof. In certain embodiments, the alkaline agent is magnesium hydroxide.

In certain embodiments, the alkaline agent is present in an amount that when a single dosage unit is taken, it does not alter the pH of the gastric fluid. In certain embodiments, the alkaline agent is present in an amount from about 30% to about 90% w/w of total Triggering Granules. In certain embodiments, the alkaline agent is present in an amount from about 35% to about 85%, about 40% to about 80%, about 45% to about 75%, about 50% to about 70%, or about 55% to about 65% w/w of total Triggering Granule. In certain embodiments, the alkaline agent is present in an amount from about 40% to about 70%, about 70% to about 90%, or about 50% to about 60%, w/w of the total Triggering Granule.

In certain embodiments, the pH-stabilizing agents for use in the Triggering Granules include, but are not limited to, bismuth aluminate, bismuth carbonate, bismuth subcarbonate, bismuth subgallate, bismuth subnitrate, calcium phosphate, dibasic calcium phosphate, dihydroxyaluminum aminoacetate, dihydroxyaluminum glycine, magnesium glycinate, sodium potassium tartrate, tribasic sodium phosphate, tricalcium phosphate, and combinations thereof. In certain embodiments, the pH-stabilizing agent is a combination of dibasic calcium phosphate/tricalcium phosphate. In certain embodiments, the ratio of dibasic calcium phosphate to tricalcium phosphate (i.e., dibasic calcium phosphate:tricalcium phosphate) is about 1:1 to about 1:5 wt % ratio. In certain embodiments, the ratio of dibasic calcium phosphate to tricalcium phosphate is about 1:1.25 to about 1:4.75, about 1:1.5 to about 1:4.5, about 1:1.75 to about 1:4.25, about 1:2 to about 1:4, about 1:2.25 to about 1:3.75, about 1:2.5 to about 1:3.5, or about 1:2.75 to about 1:3.25 wt % ratio. In certain embodiments, the pH-stabilizing agent is anhydrous dibasic calcium phosphate.

In certain embodiments, the pH-stabilizing agent is present in an amount that when a single dosage unit is taken, it does not alter the pH of the gastric fluid, but when multiple dosage units are taken (e.g., three or more dosage units), the pH-stabilizing agent maintains the elevated pH levels caused by the alkaline agent. In certain embodiments, the pH-stabilizing agent is present in an amount sufficient to maintain or stabilize the pH of the gastric fluid above about 5.0 for up to five hours. In certain embodiments, the pH-stabilizing agent is present in an amount sufficient to maintain the pH of the gastric fluid above about 5.0 for about one to about two hours. In certain embodiments, the pH-stabilizing agent is present in an amount sufficient to maintain the pH of the gastric fluid above about 5.0 for at least about 1 hour, at least about 1.25 hours, at least about 1.5 hours, at least about 1.75 hours, at least about 2 hours, at least about 2.25 hours, at least about 2.5 hours, at least about 2.75 hours, at least about 3 hours, at least about 3.25 hours, at least about 3.5 hours, at least about 3.75 hours, at least about 4 hours, at least about 4.25 hours, at least about 4.5 hours, at least about 4.75 hours, at least about 5 hours.

In certain embodiments, the pH-stabilizing agent is present in an amount from about 10% to about 60% w/w of total Triggering Granules. In certain embodiments, the pH-stabilizing agent is present in an amount from about 12.5% to about 57.5%, about 15% to about 55%, about 17.5% to about 52.5%, about 20% to about 50%, about 22.5% to about 47.5%, about 25% to about 45%, about 27.5% to about 42.5%, about 30% to about 40%, or about 32.5% to about 37.5% w/w of total Triggering Granules. In certain embodiments, the pH-stabilizing agent is present in an amount from about 15% to about 40%, or about 20% or about 30%, w/w of total Triggering Granules.

In certain embodiments, the alkaline agent and the pH-stabilizing agent (combined) (e.g., included in the Triggering Particulates) are present in an amount of less than 60% w/w (i.e., 60 wt %) of the total dosage form (or pharmaceutical composition). In certain embodiments, the alkaline agent and the pH-stabilizing agent (combined) are present in an amount of less than 60%, less than 55%, less than 50%, less than 45%, less than 44%, less than 43%, less than 42%, less than 41%, less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, or less than 15%, w/w of the total dosage form.

In certain embodiments, the Triggering Granules include a binder, a disintegrant, filler (or diluents), and/or a lubricant.

Binders according to the presently disclosed subject matter include, but are not limited to, hydroxypropyl celluloses in various grades, hydroxypropyl methylcelluloses in various grades, polyvinylpyrrolidones in various grades, copovidones, powdered acacia, gelatin, guar gum, carbomers, methylcelluloses, polymethacrylates, and starches.

Disintegrants according to the presently disclosed subject matter include, but are not limited to, carmellose calcium, carboxymethylstarch sodium, croscarmellose sodium, crospovidone (crosslinked homopolymer of N-vinyl-2-pyrrolidone), low-substituted hydroxypropyl celluloses, sodium starch glycolate, colloidal silicon dioxide, alginic acid and alginates, acrylic acid derivatives, and various starches.

Lubricants according to the presently disclosed subject matter include, but are not limited to, magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

The Triggering Granules can be prepared by any granulation method known to those of skill in the art. For example, the Triggering Granules can be made by dry granulation (e.g., direct blend, compacting and densifying the powders), wet granulation (e.g., addition of a granulation liquid onto a powder bed under the influence of an impeller or air), or hot melt extrusion (HME). The granulation product obtained can be milled to achieve uniform granules. The granules obtained can be subsequently coated with an aqueous dispersion.

In certain embodiments, the mean particle size distribution of the Triggering Granules is about 100 μm to about 1000 µm. In certain embodiments, the mean particle size distribution of the Triggering Granules is about 150 µm to about 950 µm, about 200 µm to about 900 µm, about 250 µm to about 850 µm, about 300 µm to about 800 µm, about 350 µm to about 750 µm, about 400 µm to about 700 µm, about 450 µm to about 650 µm, or about 500 µm to about 600 µm. In certain embodiments, the mean particle size distribution of Triggering Granules is about 300 µm to about 800 µm.

4. Naloxone Particulates

Naloxone (a semi-synthetic N-allyl derivative of oxymorphone) is a potent competitive opiate antagonist at µ, κ, and δ receptors in both the central and peripheral nervous system; with strongest affinity to the µ-opioid receptor and weaker affinity to the κ- and δ-opioid receptors. Naloxone is a narcotic antagonist that blocks the effect of narcotics and can cause severe narcotic withdrawal when injected.

Naloxone has little effect when taken by mouth. The effects of opioids on gastrointestinal motility and transit are thought to be predominantly mediated by the µ-opioid receptors. When administered orally, naloxone can reduce opioid-induced constipation (OIC) via competitive antagonism at µ-opioid receptors in the gut wall. In the human gut, µ-opioid receptors are present in the enteric nervous system (ENS), i.e., in the submucosal and myenteric plexus. Thus, naloxone can act at the µ-opioid receptors after absorption from the gut lumen into the enteric tissues before entering the systemic circulation. Although, naloxone is rapidly and readily absorbed (75%) from the GI tract it undergoes extensive intestinal and hepatic first-pass metabolism, mainly by glucuronide conjugation, with naloxone-3-glucuronide being the major inactive metabolite. Naloxone also undergoes N-dealkylation and reduction of the 6-keto group, followed by conjugation. The drug is almost completely metabolized by the liver before reaching the systemic circulation resulting in an oral bioavailability of 2-3% after intake of therapeutic doses allowing antagonism of gastrointestinal opioid receptors and thus helps in reducing OIC. The minute portion of a small dose of naloxone that reaches the systemic circulation and crosses the blood-brain barrier is too small to precipitate any anti-analgesic effects.

Solid oral dosage form of the presently disclosed subject matter comprising a combination of an opioid (e.g., an opioid agonist) and an opioid antagonist (e.g., naloxone) is a complete treatment program for drug abuse that can prevent, inhibit, reduce, or delay the effects of an opioid overdose. In certain embodiments of the presently disclosed subject matter, naloxone is present in the pharmaceutical composition as a free base or as a pharmaceutically acceptable salt. In certain embodiments, Naloxone Particulates comprise naloxone in a free base form or in the form of a pharmaceutically acceptable salt, e.g., naloxone hydrochloride. In certain embodiments, Naloxone Particulates comprise naloxone in an amount, when three or more dosage units are consumed, that is sufficient to cross the blood-brain barrier, displace opioids from the opioid receptors, and block the binding of opioids (e.g., additional amounts of opioids) for 20-90 minutes.

Patients who do not intentionally or unintentionally abuse their opioid medication would receive no apparent benefit from a sequestered opioid agonist-antagonist combination. Naloxone present in the solid oral dosage form of the presently disclosed subject matter, because of its reduced bioavailability, does not act as an antagonist when one or two dosage units are consumed. However, in the event of overdose, e.g., three or more dosage units being consumed together (including, but not limited to, simultaneously, in tandem, serially in a relatively short span of time), a pharmacologically effective amount of naloxone is available from the dosage units to bind with the opioid receptors and block the binding of additional opioids for 20-90 minutes. In one embodiment of the presently disclosed subject matter, the pharmacologically effective amount is the amount of naloxone in blood that is comparable to the amount in the blood when administered as an IV or IM injection in a clinical setting to overcome the effects of an overdose. In certain embodiments, a pharmacologically effective amount of naloxone is not present in the blood when one or two dosage units are consumed, i.e., there is insufficient naloxone present to cross the blood-brain barrier and bind with sufficient µ-receptors.

In certain embodiments, the pharmacologically effective amount of naloxone hydrochloride comprises about 0.55 to about 3 ng/ml plasma concentration. In certain embodiments, the pharmacologically effective amount of naloxone hydrochloride comprises about 0.6 to about 2.5 ng/ml plasma concentration. In certain embodiments, the pharmacologically effective amount of naloxone hydrochloride comprises about 0.7 to about 2 ng/ml plasma concentration. In certain embodiments, the pharmacologically effective amount of naloxone hydrochloride comprises about 0.8 to about 1 ng/ml plasma concentration. In certain embodiments, the pharmacologically effective amount of naloxone hydrochloride comprises about 0.88 ng/ml plasma concentration.

In certain embodiments, the mean particle size distribution of the Naloxone Particulates can be from about 100 µm to about 1500 µm (1.5 mm), and in some embodiments from about 250 µm to about 750 µm (as measured by weight frequency distribution using sieving method). In certain embodiments, the mean particle size of the Naloxone Particulates is about 400 µm to about 600 µm. In certain embodiments, the mean particle size of the Naloxone Particulates is about 500 µm.

In certain embodiments, naloxone does not behave as an antagonist when the dosage form is consumed as intended, e.g., one or two dosage units being consumed. In certain embodiments, naloxone behaves as opioid antagonist, when three or more dosage units are consumed. Naloxone provides built-in overdose protection because naloxone is minimally bioavailable with oral ingestion and the amount of naloxone present in two or less dosage forms is not enough to provide a pharmacologically effective amount that can reverse opioid effects.

In certain embodiments, the presently disclosed subject matter provides an oral IR multi-particulate dosage form comprising an opioid agonist, e.g., oxycodone hydrochloride, and an opioid antagonist, e.g., naloxone hydrochloride, wherein naloxone hydrochloride shows dose-dependent bioavailability. The bioavailability of naloxone hydrochloride increases when multiple units, e.g., three dosage forms units or more, of the opioid agonist/antagonist combinations are consumed/administered. The nonlinearity of bioavailability is most probably due to saturation of first-pass metabolism, resulting in higher plasma naloxone concentration achieved when three or more dosage units are consumed (as opposed to when two or less dosage units are consumed). In certain embodiments, the presently disclosed subject matter provides an oral immediate release pharmaceutical dosage form comprising oxycodone hydrochloride and naloxone hydrochloride, wherein naloxone hydrochloride is present in an amount such that two or less dosage units do not provide a pharmacologically effective amount of naloxone to reverse the effects of the administered opioids.

5. Enteric Coated Naloxone Particulates

In certain embodiments, the presently disclosed subject matter provides an oral immediate release pharmaceutical composition comprising oxycodone hydrochloride and enteric coated naloxone hydrochloride in about 2:1 ratio with oxycodone hydrochloride being present in an amount of about 2.5 mg to about 20 mg and with naloxone hydrochloride being present in an amount of about 1.25 mg to about 10 mg. In certain embodiments, the enteric coated naloxone hydrochloride improves bioavailability of naloxone by providing a reservoir/bolus of naloxone in the intestine to saturate the first-pass metabolism, thereby providing a reservoir of unmetabolized naloxone in plasma. This saturation of first-pass metabolism provides a higher plasma concentration of naloxone (i.e., improves bioavailability of naloxone).

In certain embodiments, the presently disclosed subject matter provides an oral immediate release pharmaceutical dosage form comprising Opioid Particulates comprising oxycodone hydrochloride and enteric coated Naloxone Particulates comprising naloxone hydrochloride, wherein naloxone hydrochloride is not co-released with oxycodone hydrochloride when one or two dosage units are consumed, i.e., there is a time lag between the release of oxycodone hydrochloride and naloxone hydrochloride; oxycodone hydrochloride is released in the acidic environment of the stomach, and naloxone hydrochloride is released sometime later in the less acidic/more basic environment of the small intestine.

In certain embodiments, the presently disclosed subject matter provides an oral immediate release pharmaceutical composition comprising Opioid Particulates comprising oxycodone hydrochloride and enteric coated Naloxone particulates comprising naloxone hydrochloride, wherein naloxone hydrochloride is co-released with at least a portion of oxycodone hydrochloride when three or more dosage units are consumed. In other words, the increased pH of the stomach environment associated with the alkaline agent present in three or more dosage units is responsible for a decrease in release of opioid from reverse-enteric (acid-labile) coated Opioid Particulates; the same environment also provides an increase in release of naloxone hydrochloride from enteric ("alkaline-labile") coated Naloxone Particulates. This change in the ratio of released oxycodone to released naloxone reaching the small intestine for absorption will result in pharmacologically effective blockade of central opioid receptors by naloxone, and will add to the decreased opioid effects resulting from the acid-labile coating of the Opioid Particulates.

6. Lipid-Based Naloxone Particulates and ASDs of Naloxone

In certain embodiments, formulations of lipid-based compositions or amorphous solid dispersions of naloxone are provided. In other embodiments, the lipid based formulations avoid first-pass metabolism of naloxone and improve naloxone solubility. Naloxone can be contained in Naloxone Particulates with the following features.

6.1. Lipid Excipients

In certain embodiments, opioid agonist and antagonist formulations (e.g., combined opioid and naloxone formulations) contain oral, immediate release, lipid-based naloxone compositions with enhanced oral bioavailability. In certain embodiments, the choice of excipients for lipid-based naloxone compositions depend upon various factors comprising miscibility, solvent capacity, self-dispersibility, and ability to promote self-dispersion of the formulation; digestibility and fate of digested products; regulatory issues, such as irritancy, toxicity, and chemical stability; capsule compatibility; and melting point. In certain embodiments, lipid-based naloxone compositions comprise dietary oils composed of long-chain fatty acids, and medium- and long-chain triglycerides, along with various solvents and surfactants. Table A provides a list of commonly used solubilizing agents in lipid-based naloxone compositions.

TABLE A

Solubilizing Agents in Lipid-based Formulations

| Water-insoluble Excipients | Triglycerides | Surfactants |
| --- | --- | --- |
| Bees wax | Long-chain triglycerides | Polysorbate 20 (Tween 20) |
| Oleic acid | Soy lecithin | Polysorbate 80 (Tween 80) |
| Soy oil | Vegetable oil | Sorbitan monolaurate (Span 20) |
| D-α-tocopherol | Olive oil | D-α-tocopherol PEG 1000 succinate (TPGS) |
| Corn oil mono- and diglycerides | Soybean oil | Polyoxyl 35 castor oil (Cremaphor EL) |
| Medium chain (C8/C10) mono- and diglycerides | Peanut oil | Polyoxyl 40 hydrogenated castor oil |
| Propylene glycol esters of fatty acids | | PEG 300 Oleic glycerides |
| | Medium-chain triglycerides | PEG 300 Linoleic glycerides |
| | Caprylic/capric triglycerides | PEG 400 caprylic/capric glycerides |
| | | PEG 1500 lauric glycerides |

The most common excipients used in lipid-based naloxone compositions are triglyceride vegetable oils. Triglycerides are classified as long-chain triglycerides (LCT), medium-chain triglycerides (MCT), and short-chain triglycerides (SCT). MCTs have a higher solvent capacity than LCTs and are less prone to oxidation. MCTs improve solvent capacity and dispersibility of the formulation. Pure triglycerides are found in refined vegetable oils.

In certain embodiments, the lipid-based naloxone compositions include, but are not restricted to, MCTs and LCTs.

In certain embodiments, MCTs include caprylic/capric triglyceride, e.g., MIGLOYL® 812 and LABRAFAC 1349.

In certain embodiments, lipid-based compositions of naloxone, suitable for oral administration, include LCTs. In certain embodiments, LCTs include castor oil, soy oil, soy lecithin, peanut oil, vegetable oil, and olive oil.

In certain embodiments, lipid-based compositions of naloxone suitable for oral administration include long-chain fatty acids. In certain embodiments, the long-chain fatty acids include, but are not limited to, ricinoleic acid, sesame oil, corn oil, and oleic acid.

6.2 Medium-Chain Mixed Triglycerides (Polar Oily Excipients)

Medium-chain mixed triglycerides are obtained by partial hydrolysis of vegetable oils. The starting material (LCTs) and the extent of hydrolysis determine the chemical composition of the mixed triglycerides. Medium-chain mixed triglycerides (polar oily excipients) are not susceptible to oxidation, have greater solvent capacity, and promote emulsification. These polar oily excipients improve solvent capacity and dispersibility of the drug. In certain embodiments, the dispersions contain naloxone. In certain embodiments, the naloxone dispersions can be used for coating a solid carrier.

6.3. Cosolvents

In certain embodiments, lipid based Naloxone Particulates comprise at least one cosolvent to enhance solubilization of naloxone in lipids. In certain embodiments, the cosolvents include isopropyl alcohol, ethanol, acetone, benzyl alcohol, propylene glycol, and polyethylene glycol (PEG-400). In certain embodiments, other edible co-solvents are also used. In certain embodiments, the cosolvents are used to enhance solvent capacity of the composition for naloxone and to aid the dispersion of systems that contain a high proportion of water-soluble surfactants.

6.4. Antioxidants

In certain embodiments, lipid based Naloxone Particulates comprise at least one antioxidant. In certain embodiments, the antioxidant helps in modulating the solubility of naloxone. Antioxidants of the presently disclosed subject matter include, but are not limited to, ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. In certain embodiments, the tocopherol is dl-α-tocopherol.

6.5. Surfactants

In certain embodiments, lipid based Naloxone Particulates comprise at least one surfactant. In certain embodiments, pharmaceutically acceptable surfactants include soluble in oils, cosolvents, or aqueous media. In certain embodiments, the surfactant component helps in modulating the solubility of naloxone. In certain embodiments, the surfactant helps to reduce the abuse potential of the opioid in a combined opioid and naloxone dosage form by dual mechanisms. First, surfactants elicit an irritant response when administered "as is" by nasal or injection routes; second, surfactants elicit an irritant response by co-eluting with the opioid when extracted with commonly used solvents, such as aqueous and organic solvents. Surfactants produce tissue irritation when applied to nasal mucosa and will cause local irritation at an injection site. The hydrophilic-lipophilic balance ("HLB") values of the surfactants are in a range of about 4 to about 30.

Further, with regard to one particular surfactant, docusate sodium (which is commonly used as a stool softener/laxative, thus providing some relief for opioid-induced constipation at the intended dose), can cause undesirable gastrointestinal effects if large quantities are ingested. Similar gastrointestinal effects can be obtained by ingesting other surfactants. In certain embodiments, the surfactant is present in an amount that results in discomfort to the abuser when the surfactant is co-eluted with the opioid.

Surfactants of the presently disclosed subject matter include nonionic surfactants (e.g., esters of fatty acids, especially of C8-C24, and fatty acid esters of polyols such as glycerol or sorbitol); sorbitan fatty acid esters ethoxylated with from 2 to 30 moles of ethylene oxide; polyethylene glycol fatty acid esters; polyethyleneglycol esters and polyethyleneglycol ethers; and polyethoxylated carboxylic acids (e.g., PEG-35 castor oil, PEG-40 castor oil, steareth-2 (e.g., Brij 72, Uniqema), steareth-21 (e.g., Brij 721, Uniqema), ceteareth-25 (e.g., Cremophor A25, BASF Cooperation), PEG-7 hydrogenated castor oil (e.g., Cremophor WO7, BASF Cooperation), and PEG-30 dipolyhydroxystearate (e.g., Arlacel P 135, Uniqema)); block copolymers based on ethylene oxide and propylene oxide (e.g., PLURONIC® (e.g., 188 or 407 (BASF)); dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; and polyoxyl 40 stearate. Anionic surfactants (e.g., alkyl ether sulfates and sulfosuccinates) can also be useful. Alternatively, cationic and amphoteric surfactants such as phospholipids, lysophospholipids, and PEGylated phospholipids can also be used. Additional useful surfactants include, vitamin E and derivatives thereof (e.g., PEGylated derivatives of vitamin E such as tocopherol PEG succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate, and tocotrienol polyethylene glycol phthalate; see, e.g., U.S. Pat. No. 9,351,517, hereby incorporated-by-reference herein in its entirety).

6.6. Extrusion Spheronization

In certain embodiments, a liquid lipid composition of naloxone is adsorbed onto a solid substrate/carrier. Naloxone is first dispersed/dissolved in a liquid carrier, e.g., lipid, and optionally a co-solvent, and then sprayed onto a substrate/carrier (e.g., microcrystalline cellulose, or SYLOID®). To the resulting blend, a sufficient amount of water is added until a mass suitable for extrusion is obtained. The pellets obtained from extrusion are dried overnight at a temperature of about 40° C. In certain embodiments, the solid carrier/substrate comprises a carrier/substrate and an encapsulation coat on the carrier/substrate. In certain embodiments, the encapsulation coat includes at least one ionic or nonionic surfactant. In certain embodiments, the encapsulation coat includes naloxone, and a lipophilic component, e.g. a lipophilic surfactant and/or lipid. In certain embodiments, the lipophilic component comprises one or more lipid surfactants. In certain embodiments, the substrate includes silicon dioxide, calcium silicate, magnesium silicate, sugar spheres, and microcrystalline cellulose. In certain embodiments, the liquid lipid composition of naloxone is added to the carrier by mixing in a granulator (e.g., adsorbed on the carrier). In certain embodiments, the carrier is selected such that it has the ability to adsorb the liquid lipid composition of naloxone and have good flow properties after adsorption.

6.7. Melt Granulation

In certain embodiments, Naloxone Particulates comprise pellets/granules containing naloxone and at least one lipid in the pellet/granule core. In certain embodiments, the pellets comprising naloxone and at least one lipid are made by direct pelletization using melt-granulation. In certain embodiments, melt granulation comprises mixing naloxone with a molten lipid to form a dispersion; heating the dispersion to dissolve naloxone; and cooling the resulting clear solution to form a solid dispersion. In certain embodiments, the solid dispersion is taken in a solvent and sprayed onto carrier/substrate (e.g., SYLOID® XDP, cellets, or pellets made by extrusion spheronization). In certain embodiments, the carrier comprises anionic polymers, cationic polymers, nonionic polymers, or mixtures thereof. In certain embodiments, anionic polymers include, but are not limited to, EUDRAGIT® L100, EUDRAGIT L®100-55, EUDRAGIT® S100, hydroxypropyl methylcellulose acetate succinate (HPMCAS), hydroxypropyl methylcellulose phthalate (HPMCP), cellulose acetate phthalate (CAP), CARBOPOL® and polyvinyl acetate phthalate. Representative cationic polymers include, but are not limited to, (meth)acrylic polymers and (meth)acrylic copolymers (e.g., copolymers of alkyl (meth)acrylates and copolymers of alkylamino(meth)acrylates); and quaternary ammonium (meth)acrylic polymers. Representative nonionic polymers include, but are not limited to, a nonionic copolymer of ethyl acrylate, methyl methacrylate and a low content of methacrylic acid ester with quaternary ammonium groups (ammonium methacrylate copolymer, Type A, NF) (e.g., EUDRAGIT® RL 100, RS100 (Evonik)); and nonionic polymers such as hydroxypropyl cellulose (e.g., KLUCELE®, L, J, G, M and H grades (Ashland)), hydroxypropyl methylcellulose (HPMC) (e.g., METHOCEL® E, F, J, and K (Dow Chemicals)), hydroxyethyl cellulose (e.g., NATRASOL L, G, M, and H grades (Ashland)), ethylcellulose (e.g., ETHOCEL® 7FP, 10FP, 45FP, and 100FP (Dow Chemicals) and N7, N10, N14, N22, N50, and N100 grades (Ashland)), cellulose acetate butyrate (e.g., CAB-381-0.5 (Eastman)), and cellulose acetate (CA-398-3, CA-398-6, CA-398-100, and CA-398-30 (Eastman)); polyvinyl acetate polymers (e.g., polyvinyl acetate-polyvinylpyrrolidone (Kollidon SR) and polyethylene oxide polymers (e.g., Polyox® WSR coagulant, Polyox® WSR-301, Polyox® WSR-303).

In certain embodiments, lipids include, but are not limited to, polyoxyglycerides (e.g., LABRASOL®), mixed glycerides (mixture of monoglycerides, e.g., CAPMUL® PG 8, diglycerides, e.g., CAPMUL® MCM, and/or triglycerides), partial glycerides (e.g., monoglycerides and diglycerides), polysorbates, and lecithins.

In certain embodiments, Naloxone Particulates are made by dry granulation, wet granulation, top spray granulation, hot-melt extrusion, extrusion spheronization, or rotor granulation.

6.8. Naloxone Amorphous Solid Dispersions (ASDs)

In certain embodiments, a lipid composition of naloxone is an amorphous solid dispersion (ASD). In certain embodiments, the ASD comprises anionic polymers, nonionic polymers, or mixtures thereof. In certain embodiments, anionic polymers include, but are not limited to, EUDRAGIT® L100, EUDRAGIT® L100-55, EUDRAGIT® S100, hydroxypropyl methylcellulose acetate succinate (HPMCAS), hydroxypropyl methylcellulose phthalate (HPMCP), cellulose acetatephthalate (CAP), CARBOPOL,® and polyvinyl acetate phthalate. Representative nonionic polymers include, but are not limited to, hydroxypropyl cellulose (e.g., KLUCELE®, L, J, G, M and H grades (Ashland)), hydroxypropyl methylcellulose (HPMC) (e.g., METHOCEL® E, F, J, and K (Dow Chemicals)), hydroxyethyl cellulose (e.g., NATRASOL L, G, M, and H grades (Ashland)), polyvinyl caprolactam-polyvinyl acetate-polyethylene glycol graft polymer, and polyvinyl acetate polymers (e.g., polyvinyl acetate-polyvinylpyrrolidone polymer matrix (Kollidon SR).

In certain embodiments, a naloxone ASD is made by dissolving naloxone, Kollidon VA 64/HPMCAS-LF/Eudragit L100 and vitamin E-TPGS in acetone or an acetone/water mixture (solvent) and removing the solvent. In certain embodiments, the naloxone ASD is coated onto a solid substrate/carrier by a drug layering process. In certain embodiments, drug layering involves depositing the naloxone ASD dispersion on the surface of a substrate/carrier. In certain embodiments, the carrier comprises anionic polymers, cationic polymers, nonionic polymers, or mixtures thereof. In certain embodiments, anionic polymers include, but are not limited to, EUDRAGIT® L100, EUDRAGIT L®100-55, EUDRAGIT® S100, hydroxypropyl methylcellulose acetate succinate (HPMCAS), hydroxypropyl methylcellulose phthalate (HPMCP), cellulose acetate phthalate (CAP), CARBOPOL® and polyvinyl acetate phthalate. Representative cationic polymers include, but are not limited to, (meth)acrylic polymers and (meth)acrylic copolymers (e.g., copolymers of alkyl (meth)acrylates and copolymers of alkylamino(meth)acrylates); and quaternary ammonium (meth)acrylic polymers. Representative nonionic polymers include, but are not limited to, a nonionic copolymer of ethyl acrylate, methyl methacrylate and a low content of methacrylic acid ester with quaternary ammonium groups (ammonium methacrylate copolymer, Type A, NF) (e.g., EUDRAGIT® RL 100, RS100 (Evonik)); and nonionic polymers such as hydroxypropyl cellulose (e.g., KLUCELE®, L, J, G, M and H grades (Ashland)), hydroxypropyl methylcellulose (HPMC) (e.g., METHOCEL® E, F, J, and K (Dow Chemicals)), hydroxyethyl cellulose (e.g., NATRASOL L, G, M, and H grades (Ashland)), ethylcellulose (e.g., ETHOCEL® 7FP, 10FP, 45FP, and 100FP (Dow Chemicals) and N7, N10, N14, N22, N50, and N100 grades (Ashland)), cellulose acetate butyrate (e.g., CAB-381-0.5 (Eastman)), and cellulose acetate (CA-398-3, CA-398-6, CA-398-100, and CA-398-30 (Eastman)); polyvinyl acetate polymers (e.g., polyvinyl acetate-polyvinylpyrrolidone (Kollidon SR) and polyethylene oxide polymers (e.g., Polyox® WSR coagulant, Polyox® WSR-301, Polyox® WSR-303). In certain embodiments, the naloxone ASD is coated onto cellets using a Wurster fluid bed coater with an inlet air temperature of 40-50° C. and sufficient air volume for fluidization, and the resulting naloxone-layered cellets (i.e., Naloxone Particulates) are dried and, optionally, coated with a seal coat, a functional coat, and/or an over coat.

In certain embodiments, the naloxone ASD is made by hot-melt extrusion, spray drying, micro-bulk precipitation (MBP), pH-controlled precipitation, or solvent controlled precipitation.

6.9 Seal Coat

In certain embodiments, the Naloxone Particulates can be seal coated. In certain embodiments, the seal coat can be disposed between the polymer matrix core (i.e., the polymer matrix with naloxone and lipid embedded within) and a functional coat layer. In certain embodiments, the seal coat can be disposed between the solid substrate/carrier coated/layered with liquid lipid composition of naloxone and a functional coat layer. In certain embodiments, the seal coat can be made with a nonionic water-soluble polymer. In certain embodiments, the nonionic water-soluble polymer that can be included in the seal coat comprises hydroxypropyl cellulose, methyl cellulose, polyvinyl pyrrolidone, copolymers of vinyl pyrrolidone and vinyl acetate, and mixtures thereof. In certain embodiments, the nonionic water-soluble polymer that can be included in the seal coat is a cellulose ether polymer (e.g., a water-soluble methylcellulose and/or hydroxypropyl methylcellulose polymer). In certain embodiments, the amount of the polymer ranges from about 5% to about 100%; from about 30% to about 95%; or from about 50% to about 75% w/w of the total weight of the composition of the seal coat (also noted within as "seal coat composition"). In certain embodiments, the amount of the polymer ranges from about 10% to about 95%, from about 15% to about 90%, from about 20% to about 85%, from about 25% to about 80%, from about 30% to about 75%, from about 35% to about 70%, from about 40% to about 65%, from about 45% to about 60%, or from about 50% to about 55% w/w of the total weight of the seal coat composition.

In certain embodiments, the composition of the seal coat can also include additional excipients, such as an anti-tacking agent (e.g., talc, magnesium trisilicate, colloidal silicon dioxide (e.g., CAB-O-SIL®)), a surfactant, and/or a plasticizer.

In certain embodiments, the seal coat can be present in a range of about 0.1% to about 40% w/w of the uncoated Naloxone Particulates, i.e., the Naloxone Particulates before being coated with the (optional) seal coat. In certain embodiments, Naloxone Particulates do not include a seal coat.

6.10. Functional (Enteric) Coat

In certain embodiments, the lipid-based Naloxone Particulates are coated with at least one functional coat layer. In certain embodiments, the functional coat comprises at least one enteric polymer. In certain embodiments, the functional coat layer includes a water-soluble nonionic polymer (such as a polymer that is soluble in physiological fluids and water, e.g., polyethylene glycol, hydroxypropyl methylcellulose, and methylcellulose), an anionic/enteric polymer (e.g., EUDRAGIT® L 100, EUDRAGIT® L 100-55, EUDRAGIT® S 100, and EUDRAGIT® FS), and/or a cationic polymer (e.g., EUDRAGIT® E PO that is soluble in gastric fluids).

In certain embodiments, Naloxone Particulates are enteric coated. In certain embodiments, the functional coat layer comprises at least one anionic/enteric polymer. In certain embodiments, the functional coat layer comprises at least one nonionic polymer and at least one anionic/enteric polymer. In certain embodiments, the functional coat layer comprises at least one nonionic polymer, at least one anionic/enteric polymer, and at least one cationic polymer. In certain embodiments, the cationic polymer is a dimethylaminoethyl methacrylate, butyl methacrylate, and methyl methacrylate copolymer. In certain embodiments, the anionic/enteric polymer is methacrylic acid methyl methacrylate copolymer. In certain embodiments, the dimethylaminoethyl methacrylate, butyl methacrylate, and methyl methacrylate copolymer is EUDRAGIT® E PO. In certain embodiments, the methacrylic acid methyl methacrylate copolymer is EUDRAGIT® L 100-55.

In certain embodiments, the functional coat layer comprises EUDRAGIT® L 100-55 and EUDRAGIT® E PO. In certain embodiments, the amounts of EUDRAGIT® L 100 and EUDRAGIT® E PO are adjusted such that naloxone is co-released with the opioid (i.e., there is an overlap in time to maximum concentration ($T_{max}$) for opioid and naloxone).

In certain embodiments, if three or more dosage units, each dosage unit containing Naloxone Particulates and an opioid, are consumed together, the amount of naloxone released from the three or more dosage units is sufficient to completely or partially reverse/block the opioid effect. In certain embodiments, the pharmacological effect of opioid is reduced/blocked from about 30% to about 90%, from about 40% to about 80%, or from about 50% to about 70%.

In certain embodiments, the functional coated Naloxone Particulates can be further coated with an additional functional coat layer(s). In certain embodiments, additional functional coat layer(s) can comprise a water-soluble nonionic polymer and an anionic polymer; a cationic polymer (e.g., EUDRAGIT® E PO) and an anionic polymer (e.g., EUDRAGIT® L 100, EUDRAGIT® L 100-55); and/or a cationic polymer, an anionic polymer, and a nonionic polymer.

In certain embodiments, the composition of any of the functional coat layer(s) can also include an anti-tacking agent (e.g., talc, magnesium trisilicate, colloidal silicon dioxide (e.g., CAB-O-SIL®)) and/or a plasticizer.

In certain embodiments, Naloxone Particulates (with or without a seal coat) do not include any functional coat (i.e., do not include any functional coat layer; do not include any enteric coat).

6.11. Over Coat

In certain embodiments, the functional coated Naloxone Particulates include an over coat. In certain embodiments, the over coat can include at least one nonionic water-soluble polymer. Such polymers can include a cellulose ether polymer (e.g., a water-soluble methylcellulose and/or hydroxypropyl methylcellulose polymer); polyvinyl pyrrolidone, copolymers of polyvinyl pyrrolidone and vinyl acetate, and mixtures thereof.

In certain embodiments, the composition of the over coat can also include additional excipients such as an anti-tacking agent (e.g., talc, magnesium trisilicate, colloidal silicon dioxide (e.g., CAB-O-SIL®)) and a plasticizer (e.g., triethyl citrate).

In certain embodiments, the over coat can be present in a range of about 5% to about 50% w/w of functional coated Naloxone Particulates. In certain embodiments, Naloxone Particulates (with or without a seal coat and/or with or without a functional coat) do not include any over coat.

7. Viscosity Enhancing Particulates

In certain embodiments, the Viscosity Enhancing Particulates can be Viscosity Enhancing Granules. Viscosity Enhancing Granules increase the viscosity of the dosage form when added to a dissolution medium (e.g., water), thus impeding the ability to extract the opioid from the dosage form, or to pass the dissolution medium with the opioid through a needle for injection purposes.

In certain embodiments, the increase in viscosity can also reduce the potential absorption of the opioid when taken in amounts in excess of two dosage units (e.g., three or more dosage units). As the viscosity of the solution in the GI tract increases, the opioid is eventually entrapped in a polymer gel matrix and the dosage form is transformed from an immediate release formulation to the equivalent of an extended release formulation. It is believed that the ingestion of increasing quantities of the formulation will not proportionally increase the maximum concentration ($C_{max}$) to reach the full potential of abusive effects (e.g., euphoria, sedation, and/or relaxation) of the opioid. In addition, it will take a longer time to reach maximum concentration ($T_{max}$). The result will be a reduced desirability of deliberately abusing or overdosing with an opioid.

In certain embodiments, the Viscosity Enhancing Granules contain a viscosity-building polymer. In certain embodiments, the viscosity-building polymer is present in an amount that is sufficient to increases the viscosity of the proximal fluid in the GI tract if multiple doses, e.g., three or more dosage units, are taken, e.g., deliberately for the purpose of abuse. In certain embodiments, the viscosity-building polymer is present in an amount that prevents syringeability by rapidly forming a gelatinous mass that resists passage through a needle when one or more units are subjected to incubation in about 10 ml of aqueous or nonaqueous media.

In certain embodiments, the Viscosity Enhancing Granules include a polymer matrix that can include a nonionic polymer (e.g., polyethylene oxide (PEO) polymers such as Polyox® WSR coagulant, Polyox® WSR-301, Polyox® WSR-303) and/or pH-dependent polymers (e.g., carbomers such as Carbopol 934P, Carbopol 971P, Carbopol 974P).

In certain embodiments, Viscosity Enhancing Granules include an antioxidant, a plasticizer, and/or a surfactant, each of which can be the same or different from those used in the Opioid Granules. In certain embodiments, the Viscosity Enhancing Granules matrix further includes a glidant (e.g., talc, colloidal silicon dioxide, magnesium trisilicate, powdered cellulose, starch, and tribasic calcium phosphate). In certain embodiments, the Viscosity Enhancing Granules matrix further includes a disintegrant, which can be the same or different from those used in the Triggering Granules.

In certain embodiments, the viscosity-building polymer is present in an amount that does not retard the release of the opioid from a single dose administration, but does slow down the release of the opioid when multiple dosage units are taken together (e.g., three or more dosage units). In certain embodiments, the viscosity-building polymer is present in an amount from about 2% to about 60% w/w of total Viscosity Enhancing Granules. In certain embodiments, the viscosity-building polymer is present in an amount from about 5% to about 55%, about 10% to about 50%, about 15% to about 45%, about 20% to about 40%, or about 25% to about 35% w/w of total Viscosity Enhancing Granules. In certain embodiments, the viscosity-building polymer is present in an amount from about 10% to about 50%, or about 15% to about 20%, w/w of total Viscosity Enhancing Granules.

Viscosity Enhancing Granules can be prepared by any granulation method known to those of skill in the art. For example, the Viscosity Enhancing Granules can be made by dry granulation (e.g., direct blend, compacting and densifying the powders), wet granulation (e.g., addition of a granulation liquid onto a powder bed under the influence of an impeller or air), melt granulation, hot-melt extrusion, extrusion spheronization, or rotor granulation. The granulation product obtained can be milled to achieve uniform granules. The granules obtained can be subsequently coated with an aqueous dispersion.

In certain embodiments, the mean particle size distribution of the Viscosity Enhancing Granules is about 125 µm to about 1000 µm. In certain embodiments, the mean particle size distribution of the Viscosity Enhancing Granules is about 150 µm to about 950 µm, about 200 µm to about 900 µm, about 250 µm to about 850 µm, about 300 µm to about 800 µm, about 350 µm to about 750 µm, about 400 µm to about 700 µm, about 450 µm to about 650 µm, or about 500 µm to about 600 µm. In certain embodiments, the mean particle size distribution of Viscosity Enhancing Granules is about 250 µm to about 750 µm.

8. Particulate and Multi-Particulate Dosage Forms

The presently disclosed subject matter combines ADF and ODP properties in single solid oral immediate release dosage form and thus addresses multiple health-related concerns, especially regarding habit-forming opioid compounds for which there is a high propensity for abuse. In certain embodiments, the abuse deterrence and/or overdose protection activates after the ingestion of three or more dosage units (e.g., three or more tablets/capsules). In certain embodiments, the abuse deterrence and/or overdose protection activates when the multiple dosage units are taken at once. In certain embodiments, the abuse deterrence and overdose protection can activate when the multiple dosage units are taken in tandem. In certain embodiments, release of the opioid after ingesting one to two dosage units results in the dosage form maintaining its (their) immediate release properties (i.e., there is no (or minimal) effect on the release of the opioid from the dosage form(s)). In certain embodiments, if three or more dosage units are taken, release of the opioid from the dosage form is reduced. In certain embodiments, the release is reduced by more than 25%, 30%, 35%, 40%, 45%, 50%, 55%, 60%, 65%, 70%, 75%, 80%, 85%, 90%, 95%, 96%, 97%, 98%, 99%, or increments therein. These dosage forms, however, are not intended to be used as an extended release or sustained release dosage form.

In certain embodiments, the immediate release pharmaceutical dosage form is a particulate dosage form. In certain embodiments, the pharmaceutical dosage forms (multi-particulates) contain at least two different populations of particulates. In certain embodiments, the immediate release pharmaceutical dosage forms contain at least three different populations of particulates. In certain embodiments, the immediate release pharmaceutical dosage forms contain at least four, at least five, at least six, or at least seven different populations of particulates. Each population of particulates is designed for a specific function to accomplish the desired combination of abuse deterrence and overdose protection qualities.

In certain embodiments, the pharmaceutical dosage forms contain at least one population of Opioid Particulates (e.g., Opioid Pellets and/or Opioid Granules) in combination with at least one population of Triggering Granules. In certain embodiments, the Opioid Particulates contain an opioid and an opioid antagonist, e.g., naloxone hydrochloride. In certain embodiments, the alkaline agent of the Triggering Granules increases the pH of the aqueous or nonaqueous solution to above about pH 5.0 in the presence of three or more dosage units, and the pH-stabilizing agent of the Triggering Granules maintains the increased pH above about 5.0 for up to two hours. In certain embodiments, the functional coating of the Opioid Particulates only allows the release of the opioid in an aqueous or nonaqueous environment with a pH below about 5.0 and prevents or slows the release of the opioid at a pH above about 5.0. In certain embodiments, the pharmaceutical dosage form contains a population of Naloxone Particulates. In certain embodiments, the pharmaceutical dosage forms contain at least one population of Viscosity Enhancing Granules. In certain embodiments, the pharmaceutical dosage forms contain at least one population of Opioid Particulates (e.g., Opioid Pellets and/or Opioid Granules, comprising, e.g., an opioid(s)) in combination with at least one population of Triggering Granules and at least one population of Naloxone Particulates. In certain embodiments, the pharmaceutical dosage form comprises at least one population of Opioid Particulates comprising, e.g., an opioid(s) in combination with at least one population of Triggering Granules, a population of Naloxone Particulates, and a population of Viscosity Enhancing Granules. In certain embodiments, the Viscosity Enhancing Granules are present in an amount of from about 2% to about 50% of the total weight of the dosage form.

In certain embodiments, the pharmaceutical dosage forms can contain at least one population of pH-dependent Viscosity Modifying Particulates. In certain embodiments, pH-dependent Viscosity Modifying Particulates are pH-dependent Viscosity Modifying Granules comprising a pH-dependent viscosity building polymer (e.g., carbomers such as Carbopol 934P, Carbopol 971P, and Carbopol 974P). In certain embodiments, the pH-dependent viscosity building polymer can be present in an amount that does not retard the release of the opioid from a single dose administration, but does slow down the release of the opioid after multiple dosage units are taken. In certain embodiments, the pH-dependent Viscosity Modifying Granules can be present in an amount from about 0.5% w/w to about 15% w/w of the total weight of the dosage form. In certain embodiments, the pH-dependent Viscosity Modifying Granules can be present in an amount from about 0.75% w/w to about 12.5%, about 1% to about 10%, or about 2.5% to about 7.5% w/w of the total weight of the dosage form.

In certain embodiments, the pharmaceutical dosage forms contain at least one population of pH-dependent Viscosity Modifying Granules. In certain embodiments, the pharmaceutical dosage forms contain at least one population of Opioid Particulates in combination with at least one population of Triggering Granules, at least one population of Naloxone Particulates, and at least one population of pH-dependent Viscosity Modifying Granules. In certain embodiments, the pharmaceutical dosage forms contain at least one population of Opioid Particulates in combination with at least one population of Triggering Granules, at least one population of Naloxone Particulates, at least one population of Viscosity Enhancing Granules, and at least one population of pH-dependent Viscosity Modifying Granules.

In certain embodiments, the pharmaceutical dosage forms can contain at least one population of Ion Exchange Resin Granules (e.g., AMBERLITE™ IRP 64, AMBERLITE™ IRP 69). The ion exchange resins of the Ion Exchange Resin Granules form a matrix or complex with the drug, and thus can alter the release of drug. In certain embodiments, the ion exchange resin can be present in an amount that binds to the opioid if the dosage form is tampered with, thereby preventing the release of the opioid from the dosage form. In certain embodiments, the Ion Exchange Resin Granules can be present in a concentration of about 1 M to about 5 M and in some embodiments from about 1 M to about 3 M, based on the total molarity of the drug susceptible to abuse.

In certain embodiments, the pharmaceutical dosage forms contain at least one population of Ion Exchange Resin Granules. In certain embodiments, the pharmaceutical dosage forms contain at least one population of Opioid Particulates in combination with at least one population of Triggering Granules, at least one population of Naloxone Particulates, and at least one population of Ion Exchange Resin Granules. In certain embodiments, the pharmaceutical dosage forms contain at least one population of Opioid Particulates in combination with at least one population of Triggering Granules, at least one population of Naloxone Particulates, at least one population of Viscosity Enhancing Granules, and at least one population of Ion Exchange Resin Granules. In certain embodiments, the pharmaceutical dosage forms contain at least one population of Opioid Particulates in combination with at least one population of Triggering Granules, at least one population of Naloxone Particulates, at least one population of Viscosity Enhancing Granules, at least one population of pH-dependent Viscosity Modifying Granules, and at least one population of Ion Exchange Resin Granules. In certain embodiments, the pharmaceutical dosage forms contain at least one population of Opioid Particulates in combination with at least one population of Triggering Granules, at least one population of enteric-coated Naloxone Particulates (or, as noted above, Naloxone Particulates coated with pH independent erodible polymers in combination with enteric polymers, or Naloxone Particulates coated with pH independent erodible polymers in combination with water insoluble polymers), at least one population of Viscosity Enhancing Granules, at least one population of pH-dependent Viscosity Modifying Granules, and at least one population of Ion Exchange Resin Granules.

In certain embodiments, the AD and ODP characteristics of the dosage form have a synergistic effect(s). In certain embodiments, ODP elements of the dosage form further enhance AD features of the dosage form, i.e., in a synergistic manner. In certain embodiments, AD elements of the dosage form further enhance ODP features of the dosage form, i.e., in a synergistic manner. In certain embodiments, the ODP elements, e.g., acid labile coat (functional coat) on the Opioid Particulates, and/or the presence of alkaline agent in, e.g., Triggering Particulates, enhance the AD features (e.g., reduce the amount of active in the syringeable liquid by further controlling the release of the opioid from the dosage form in certain embodiments of deliberate abuse).

In certain embodiments, the pharmaceutical dosage form of the presently disclosed subject matter is a solid immediate release multi-particulate dosage form with abuse deterrent properties and overdose protection elements, comprising a first population of particulates comprising a therapeutically effective amount of at least one opioid embedded in a polymer matrix, and an acid labile coat, a second population of particulates comprising an alkaline agent, and a third population of particulates comprising an opioid antagonist, e.g., naloxone, wherein the abuse deterrent properties comprise resistance to extractability, and resistance to syringeability of the opioid; and the ODP elements comprise the acid labile coat, an alkaline agent, and naloxone hydrochloride; wherein the presence of overdose protection elements enhance the abuse deterrent properties of the dosage form in a synergistic manner. In certain embodiments, the presence of the alkaline agent reduces the amount of opioid present in a syringeable liquid to less than about 10-20%, compared with about 40% of the opioid in a dosage form without an alkaline agent. In certain embodiments, the syringeable liquid is obtained by adding at least one crushed dosage form, with or without an alkaline agent, to water at room temperature and maintaining the resulting suspension at room temperature for, e.g., 30 minutes. In certain embodiments, the dosage form without an alkaline agent comprises a single population of particulates comprising a therapeutically effective amount of at least one opioid embedded in a polymer matrix, and an acid labile coat. In certain embodiments, the dosage form without an alkaline agent comprises a tablet dosage form without Triggering Particulates.

In certain embodiments, the alkaline agent present in Triggering Particulates increases the viscosity of the dosage form by activating pH-dependent anionic polymer(s), e.g., gelling polymers such as carbomers, thereby enhancing the AD features (AD properties), such as reduced dissolution and syringeability of the dosage form, in a synergistic manner. In certain embodiments, the gelling effect of, e.g., carbomers is greatly enhanced in the raised pH resulting from the alkaline agent released from the Triggering Granules involved in ODP. The increased AD effects of such gelling can be part of, e.g., decreases in attempted extraction, and decreased release of opioid in the stomach when three or more dosage units are ingested. In certain embodiments, the presence of naloxone in the syringeable liquid reduces the effect of the amount of opioid present in the syringeable liquid by competitively binding to opioid receptors.

In certain embodiments, the plurality of particulate populations can be blended with other excipients and additives and compressed into a tablet or loaded into a capsule. In certain embodiments, the tablet/capsule dosage form disintegrates rapidly once in contact with aqueous medium. In certain embodiments, the capsule can be a soft or hard gelatin capsule. In certain embodiments, the capsule itself does not alter the release of the opioid.

In certain embodiments, Opioid Particulates are present in an amount from about 10% to about 80% w/w of the total weight of the dosage form. In certain embodiments, the Opioid Particulates are present in an amount from about 15% to about 75%, about 20% to about 70%, about 25% to about 65%, about 30% to about 60%, about 35% to about 55%, or about 40% to about 50% w/w of the total weight of the dosage form. In certain embodiments, the Opioid Particulates are present in an amount from about 50% to about 80%, about 60% to about 80%, or about 70% to about 80% w/w of the total weight of the dosage form. In certain embodiments, the Opioid Particulates are present in an amount from about 10% to about 70%, about 20% to about 70%, about 30% to about 70%, or about 40% to about 70% w/w of the total weight of the dosage form. In certain embodiments, the Opioid Particulates are present in an amount of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% w/w of the total weight of the dosage form.

In certain embodiments, the Triggering Granules are present in an amount from about 10% to about 50% w/w of the total weight of the dosage form. In certain embodiments, the Triggering Granules are present in an amount from about 20% to about 42% w/w of the total weight of the dosage form. In certain embodiments, the Triggering Granules are present in an amount from about 22% to about 40%, about 24% to about 38%, about 26% to about 36%, about 28% to about 34%, or about 30% to about 32% w/w of the total weight of the dosage form. In certain embodiments, the Triggering Granules are present in an amount from about 20% to about 42%, about 22% to about 42%, about 24% to about 42%, about 26% to about 42%, about 28% to about 42%, about 30% to about 42%, about 32% to about 42%, about 34% to about 42%, about 36% to about 42%, about 38% to about 42%, or about 40% to about 42% w/w of the total weight of the dosage form. In certain embodiments, the Triggering Granules are present in an amount of at least about 20%, at least about 22%, at least about 24%, at least about 26%, at least about 28%, at least about 30%, at least about 32%, at least about 34%, at least about 36%, at least about 38%, at least about 40%, or at least about 42% w/w of the total weight of the dosage form.

In certain embodiments, the Naloxone Particulates are present in an amount from about 10% to about 50% w/w of the total weight of the dosage form. In certain embodiments, the Naloxone Particulates are present in an amount from about 20% to about 42% w/w of the total weight of the dosage form. In certain embodiments, the Naloxone Particulates are present in an amount from about 22% to about 40%, about 24% to about 38%, about 26% to about 36%, about 28% to about 34%, or about 30% to about 32% w/w of the total weight of the dosage form. In certain embodiments, the Naloxone Particulates are present in an amount from about 20% to about 42%, about 22% to about 42%, about 24% to about 42%, about 26% to about 42%, about 28% to about 42%, about 30% to about 42%, about 32% to about 42%, about 34% to about 42%, about 36% to about 42%, about 38% to about 42%, or about 40% to about 42% w/w of the total weight of the dosage form. In certain embodiments, the Naloxone Particulates are present in an amount of at least about 20%, at least about 22%, at least about 24%, at least about 26%, at least about 28%, at least about 30%, at least about 32%, at least about 34%, at least about 36%, at least about 38%, at least about 40%, or at least about 42% w/w of the total weight of the dosage form.

In certain embodiments, the Viscosity Enhancing Granules are present in an amount from about 2% to about 50% w/w of the total weight of the dosage form. In certain embodiments, the Viscosity Enhancing Granules are present in an amount from about 5% to about 45%, about 10% to about 40%, about 15% to about 35%, or about 20% to about 30% w/w of the total weight of the dosage form.

In certain embodiments, the pH-Dependent Viscosity Modifying Granules are present in an amount from about 0.5% to about 15% w/w of the total weight of the dosage form. In certain embodiments, the pH-Dependent Viscosity Modifying Granules are present in an amount from about 0.75% to about 12.5%, about 1% to about 10%, or about 2.5% to about 7.5% w/w of the total weight of the dosage form.

In certain embodiments, the Ion Exchange Resin Granules are present in a concentration of about 1 M to about 5 M, or about 1 M to about 3 M, based on the total molarity of the drug susceptible to abuse.

In certain embodiments, one or more opioids, and naloxone can be blended with other excipients and additives and compressed into various tablet dosage forms, e.g., tablet, mini-tablet, tablet-in-tablet, bilayer tablet, or multilayer tablet, or loaded into a capsule, or the like.

In certain embodiments, a single particulate population (e.g., a population of Opioid Particulates; or a population of Opioid Particulates also containing naloxone) can be blended with other excipients and additives and compressed into various tablet dosage forms, e.g., tablet, mini-tablet, tablet-in-tablet, bilayer tablet, or multilayer tablet, or loaded into a capsule, or the like. In certain embodiments, additional solid IR dosage forms including additional particulates, tablet, and/or capsule coating regimens, are contemplated. A nonlimiting set of exemplary dosage forms follows.

In certain embodiments, the formulation is a single particulate dosage form comprising a single population of particulates containing at least one opioid and naloxone, the particulates being compressed into a tablet/mini-tablet or filled in a capsule, and at least one alkalinizing coat covering the tablet/mini-tablet and/or capsule. In certain embodiments, the Opioid Particulates are compressed with alkaline agent into a tablet/mini-tablet or filled in a capsule.

In certain embodiments, the multi-particulate dosage form is a two particulate dosage form comprising a first population of Opioid Particulates containing an opioid and naloxone, and a second population of Triggering Particulates, the two particulate populations being compressed into a tablet/mini-tablet or filled with naloxone in a capsule.

In certain embodiments, the multi-particulate dosage form is a two-particulate dosage form comprising a first population of Opioid Particulates containing an opioid, and a second population of Naloxone Particulates, the two particulate populations being compressed into a tablet/mini-tablet or filled with naloxone in a capsule. In certain embodiments, Naloxone Particulates contain enteric coated naloxone hydrochloride.

In certain embodiments, the multi-particulate dosage form is a two-particulate dosage form comprising a first population of Opioid Particulates containing an opioid, and a second population of Naloxone Particulates, the two particulate populations being compressed with an alkaline agent into a tablet/mini-tablet or filled with naloxone in a capsule. In certain embodiments, Naloxone Particulates contain enteric coated naloxone hydrochloride.

In certain embodiments, the multi-particulate dosage form is a three particulate dosage form comprising a first population of Opioid Particulates containing an opioid, a second population of Triggering Particulates, and a third population of Naloxone Particulates, the three particulate populations being compressed into a tablet/mini-tablet or filled in a capsule.

In certain embodiments, the multi-particulate dosage form is a three particulate dosage form comprising a first population of Opioid Particulates containing an opioid, a second population of Triggering Particulates, and a third population of enteric coated Naloxone Particulates, the three particulate populations being compressed into a tablet/mini-tablet or filled in a capsule.

In certain embodiments, the tablet/mini-tablet is further coated with an acid labile coat and, optionally, an alkalinizing coat on top of the acid labile coat.

In certain embodiments, Opioid Particulates contain an alkaline agent and, optionally, a pH-stabilizing agent in the polymer matrix.

In certain embodiments, the size of Opioid Particulates is, e.g., about 400 micrometers to about 2-3 mm, to provide enhanced control of release of the opioid in an ODP setting, while providing required and desired immediate release (independent of any food effect) when one or two dosage units are consumed.

In certain embodiments, capsules contain coated Opioid Particulates coated with a functional coat layer(s) and an over coat, and Naloxone Particulates.

In certain embodiments, capsules contain coated Opioid Particulates coated with a functional coat layer(s) and an over coat, Naloxone Particulates, and Triggering Particulates.

In certain embodiments, capsules contain coated Opioid Particulates coated with a functional coat layer(s) and an over coat, enteric-coated Naloxone Particulates, and Triggering Particulates.

In certain embodiments, capsules contain Triggering Particulates, Naloxone Particulates, and tablets/mini-tablets made from coated Opioid Particulates.

In certain embodiments, capsules contain Triggering Particulates, enteric coated Naloxone Particulates, and tablets/mini-tablets made from coated Opioid Particulates.

In certain embodiments, capsules contain Triggering Particulates, and tablets/mini-tablets made from coated Opioid Particulates and tablets/minitablets made from Naloxone Particulates.

In certain embodiments, capsules contain Triggering Particulates, and tablets/mini-tablets made from coated Opioid Particulates and tablets/minitablets made from enteric-coated Naloxone Particulates.

In certain embodiments, capsules contain tablets/mini-tablets of coated Opioid Particulates, tablets/mini-tablets of Naloxone Particulates, and tablets/mini-tablets of Triggering Particulates. In certain embodiments, capsules contain tablets/mini-tablets of coated Opioid Particulates, tablets/mini-tablets of enteric-coated Naloxone Particulates, and tablets/mini-tablets of Triggering Particulates.

In certain embodiments, capsules contain coated Opioid Particulates, and tablets/mini-tablets of Triggering Particulates.

In certain embodiments, capsules contain (1) mini-tablets/tablets comprising coated Opioid Particulates, Naloxone Particulates (naked or enteric-coated), and at least a portion of Triggering Particulates; and (2) a remaining portion of Triggering Particulates.

In certain embodiments, the dosage form is a bilayer tablet comprising a first layer further comprising Opioid Particulates and Naloxone Particulates (naked or enteric coated), and a second layer comprising Triggering Particulates, and the two layers are compressed into a bilayer tablet.

In certain embodiments, the first layer is coated with at least one functional coat layer and an over coat on top of the at least one functional coat layer.

In certain embodiments, the dosage form is a bilayer tablet comprising a first layer comprising a coated tablet comprising Opioid Particulates, and Naloxone Particulates, and a second layer comprising Triggering Particulates, and the two layers are compressed into a bilayer tablet.

In certain embodiments, the dosage form is a trilayer tablet comprising a first layer comprising a coated tablet comprising Opioid Particulates, a second layer comprising Naloxone Particulates, and a third layer comprising Triggering Particulates, and the three layers are compressed into a trilayer tablet.

In certain embodiments, the dosage form is a bilayer tablet comprising a first layer comprising a coated tablet comprising Opioid Particulates, and enteric coated Naloxone Particulates, and a second layer comprising Triggering Particulates, and the two layers are compressed into a bilayer tablet.

In certain embodiments, the dosage form is a trilayer tablet comprising a first layer comprising a coated tablet comprising Opioid Particulates, a second layer comprising enteric coated Naloxone Particulates, and a third layer comprising Triggering Particulates, and the three layers are compressed into a trilayer tablet.

In certain embodiments, the dosage form is a tablet-in-tablet dosage form comprising an inner tablet comprising coated Opioid Particulates, and Naloxone Particulates, and an outer tablet, comprising Triggering Particulates, encasing the inner tablet.

In certain embodiments, the dosage form is a tablet-in-tablet dosage form comprising an inner tablet comprising coated Opioid Particulates, and enteric coated Naloxone Particulates, and an outer tablet, comprising Triggering Particulates, encasing the inner tablet.

In certain embodiments, the dosage form is a tablet-in-tablet dosage form comprising an inner coated tablet comprising Opioid Particulates, and Naloxone Particulates (naked or enteric coated), an outer tablet, partially or completely encasing the inner tablet, comprising Triggering Particulates.

In certain embodiments, the dosage form is a capsule dosage form comprising Triggering Particulates, and compressed tablets/mini-tablets comprising Opioid Particulates and Naloxone Particulates (naked or enteric coated).

In certain embodiments, the dosage form is a capsule dosage form comprising Opioid Particulates, Naloxone Particulates (naked or enteric coated), and compressed tablets/mini-tablets comprising Triggering Particulates In certain embodiments, the dosage form is a capsule dosage form comprising compressed tablets/mini-tablets comprising Opioid Particulates, compressed tablets/mini-tablets comprising Naloxone Particulates (naked or enteric coated), and compressed tablets/mini-tablets comprising Triggering Particulates.

In certain embodiments, one or more of the above dosage forms is without a Triggering Particulate, an alkaline agent, or an alkalinizing coat.

9. Syringeability and Extractability Resistance, and Heat Stability

In certain embodiments, the particulate and multi-particulate dosage forms of the presently disclosed subject matter provide several additional abuse-deterrent properties, including syringeability resistance, extractability resistance, and heat stability. For example, the multi-particulate dosage forms resist abuse via, but not limited to, extraction of the opioid from the dosage form, syringeability of the opioid from the dosage form, and destabilization of the several abuse-deterrent attributes by various thermal pretreatment-related manipulations (e.g., heating or freezing of the dosage form before mechanical manipulations, e.g., crushing or grinding). In certain embodiments, the combination of these additional properties, along with the aforementioned resistance to crushability and grindability of the Opioid Particulates, strongly deter or prevent abuse of the inventive multi-particulate dosage form.

In certain embodiments, resistance to extractability is provided by, e.g., carbomers in the Opioid Particulates of the dosage form. In certain embodiments, carbomers (such as Carbopol 934P, Carbopol 971P, Carbopol 974P), as well as other anionic polymers that are viscosity-enhancing agents, form gel and increase viscosity in aqueous and/or alcoholic media, such as those media used by abusers attempting extraction of opioid from a given dosage form. In certain embodiments, the gelling effect of carbomers is greatly enhanced in alkaline pH resulting from the alkaline agent released from the Triggering Granules (e.g., in attempted extraction, or in the stomach when three or more dosage units are ingested), or the alkaline agent when present in the polymer matrix. In certain embodiments, carbomers in the core form gel and further diminish drug release, e.g., permeation from the core of Opioid Particulates into the GI fluid, or into aqueous media attempting to be drawn into a syringe. In certain embodiments, polymers present in the functional coat(s), e.g., EUIDRAGIT® E PO, are also involved in decreasing permeation of the opioid from the Opioid Particulates, e.g., when extraction is attempted. The alkaline agent(s) present in the dosage forms produce a rapid rise in the pH of aqueous media (e.g., in attempted extraction, or in the stomach when three or more dosage units are ingested). The polymers present in the functional coats, e.g., EUDRAGIT® E PO, become insoluble in this alkaline media; thus the release of opioid from the dosage form is blocked.

In certain embodiments, resistance to syringeability is provided by polyoxyethylene (PEO) polymers and HPMC in the Opioid Particulates (e.g., in the core of the Opioid Granules). The gelling characteristics of these molecules, when exposed to aqueous media, provide resistance to syringeability as the bore of the needle is blocked by the viscous nature of the diluted dosage form. In addition, carbomers included in the dosage form (e.g., in the core of the Opioid Granules) provide further resistance to syringeability; in response to the rapidly rising pH induced by, e.g., $Mg(OH)_2$ in aqueous media, carbomer-based gelling is greatly enhanced, further diminishing drug release.

These unique combinations of elements and features of the dosage form are prominent, for example, in a physiological setting involving accidental overdose (or deliberate abuse) comprising ingestion of multiple dosage units (dosage forms).

10. Methods of Treatment and Manufacture

In certain embodiments, the presently disclosed subject matter provides several methods of treatment, manufacture, etc., closely related to the opioid agonist/antagonist combination pharmaceutical dosage forms and formulations.

In certain embodiments, the presently disclosed subject matter is directed to a method of managing or treating pain with opioids, and discouraging their abuse or misuse. The method comprises orally administering to a subject in need thereof a multi-particulate solid oral immediate release opioid agonist/antagonist combination dosage form with abuse deterrent and overdose protection properties comprising (1) a first population of particulates comprising a therapeutically effective amount of at least one opioid, as a free base or a pharmaceutically acceptable salt thereof, embedded in a polymer matrix, wherein the individual particulates are coated with an acid labile coat; (2) a second population of particulates comprising an alkaline agent and, optionally, a pH-stabilizing agent; and (3) a third population of particulates comprising naloxone hydrochloride. In certain embodiments, when three or more units of the dosage form are consumed together by the subject, a pharmacologically effective amount of naloxone hydrochloride is bioavailable to block binding of agonist to central opioid receptors.

In certain embodiments, the presently disclosed subject matter is directed to a method to block binding of agonist to central opioid receptors in a subject. The method comprises orally administering to the subject a multi-particulate solid oral immediate release opioid agonist/antagonist combination dosage form with abuse deterrent and overdose protection properties comprising (1) a first population of particulates comprising a therapeutically effective amount of at least one opioid, in a free base form or a pharmaceutically acceptable salt thereof, embedded in a polymer matrix, wherein the individual particulates are coated with an acid labile coat; (2) a second population of particulates comprising an alkaline agent; and (3) a third population of particulates comprising naloxone hydrochloride. In certain embodiments, the third population of particulates containing naloxone hydrochloride is enteric coated. In certain embodiments, the overdose protection properties comprise reduction or reversal of opioid effects when three or more dosage units are consumed together. In certain embodiments, when three or more dosage units are consumed together by the subject, a pharmacologically effective amount of naloxone hydrochloride is bioavailable to block binding of the opioid (i.e., the agonist) to central opioid receptors. In certain embodiments, the binding of agonist to central opioid receptors in the subject is blocked for about 20-90 minutes.

In certain embodiments, the presently disclosed subject matter provides a method for manufacturing a multi-particulate solid oral immediate release opioid agonist/antagonist combination dosage form with abuse deterrent and overdose protection properties. The method comprises (1) making a first population of particulates comprising a therapeutically effective amount of at least one opioid, in a free base form or a pharmaceutically acceptable salt thereof, embedded in a polymer matrix, and coating the individual particulates with an acid-labile coat; (2) making a second population of particulates comprising an alkaline agent; (3) making a third population of particulates comprising naloxone hydrochloride, and coating the particulates with an enteric coat; and (4) compressing the three populations into a tablet, tablet-in-tablet, bilayer tablet, or multilayer tablet, or loading the three populations into a capsule. In certain embodiments, the enteric coated naloxone hydrochloride is not co-released with, e.g., oxycodone hydrochloride when one or two dosage units of the dosage form are consumed together. In certain embodiments, the enteric coated naloxone hydrochloride is co-released with at least a portion of, e.g., oxycodone hydrochloride when three or more dosage units of the dosage form are consumed together. In certain embodiments, the presently disclosed subject matter is directed to a method for providing overdose protection from an opioid overdose. The method comprises orally administering to a subject a multi-particulate solid oral immediate release opioid agonist/antagonist combination dosage form with abuse deterrent and overdose protection properties comprising (1) a first population of particulates comprising a therapeutically effective amount of at least one opioid (e.g., oxycodone) embedded in a polymer matrix, wherein the individual particulates are coated with an acid labile coat; (2) a second population of particulates comprising an alkaline agent; and (3) a third population of particulates comprising naloxone hydrochloride. In certain embodiments, when three or more units of the dosage form are consumed together by a subject, a pharmacologically effective amount of naloxone hydrochloride is bioavailable to block binding of agonist (e.g., oxycodone) to central opioid receptors.

In certain embodiments, the presently disclosed subject matter is directed to a method for providing analgesia by administering an opioid dosage form to a subject in an overdose protection formulation without impeding release of the opioid when taken as directed. The method comprises orally administering to the subject a multi-particulate solid oral immediate release opioid agonist/antagonist combination dosage form with abuse deterrent and overdose protection properties comprising (1) a first population of particulates comprising a therapeutically effective amount of at least one opioid (e.g., oxycodone), in a free base form or a pharmaceutically acceptable salt, embedded in a polymer matrix, wherein the individual particulates are coated with an acid labile coat; (2) a second population of particulates comprising an alkaline agent; and (3) a third population of particulates comprising naloxone hydrochloride. In certain embodiments, the third population of particulates containing naloxone hydrochloride is enteric coated. In certain embodiments, when one or two dosage units are consumed together by the subject, a pharmacologically effective amount of naloxone hydrochloride is not co-released with oxycodone and is not bioavailable to block binding of the agonist to central opioid receptors.

In certain embodiments, the presently disclosed subject matter comprises a dosing regimen comprising orally administering to a subject in need thereof, a pharmaceutical composition comprising a multi-particulate solid oral immediate release opioid agonist/antagonist combination dosage form with abuse deterrent and overdose protection properties. In certain embodiments, the pharmaceutical composition comprises (1) a first population of particulates comprising a therapeutically effective amount of at least one opioid, or a pharmaceutically acceptable salt thereof, embedded in a polymer matrix, wherein the individual particulates are coated with an acid labile coat; (2) a second population of particulates comprising an alkaline agent; and (3) a third population of particulates comprising naloxone hydrochloride. In certain embodiments, the dosing regimen comprises administering one or two dosage units of the pharmaceutical composition every 4 to 6 hours as needed for pain. In certain embodiments, the opioid is oxycodone hydrochloride. In certain embodiments, the dosing regimen comprises administering 5 to 20 mg of oxycodone hydrochloride every 4 to 6 hours.

In certain embodiments, the third population of particulates comprising naloxone hydrochloride is enteric coated. In certain embodiments, the third population of particulates comprises lipid based naloxone composition. In certain embodiments, the third population of particulates comprises ASD of naloxone and at least one polymer.

The following examples are offered to more fully illustrate the presently disclosed subject matter, but are not to be construed as limiting the scope thereof.

EXAMPLES

Example 1: Crush-Resistant Oxycodone Hydrochloride Granule Cores (Opioid Granules)

Oxycodone hydrochloride granule cores were prepared for use in a 5 mg, 10 mg, 15, mg, and 30 mg oxycodone hydrochloride dosage form.

TABLE 1

Formulation of Opioid Granule Cores

| Components | Opioid Granule Core 1 mg/dose | Opioid Granule Core 2 mg/dose | Opioid Granule Core 3 mg/dose | Opioid Granule Core 4 mg/dose |
|---|---|---|---|---|
| Oxycodone hydrochloride | 5.00 | 10.00 | 15.00 | 30.00 |
| POLYOX ® WSR coagulant | 65.44 | 65.44 | 65.44 | 50.44 |
| Microcrystalline Cellulose (Avicel PH 101) | 10.00 | 5.00 | NA | NA |
| Hypromellose (Benecel K200M) | 9.41 | 9.41 | 9.41 | 9.41 |
| Kollidon SR | 4.71 | 4.71 | 4.71 | 4.71 |
| Triethyl citrate | 3.24 | 3.24 | 3.24 | 3.24 |
| Docusate sodium (85%) with sodium benzoate (15%) (DOSS) | 2.00 | 2.00 | 2.00 | 2.00 |
| Vitamin E (dl-α-Tocopherol) | 0.20 | 0.20 | 0.20 | 0.20 |
| Total | 100 | 100 | 100 | 100 |

Manufacturing Procedure:

1. Oxycodone hydrochloride, POLYOX® WSR coagulant, microcrystalline cellulose, hypromellose, Kollidon SR, and docusate sodium were added to a high shear granulator and mixed into a uniform powder mix using an impeller and a chopper.
2. A solution of dl-α-tocopherol solution and triethyl citrate was sprayed onto the powder mix from step #1 to achieve a uniform blend.
3. The blend from step #2 was granulated by hot-melt extrusion.
4. The granules from step #3 were processed using cryomilling to a mean particle size of about 500 μm.

Example 2: Crush-Resistant Oxycodone Hydrochloride Granule Cores (Opioid Granules)

Oxycodone hydrochloride granule cores (Granule cores 5-8) were prepared for use in a 5 mg, and 15 mg oxycodone hydrochloride dosage form.

TABLE 2

Composition of Opioid granules

| Composition | Opioid Granule Core 5 (% w/w) | Opioid Granule Core 5 mg/dose | Opioid Granule Core 6 (% w/w) | Opioid Granule Core 6 mg/dose |
|---|---|---|---|---|
| Oxycodone Hydrochloride | 5.00 | 5.00 | 15.00 | 15.00 |
| POLYOX ® WSR coagulant | 84.09 | 84.09 | 65.85 | 65.85 |
| Triethyl citrate | 8.41 | 8.41 | 6.14 | 6.14 |
| Docusate sodium | 2.00 | 2.00 | 2.00 | 2.00 |
| α-dl-Tocopherol | 0.50 | 0.50 | 0.50 | 0.50 |
| Total | 100.0 | 100.0 | 100.0 | 100.0 |

TABLE 3

Composition of Opioid granules

| Composition | Opioid Granule Core 7 (% w/w) | Opioid Granule Core 7 mg/dose | Opioid Granule Core 8 (% w/w) | Opioid Granule Core 8 mg/dose |
|---|---|---|---|---|
| Oxycodone Hydrochloride | 5.00 | 5.00 | 15.00 | 15.00 |
| POLYOX ® WSR coagulant | 69.64 | 69.64 | 65.85 | 65.85 |
| Hydroxypropyl methyl cellulose, K200M | 12.89 | 12.89 | 9.41 | 9.41 |
| Kollidon SR | 6.44 | 6.44 | 4.71 | 4.71 |
| Triethyl citrate | 3.83 | 3.83 | 2.83 | 2.83 |
| Docusate sodium | 2.00 | 2.00 | 2.00 | 2.00 |
| α-dl-Tocopherol | 0.20 | 0.20 | 0.20 | 0.20 |
| Total | 100.0 | 100.0 | 100.0 | 100.0 |

Manufacturing Procedure:

1. Oxycodone hydrochloride, POLYOX® WSR coagulant, docusate sodium, Hydroxypropyl methyl cellulose K200M (Cores 7 & 8), and Kollidon SR (Cores 7 & 8) are added to a high shear granulator and mixed to obtain a uniform powder mix using impeller and chopper at medium speeds.
2. A solution of α-dl-Tocopherol and triethyl citrate is sprayed onto the powder mix from step #1 to obtain a uniform blend.
3. The blend from step #2 is granulated using hot-melt extrusion, melt granulation, roller compaction, high shear or low shear mixing.
4. If required, granules from step #3 are subjected to appropriate delumping or size reduction process using co-mill, fitz mill, cryomilling, micropulverizer or micronization.
5. The resulting granules from step #3 or #4 (if present) are spheronized using rotor.
6. The spheronized granules from step #5 are cured.

Example 3: Crush-Resistant Hydromorphone Hydrochloride Granule Cores (Opioid Granules)

Hydromorphone hydrochloride granule core was prepared for use in an 8 mg hydromorphone hydrochloride dosage form.

TABLE 4

Formulation of Opioid Granule Cores

| Components | mg/dose |
|---|---|
| Hydromorphone hydrochloride | 8.00 |
| POLYOX ® WSR coagulant | 32.20 |
| Hypromellose (Benecel K 200M) | 4.71 |
| Kollidon ® SR | 2.36 |
| Triethyl citrate | 0.10 |
| Docusate sodium | 1.62 |
| Vitamin E (dl-α-Tocopherol) | 1.00 |
| Total | 50.00 |

Manufacturing Procedure:

1. Hydromorphone hydrochloride, POLYOX® WSR coagulant, hypromellose, Kollidon® SR, and docusate sodium were added to a high shear granulator and mixed into a uniform powder mix using an impeller and a chopper.
2. A solution of dl-α-tocopherol solution and triethyl citrate was sprayed onto the powder mix from step #1 to achieve a uniform blend.

3. The blend from step #2 was granulated by hot-melt extrusion.
4. The granules from step #3 were processed using cryomilling to a mean particle size of about 500 μm.

Example 4: Crush-Resistant Hydrocodone Bitartrate Granule Cores (Opioid Granules)

Hydrocodone bitartrate granule core was prepared for use in a 10 mg hydrocodone bitartrate dosage form.

TABLE 5

Formulation of Opioid Granule Cores

| Components | mg/dose |
|---|---|
| Hydrocodone bitartrate | 10.00 |
| POLYOX ® WSR coagulant | 70.44 |
| Hypromellose (Benecel K 200M) | 9.41 |
| Kollidon ® SR | 4.71 |
| Triethyl citrate | 0.20 |
| Docusate sodium | 3.24 |
| dl-α-Tocopherol | 2.00 |
| Total | 100.00 |

Manufacturing Procedure:
1. Hydrocodone bitartrate, POLYOX® WSR coagulant, hypromellose, Kollidon® SR, and docusate sodium are added to a high shear granulator and mixed into a uniform powder mix using an impeller and a chopper.
2. A solution of dl-α-tocopherol solution and triethyl citrate is sprayed onto the powder mix from step #1 to achieve a uniform blend.
3. The blend from step #2 is granulated by hot-melt extrusion.
4. The granules from step #3 are processed cryomilling to a mean particle size of about 500 μm.

Example 5: Seal Coating of Oxycodone Hydrochloride Granule Cores

Oxycodone hydrochloride active granule cores were coated with a seal coat.

TABLE 6

Formulation of Seal Coated Granules

| Components | Seal Coated Granule 1 mg/dose | Seal Coated Granule 2 mg/dose | Seal Coated Granule 3 mg/dose | Seal Coated Granule 4 mg/dose |
|---|---|---|---|---|
| Opioid Granule Cores (Oxycodone hydrochloride) | 100.00 | 100.00 | 100.00 | 100.00 |
| Hypromellose (Methocel E5 Premium LV) | 17.78 | 17.78 | 17.78 | 17.78 |
| Triethyl citrate | 1.78 | 1.78 | 1.78 | 1.78 |
| Colloidal silicon dioxide (Cab-O-Sil (M-5P) | 0.44 | 0.44 | 0.44 | 0.44 |
| Solvent system for coating | | | | |
| Purified water | NA | NA | NA | NA |
| Dehydrated alcohol | NA | NA | NA | NA |
| Total | 120.00 | 120.00 | 120.00 | 120.00 |

TABLE 7

Formulation of Seal Coated Granules

| Composition | (% w/w) | mg/dose |
|---|---|---|
| Oxycodone Hydrochloride (#5-8) | 83.33 | 100.00 |
| Hypromellose (Methocel E5 Premium LV) | 14.82 | 17.78 |
| Triethyl citrate | 1.48 | 1.78 |
| Cab-o-sil | 0.37 | 0.44 |
| Solvent system for coating | | |
| Purified water* | 20.00 | NA |
| Dehydrated Alcohol* | 80.00 | NA |
| Total | 100.00 | 120.00 |

Coating Procedure:
1. Hypromellose was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (20 mg) was achieved.
6. The coated granules from step #5 were dried.

Example 6: Seal Coating of Hydromorphone Hydrochloride Granule Cores

Hydromorphone hydrochloride active granule cores were coated with a seal coat.

TABLE 8

Formulation of Seal Coated Granules

| Components | Seal Coated Granules (mg/dose) |
|---|---|
| Opioid Granule cores (Hydromorphone hydrochloride) | 50.00 |
| Hypromellose (Methocel E5 Premium LV) | 8.89 |
| Triethyl citrate | 0.89 |
| Colloidal silicon dioxide (Cab-O-Sil (M-5P) | 0.22 |
| Solvent system for coating | |
| Purified water | NA |
| Dehydrated alcohol | NA |
| Total | 60.00 |

Coating Procedure:
1. Hypromellose was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.

4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (10 mg) was achieved.
6. The coated granules from step #5 were dried.

Example 7: Seal Coating of Hydrocodone Bitartrate Granule Cores

Hydrocodone bitartrate active granule cores were coated with a seal coat.

TABLE 9

Formulation of Seal Coated Granules

| Components | Seal Coated Granules (mg/dose) |
|---|---|
| Opioid Granule Cores (Hydrocodone bitartrate) | 100.00 |
| Hypromellose (Methocel E5 Premium LV) | 17.78 |
| Triethyl citrate | 1.78 |
| Colloidal silicon dioxide (Cab-O-Sil (M-5P) | 0.44 |
| Solvent system for coating | |
| Purified water | NA |
| Dehydrated alcohol | NA |
| Total | 120.00 |

Coating Procedure:
1. Hypromellose was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (20 mg) was achieved.
6. The coated granules from step #5 were dried.

Example 8: Functional Coating of Seal Coated Oxycodone Hydrochloride Granules

Seal coated oxycodone hydrochloride granules were coated with a first functional coat layer FC 1 comprising a mixture of rate controlling polymers, e.g., cellulose acetate (CA) and EUDRAGIT® E PO, in a ratio of CA:EUDRAGIT® E PO of 60:40, and a second functional coat layer FC 2 comprising EUDRAGIT® E PO as the sole rate controlling polymer.

TABLE 10

Formulation of Functional Coated Opioid Granules

| Components | Functional Coated Granule 1 (mg/dose) | Functional Coated Granule 2 (mg/dose) | Functional Coated Granule 3 (mg/dose) | Functional Coated Granule 4 (mg/dose) |
|---|---|---|---|---|
| FC 1 | | | | |
| Seal coated granules | 120.00 | 120.00 | 120.00 | 120.00 |
| Cellulose acetate (CA 398-10NF/EP) | 18.00 | 18.00 | 18.00 | 18.00 |
| Amino methacrylate copolymer, NF (EUDRAGIT ® E PO) | 12.00 | 12.00 | 12.00 | 12.00 |
| Dibutyl Sebacate | 4.50 | 4.50 | 4.50 | 4.50 |
| Colloidal Silicon Dioxide (Cab-O-Sil M5P) | 1.50 | 1.50 | 1.50 | 1.50 |
| Solvent system for coating | | | | |
| Acetone | NA | NA | NA | |
| Purified water | NA | NA | NA | NA |
| Total | 156.00 | 156.00 | 156.00 | 156.00 |
| FC 2 | | | | |
| FC 1 coated granules | 156.00 | 156.00 | 156.00 | 156.00 |
| Amino methacrylate copolymer, NF (EUDRAGIT ® E PO) | 72.00 | 72.00 | 72.00 | 72.00 |
| Polyethylene Glycol, NF (Polyglykol 6000 PF) | 7.20 | 7.20 | 7.20 | 7.20 |
| Talc USP (2755) | 14.40 | 14.40 | 14.40 | 14.40 |
| Solvent system for coating | | | | |
| Acetone | NA | NA | NA | NA |
| Purified water | NA | NA | NA | NA |
| Total | 249.6 | 249.6 | 249.6 | 249.6 |

Coating Procedure:
1. EUDRAGIT® E PO was added to acetone in a stainless steel container and mixed until a clear solution formed.
2. To the solution from step #1, cellulose acetate was added and mixed until a clear solution formed.
3. The purified water was added to the solution from step #2 and mixed for 5 minutes.
4. To the solution from step #3, dibutyl sebacate was added followed by colloidal silicon dioxide and continued mixing until a homogenous dispersion was obtained.
5. The seal coated granules were further coated using a Wurster fluid bed coater with an inlet air temperature of 40°-50° C. and sufficient air volume for fluidization.
6. When the product temperature reached 30° C., the dispersion from step #4 was sprayed onto the seal coated granules while maintaining the product temperature of 28°-30° C. and sufficient air volume for the fluidization, until the target coating weight gain (36 mg) was achieved.
7. The coated granules from step #6 were dried to FC 1 coated granules.

The FC 1 coated granules were further coated with a second functional coat layer (FC 2) as follows:
EUDRAGIT® E PO was added to acetone in a stainless steel container and mixed until a clear solution form.
1. The purified water was added to the solution from step #1 and mixed for 5 minutes.
2. To the solution from step #3, polyethylene glycol was added followed by talc and mixed until a homogenous dispersion was obtained.

3. The FC 1 coated granules were further coated using a Wurster fluid bed coater with an inlet air temperature of 40°50° C., and sufficient air volume for fluidization.
4. When the product temperature reached 30° C., the dispersion from step #4 was sprayed onto the FC 1 coated granules while maintaining the product temperature of 28°30° C. and sufficient air volume for the fluidization, until the target coating weight gain (93.6 mg) was achieved.
5. The coated granules from step #6 were dried to FC 2 coated granules.

TABLE 11

Formulation of Functional Coated Opioid Granules (FC1)

| Composition | Functional Coated Opioid Granules (#5-8) (FC1) | |
|---|---|---|
| | (% w/w) | mg/dose |
| Seal coated Oxycodone hydrochloride granules | 76.92 | 76.92 |
| Cellulose Acetate | 11.54 | 11.54 |
| Eudragit ® E PO | 7.69 | 7.69 |
| Dibutyl sebacate | 2.88 | 2.88 |
| Colloidal silicon dioxide | 0.96 | 1.50 |
| Solvent system for coating | | |
| Acetone* | 90.00 | NA |
| Purified water* | 10.00 | NA |
| Total | 100.00 | 156.00 |

*Removed during process

*Removed during process

Coating Procedure:
1. Eudragit® E PO is added to acetone in a stainless steel container and mixed until a clear solution formed.
2. To the solution from step #1 Cellulose Acetate is added and mixed until a clear solution formed.
3. The purified water is added to the solution from step #2 and mixed for ~5 minutes.
4. To the solution from step #3 dibutyl sebacate is added followed by colloidal silicon dioxide and continued mixing until a homogenous dispersion is formed.
5. The seal coated granules are further coated using a Wurster fluid bed coater with an inlet air temperature of 40°-50° C. and sufficient air volume for fluidization.
6. When the product temperature reaches 30° C., the dispersion from step #4 is sprayed onto the seal coated granules while maintaining the product temperature of 28°-30° C. and sufficient air volume for the fluidization until the target coating weight gain is reached.
7. The coated granules from step #6 are dried to FC 1 coated granules.
8. The FC 1 coated granules are further coated with a second functional coat layer (FC 2) as follows:

TABLE 12

Formulation of Functional Coated Opioid Granules (FC2)

| Composition | Functional Coated Opioid Granules(# 5-8) (FC2) | |
|---|---|---|
| | (% w/w) | mg/dose |
| Functional coated Oxycodone hydrochloride granules (FC1) | 62.50 | 156.00 |
| Eudragit ® E PO | 28.85 | 72.00 |

TABLE 12-continued

Formulation of Functional Coated Opioid Granules (FC2)

| Composition | Functional Coated Opioid Granules(# 5-8) (FC2) | |
|---|---|---|
| | (% w/w) | mg/dose |
| Polyethylene glycol | 2.88 | 7.20 |
| Talc | 5.77 | 14.40 |
| Solvent system for coating | | |
| Acetone* | 40.00 | NA |
| Isopropyl alcohol* | 60.00 | NA |
| Total | 100.00 | 249.60 |

*Removed during process

1. Eudragit E PO is added to the solution of acetone and isopropyl alcohol in a stainless steel container and mixed until a clear solution formed.
2. To the solution from step #1 polyethylene glycol is added followed by talc and continued mixing until a homogenous dispersion is formed.
3. The functional coated granules (FC1) are further coated using a Wurster fluid bed coater with an inlet air temperature of 40°-50° C. and sufficient air volume for fluidization.
4. When the product temperature reaches 30° C., the dispersion from step #2 is sprayed onto the functional coated granules (FC1) while maintaining the product temperature of 28°-30° C. and sufficient air volume for the fluidization until the target coating weight gain is reached.
5. The coated granules from step #4 are dried.

Example 9: Functional Coating of Seal Coated Hydromorphone Hydrochloride Granules Seal coated hydromorphone hydrochloride granules were coated with a first functional coat layer FC 1 comprising a mixture of rate controlling polymers, e.g., cellulose acetate (CA) and EUDRAGIT® E PO, in a ratio of CA:EUDRAGIT® E PO of 60:40, and a second functional coat layer FC 2 comprising EUDRAGIT® E PO as the sole rate controlling polymer.

TABLE 13

Formulation of Functional Coated Opioid Granules

| Components | Functional Coated Granules mg/dose |
|---|---|
| FC 1 | |
| Seal coated hydromorphone hydrochloride granules | 60.00 |
| Cellulose acetate | 9.00 |
| EUDRAGIT ® E PO | 6.00 |
| Dibutyl sebacate | 2.25 |
| Colloidal silicon dioxide | 0.75 |
| Solvent system for coating | |
| Acetone | NA |
| Purified water | NA |
| Total | 78.00 |
| FC 2 | |
| FC 1 coated granules | 78.00 |
| EUDRAGIT ® E PO | 36.00 |

TABLE 13-continued

Formulation of Functional Coated Opioid Granules

| Components | Functional Coated Granules mg/dose |
|---|---|
| Polyethylene glycol | 3.60 |
| Talc | 7.20 |
| Solvent system for coating | |
| Acetone | NA |
| Isopropyl alcohol | NA |
| Total | 124.80 |

Coating Procedure:
1. EUDRAGIT® E PO was added to acetone in a stainless steel container and mixed until a clear solution formed.
2. To the solution from step #1, cellulose acetate was added and mixed until a clear solution formed.
3. The purified water was added to the solution from step #2 and mixed for ~5 minutes.
4. To the solution from step #3, dibutyl sebacate was added followed by colloidal silicon dioxide and continued mixing until a homogenous dispersion was obtained.
5. The seal coated granules were further coated using a Wurster fluid bed coater with an inlet air temperature of 40°-50° C. and sufficient air volume for fluidization.
6. When the product temperature reached 30° C., the dispersion from step #4 was sprayed onto the seal coated granules while maintaining the product temperature of 28°-30° C. and sufficient air volume for the fluidization, until the target coating weight gain (18 mg) was achieved.
7. The coated granules from step #6 were dried to FC 1 coated granules.

The FC 1 coated granules were further coated with a second functional coat layer (FC 2) as follows:
1. EUDRAGIT® E PO was added to acetone in a stainless steel container and mixed until a clear solution form.
2. Isopropyl alcohol was added to the solution from step #1 and mixed for ~5 minutes.
3. To the solution from step #3, polyethylene glycol was added followed by talc and mixed until a homogenous dispersion was obtained.
4. The FC 1 coated granules were further coated using a Wurster fluid bed coater with an inlet air temperature of 40°-50° C., and sufficient air volume for fluidization.
5. When the product temperature reached 30° C., the dispersion from step #4 was sprayed onto the FC 1 coated granules while maintaining the product temperature of 28°-30° C. and sufficient air volume for the fluidization, until the target coating weight gain (46.80 mg) was achieved.
6. The coated granules from step #6 were dried to FC 2 coated granules.

Example 10: Functional Coating of Seal Coated Hydrocodone Bitartrate Granules Seal coated hydrocodone bitartrate granules were coated with a first functional coat layer FC 1 comprising a mixture of rate controlling polymers, e.g., cellulose acetate (CA) and EUDRAGIT® E PO, in a ratio of CA:EUDRAGIT® E PO of 60:40, and a second functional coat layer FC 2 comprising EUDRAGIT® E PO as the sole rate controlling polymer.

TABLE 14

Formulation of Functional Coated Opioid Granules

| Components | Functional Coated Granules (mg/dose) |
|---|---|
| FC 1 | |
| Seal coated hydrocodone bitartrate granules | 120.00 |
| Cellulose acetate | 18.00 |
| EUDRAGIT® E PO | 12.00 |
| Dibutyl sebacate | 4.50 |
| Colloidal silicon dioxide | 1.50 |
| Solvent system for coating | |
| Acetone | NA |
| Purified water | NA |
| Total | 156.00 |
| FC 2 | |
| FC 1 coated granules | 156.00 |
| EUDRAGIT® E PO | 72.00 |
| Polyethylene glycol | 7.20 |
| Talc | 14.40 |
| Solvent System for Coating | |
| Acetone | NA |
| Isopropyl alcohol | NA |
| Total | 249.60 |

Coating Procedure:
1. EUDRAGIT® E PO was added to acetone in a stainless steel container and mixed until a clear solution formed.
2. To the solution from step #1, cellulose acetate was added and mixed until a clear solution formed.
3. Isopropyl alcohol was added to the solution from step #2 and mixed for ~5 minutes.
4. To the solution from step #3, dibutyl sebacate was added followed by colloidal silicon dioxide and continued mixing until a homogenous dispersion was obtained.
5. The seal coated granules were further coated using a Wurster fluid bed coater with an inlet air temperature of 40°-50° C. and sufficient air volume for fluidization.
6. When the product temperature reached 30° C., the dispersion from step #4 was sprayed onto the seal coated granules while maintaining the product temperature of 28°-30° C. and sufficient air volume for the fluidization, until the target coating weight gain (36 mg) was achieved.
7. The coated granules from step #6 were dried to FC 1 coated granules.

The FC 1 coated granules were further coated with a second functional coat layer (FC 2) as follows:
1. EUDRAGIT® E PO was added to acetone in a stainless steel container and mixed until a clear solution form.
2. The purified water was added to the solution from step #1 and mixed for ~5 minutes.
3. To the solution from step #3, polyethylene glycol was added followed by talc and mixed until a homogenous dispersion was obtained.

4. The FC 1 coated granules were further coated using a Wurster fluid bed coater with an inlet air temperature of 40°-50° C., and sufficient air volume for fluidization.
5. When the product temperature reached 30° C., the dispersion from step #4 was sprayed onto the FC1 coated granules while maintaining the product temperature of 28°-30° C. and sufficient air volume for the fluidization, until the target coating weight gain (93.60 mg) was achieved.
6. The coated granules from step #6 were dried to FC 2 coated granules.

Example 11: Over Coating of Functional Coated Oxycodone Hydrochloride Granules

Functional coated oxycodone hydrochloride granules were coated with an over coat.

TABLE 15

Formulation of Over Coated Opioid Granules

| Components | Over Coated Granule 1 (mg/dose) | Over Coated Granule 2 mg/dose | Over Coated Granule 3 mg/dose | Over Coated Granule 4 mg/dose | Over Coated Granule (#5- 8) mg/dose |
|---|---|---|---|---|---|
| FC 2 coated granules | 249.6 | 249.6 | 249.6 | 249.6 | 249.6 |
| Hypromellose, USP (Methocel E5 Premium LV) | 28.00 | 28.00 | 28.00 | 28.00 | 28.80 |
| Triethyl Citrate, NF | 2.88 | 2.88 | 2.88 | 2.88 | 2.88 |
| Talc, USP (2755) | 5.76 | 5.76 | 5.76 | 5.76 | 5.76 |
| Solvent System for Coating | | | | | |
| Dehydrated alcohol* | NA | NA | NA | NA | NA |
| Purified water* | NA | NA | NA | NA | NA |
| Total | 286.24 | 286.24 | 286.24 | 286.24 | 287.04 |

*Removed during process

TABLE 16

Formulation of Over Coated Opioid Granules

| Components | Over Coated Granules mg/dose |
|---|---|
| Functional coated Hydromorphone Hydrochloride granules | 124.80 |
| Methocel E5 Premium LV | 14.40 |
| Triethyl citrate | 1.44 |
| Colloidal silicon dioxide | 2.88 |
| Solvent System for Coating | |
| Purified water | NA |
| Dehydrated alcohol | NA |
| Total | 143.52 |

Coating Procedure:
1. Hypromellose was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of talc and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (36.44 mg) was achieved.
6. The coated granules from step #5 were dried.

Example 12: Over Coating of Functional Coated Hydromorphone Hydrochloride Granules Functional coated hydromorphone hydrochloride granules were coated with an over coat.

Coating Procedure:
1. Methocel was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (18.72 mg) was achieved.
6. The coated granules from step #5 were dried.

Example 13: Over Coating of Functional Coated Hydrocodone Bitartrate Granules

Functional coated Hydrocodone bitartrate granules were coated with an over coat.

TABLE 17

Formulation of Over Coated Opioid Granules

| Components | Over Coated Granules (mg/dose) |
|---|---|
| Functional coated hydrocodone bitartrate granules | 249.60 |
| Methocel E5 Premium LV | 28.80 |
| Triethyl citrate | 2.88 |
| Colloidal silicon dioxide | 5.76 |
| Solvent System for Coating | |
| Purified water | NA |
| Dehydrated alcohol | NA |
| Total | 287.04 |

Coating Procedure:
1. Methocel was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (37.44 mg) was achieved.
6. The coated granules from step #5 were dried.

Example 14: Opioid Pellets

Opioid Pellets with microcrystalline cellulose (MCC) core (cellets) were prepared for use in a 30 mg oxycodone hydrochloride dosage form.

TABLE 18

Formulation of Opioid Pellets

| Components | Opioid Pellets 1 (mg/dose) |
|---|---|
| Microcrystalline cellulose pellets (Cellets) | 300.00 |
| Oxycodone hydrochloride | 30.00 |
| Methocel E5 premium LV | 20.00 |
| Talc | 3.00 |
| Solvent system for coating | |
| Purified water | NA |
| Dehydrated alcohol | NA |
| Total | 353.00 |

Manufacturing Procedure:
1. Oxycodone hydrochloride was added to the dehydrated alcohol in a stainless steel container and mixed until it dispersed uniformly.
2. After the oxycodone was uniformly dispersed, METHOCEL™ was gradually added with continuous mixing to form a uniform dispersion.
3. The purified water was added to the dispersion from step #2 and mixed until a clear solution was obtained.
4. To the solution from step #3, talc was added and mixed for at least 30 minutes or more, until it was dispersed.
5. The microcrystalline cellulose pellets were coated using a Wurster fluid bed coater with an inlet air temperature of 40°-50° C. and sufficient air volume for fluidization.
6. When the product temperature reached 30° C., the dispersion from step #4 was sprayed onto the pellets while maintaining the temperature of 28°-30° C. and sufficient air volume for the fluidization, until the target coating weight gain (53 mg) was achieved.
7. The coated pellets from step #6 were dried.

Example 15: Seal Coating of Pellets

Opioid Pellets from Example 18 were coated with a seal coat.

TABLE 19

Formulation of Seal Coated Pellets

| Components | Seal Coated Opioid Pellets 1 (mg/dose) |
|---|---|
| Opioid Pellets 1 | 353.00 |
| Methocel E5 premium LV | 15.70 |
| Dibutyl sebacate | 0.80 |
| Talc | 5.50 |
| Solvent system for coating | |
| Purified water | NA |
| Dehydrated alcohol | NA |
| Total | 375.00 |

Coating Procedure:
1. Methocel was added to dehydrated alcohol in a stainless steel container and mixed into a uniform dispersion.
2. To the dispersion from step #1, the purified water was added and mixed until a clear solution formed.
3. To the solution from step #2, dibutyl sebacate was added followed by the addition of talc and continued mixing until a homogenous dispersion formed.
4. The pellets were coated using a Wurster fluid bed coater with an inlet air temperature of 40°-50° C., and sufficient air volume for fluidization.
5. When the product temperature reached 30° C., the dispersion from step #3 was sprayed onto the pellets while maintaining the product temperature of 28°-30° C. and sufficient air volume for fluidization, until the target coating weight gain (22 mg) was achieved.
6. The coated pellets from step #5 were dried.

Example 16: Functional Coating of Pellets (60:40)

Seal coated Opioid Pellets from Example 19 were coated with a functional coat at a ratio of OPADRY® CA to EUIDRAGIT® E PO of 60:40.

TABLE 20

Formulation of Functional Coated Pellets

| Components | Functional Coated Opioid Pellets 1 (mg/dose) |
|---|---|
| Seal coated pellets 1 | 375.00 |
| OPADRY® cellulose acetate clear | 15.54 |
| EUDRAGIT® E PO | 10.36 |
| Talc | 9.10 |
| Dibutyl sebacate | 2.60 |
| Solvent system for coating | |
| Acetone | NA |
| Purified water | NA |
| Total | 412.60 |

Coating Procedure:
1. EUDRAGIT® E PO was added to acetone in a stainless steel container and mixed until a clear solution formed.
2. To the solution from step #1, OPADRY® cellulose acetate was added and mixed until a clear solution formed.
3. To the solution from step #2, the purified water was added and mixed for ~5 minutes.
4. To the solution from step #3, dibutyl sebacate was added followed by talc and continued mixing until a homogenous dispersion formed.
5. The seal coated pellets were further coated using a Wurster fluid bed coater with an inlet air temperature of 40°-50° C. and sufficient air volume for fluidization.
6. When the product temperature reached 30° C., the dispersion from step #4 was sprayed onto the seal coated granules and pellets while maintaining the product temperature of 28°-30° C. and sufficient air volume for the fluidization, until the target coating weight gain (37.6 mg) was achieved.
7. The coated pellets from step #6 were dried.

Example 17: Functional Coating of Pellets (80:20)

Seal coated Opioid Granules and Pellets are coated with a functional coating at a ratio of OPADRY® cellulose acetate or Kollidon SR to EUIDRAGIT® E PO of 80:20.

TABLE 21

Formulation of Functional Coated Pellets

| Components | Functional Coated Opioid Pellets 2 (mg/dose) | Functional Coated Opioid Pellets 3 (mg/dose) |
|---|---|---|
| Seal coated pellets 1 | 375.00 | 375.00 |
| Kollidon | 20.70 | NA |
| OPADRY® cellulose acetate clear | NA | 20.70 |
| EUDRAGIT® E PO | 5.20 | 5.20 |
| Talc | 9.10 | 9.10 |
| Dibutyl sebacate | 2.60 | 2.60 |
| Solvent system for coating | | |
| Acetone | NA | NA |
| Purified water | NA | NA |
| Total | 412.60 | 412.60 |

Coating Procedure:
1. EUDRAGIT® E PO was added to acetone in a stainless steel container and mixed until a clear solution formed.
2. To the solution from step #1 OPADRY® Cellulose Acetate/Kollidon was added and mixed until a clear solution formed.
3. The purified water was added to the solution from step #2 and mixed for ~5 minutes.
4. To the solution from step #3 dibutyl sebacate was added followed by talc and continued mixing until a homogenous dispersion formed.
5. The seal coated granules and pellets are further coated using a Wurster fluid bed coater with an inlet air temperature of 40°-50° C. and sufficient air volume for fluidization.
6. When the product temperature reached 30° C., the dispersion from step #4 was sprayed onto the granules and pellets while maintaining the product temperature of 28°-30° C. and sufficient air volume for the fluidization until the target coating weight gain (37.60 mg) was achieved.
7. The coated pellets from step #6 were dried.

Example 18: Triggering Granules

Triggering Granules were prepared as described below.

TABLE 22

Formulation of Triggering Granules

| Component | Triggering Granule 1 (mg/dose) | Triggering Granule 2 (mg/dose) | Triggering Granule 3 (mg/dose) |
|---|---|---|---|
| Magnesium hydroxide | 135.00 | 100.00 | 250.00 |
| Mannitol | 22.50 | 16.66 | 41.67 |
| Crospovidone | 6.71 | 4.99 | 12.47 |
| Total | 164.21 | 121.65 | 304.14 |

Manufacturing Procedure:
1. Magnesium hydroxide was added to mannitol, and crospovidone in a high shear granulator and mixed using an impeller and chopper to achieve a uniform blend.
2. The blend from step #1 was granulated by wet granulation using purified water.
3. The granules from step #2 were dried at 40° C. using a forced air oven until the LOD was less than 1%.

Example 19: Naloxone Hydrochloride Granules

Naloxone Hydrochloride Particulates (e.g., Naloxone Granules) were prepared as described below:

TABLE 23

Formulation of Naloxone Hydrochloride Granules

| | Naloxone Granule 1 | | Naloxone Granule 2 | |
|---|---|---|---|---|
| Composition | (% w/w) | mg/dose | (% w/w) | mg/dose |
| Naloxone Hydrochloride | 8.00 | 4.00 | 25.00 | 12.50 |
| Hydroxypropyl cellulose | 6.00 | 3.00 | 6.00 | 3.00 |
| Microcrystalline cellulose | 86.00 | 43.00 | 69.00 | 34.50 |
| Total | 100.0 | 50.00 | 100.0 | 50.00 |

Manufacturing Procedure:
1. Hydroxypropyl methyl cellulose and microcrystalline cellulose are added to naloxone hydrochloride in a high sheer granulator to achieve uniform powder mix using impeller and chopper at medium speeds.
2. The blend from step #1 is granulated using hot-melt extrusion, melt granulation, roller compaction, high shear or low shear mixing.
3. If required, granules from step #2 are subjected to appropriate delumping or size reduction process using co-mill, fitz mill, cryomilling, micropulverizer, or micronization.
4. The resulting granules from step #2 or #3 (if present) are spheronized using rotor.
5. The spheronized granules from step #4 are cured.

Example 20: Seal Coating of Naloxone Hydrochloride Granules

Naloxone hydrochloride granules are coated with a seal coat.

TABLE 24

| Formulation of Seal Coated Naloxone Hydrochloride Granules | | |
|---|---|---|
| Composition | (% w/w) | mg/dose |
| Naloxone hydrochloride (# 1 or 2) | 83.33 | 50.00 |
| Methocel E5 Premium LV | 14.82 | 8.89 |
| Triethyl citrate | 1.48 | 0.89 |
| Cab-o-sil | 0.37 | 0.22 |
| Solvent system for coating | | |
| Purified water* | 20.00 | NA |
| Dehydrated Alcohol* | 80.00 | NA |
| Total | 100.00 | 60.00 |

*Removed during process

Coating Procedure:
1. Methocel is added to dehydrated alcohol in a stainless steel container and mixed to form a uniform dispersion.
2. To the dispersion from step #1, the purified water is added and mixed until a clear solution is formed.
3. To the solution from step #2, triethyl citrate is added followed by the addition of cab-o-sil and mixed to form a homogenous dispersion.
4. The granules are coated using a Wurster fluid bed coater with an inlet air temperature of 40°-50° C., and sufficient air volume for fluidization.
5. When the product temperature reaches 30° C., the dispersion from step #3 is sprayed onto the granules while maintaining the product temperature of 28°-30° C. and sufficient air volume for the fluidization, until the target coating weight gain (20 mg) is achieved.
6. The coated granules from step #5 are dried.

Example 21: Enteric Coated Naloxone Hydrochloride Granules

Seal coated naloxone hydrochloride granules are coated with a functional coat (FC1)

TABLE 25

| Formulation of Enteric Coated Naloxone Hydrochloride Granules (FC1) | | |
|---|---|---|
| Composition | (% w/w) | mg/dose |
| Seal coated naloxone hydrochloride granules (#1 or 2)(FC1) | 76.92 | 60.00 |
| Eudragit ® L 100 | 19.15 | 14.94 |
| Polyethylene glycol | 0.10 | 0.08 |
| Talc | 3.82 | 2.98 |
| Solvent system for coating | | |
| Acetone* | 40.00 | NA |
| Isopropyl alcohol* | 60.00 | NA |
| Total | 100.00 | 78.00 |

*Removed during process

1. EUDRAGIT L100 is added to a mixture of acetone and isopropyl alcohol in a stainless steel container and mixed until a clear solution is obtained.
2. To the solution from step #1, polyethylene glycol is added followed by the addition of talc and mixed until a homogeneous dispersion is obtained.
3. The seal coated granules are further coated using a Wurster fluid bed coater with an inlet air temperature of 40°-50° C. and sufficient air volume for fluidization.
4. When the product temperature reaches 30° C., the dispersion from step #3 is sprayed onto the seal coated granules while maintaining the product temperature of 28°-30° C. and sufficient air volume for the fluidization, until the target coating weight gain is achieved.
5. The seal coated granules from step #4 were dried.

Example 22: Over Coated Naloxone Hydrochloride Granules

Enteric coated naloxone hydrochloride granules are coated with an over coat

TABLE 26

| Formulation of Over Coated Naloxone Hydrochloride Granule | | |
|---|---|---|
| | Over Coated Granules | |
| Composition | (% w/w) | mg/dose |
| Enteric coated naloxone hydrochloride granule (# 1 or 2) (FC1) | 86.96 | 78.00 |
| Methocel E5 Premium LV | 10.03 | 9.00 |
| Triethyl citrate | 1.00 | 0.90 |
| Talc | 2.01 | 1.80 |
| Solvent system for coating | | |
| Purified water* | 20.00 | NA |
| Dehydrated alcohol* | 80.00 | NA |
| Total | 100.00 | 89.70 |

*Removed during process

Coating Procedure:
1. Methocel E5 is added to dehydrated alcohol in a stainless steel container and mixed until it disperses uniformly.
2. To the dispersion from step #1 the purified water is added and mixed until a clear solution forms.
3. To the solution from step #2 triethyl citrate is added followed by the addition of talc and continued mixing until a homogenous dispersion forms.
4. The granules are coated using a Wurster fluid bed coater with an inlet air temperature of 40°-50° C. and sufficient air volume for fluidization.

5. When the product temperature reaches 30° C., the dispersion from step #3 is sprayed onto the granules while maintaining the product temperature of 28°-30° C. and sufficient air volume for the fluidization until the target coating weight gain is reached.
6. The coated granules from step #5 are dried.

Example 23: Viscosity Enhancing Granules

Viscosity Enhancing Granules were prepared as described below:

TABLE 27

Formulation of Viscosity Enhancing Granules

| Component | Viscosity Enhancing Granule 1 (mg/dose) | Viscosity Enhancing Granule 2 (mg/dose) | Viscosity Enhancing Granule 3 (mg/dose) |
|---|---|---|---|
| Crospovidone, NF (Polyplasdone XL) | 17.50 | NA | 21.00 |
| POLYOX ® WSR coagulant | 31.53 | 57.84 | 37.83 |
| Hypromellose, (Benecel K 200M Pharm) | 5.88 | 7.06 | 7.06 |
| Kollidon SR | 2.94 | 3.53 | 3.53 |
| Vitamin E (dl-α-tocopherol) | 0.13 | 0.15 | 0.15 |
| Triethyl Citrate, NF | 2.03 | 3.42 | 2.43 |
| Docusate sodium, NF (85%) with sodium benzoate, NF (15%) | 1.25 | 1.50 | 1.50 |
| Colloidal silicon dioxide, NF (Cab-O-Sil M-5P) | 1.25 | NA | NA |
| Aerosil 200 | NA | 1.50 | 1.50 |
| Total | 62.51 | 75.00 | 75.00 |
| Seal Coat | | | |
| Hypromellose (Methocel E5 Premium LV) | 11.12 | NA | NA |
| Triethyl citrate, NF | 1.12 | NA | NA |
| Colloidal silicon dioxide, NF (Cab-O-Sil M-5P) | 0.25 | NA | NA |
| Total | 75.00 | 75.00 | 75.00 |

Manufacturing Procedure:
1. POLYOX® WSR coagulant was added to hypromellose, Kollidon® SR, docusate sodium, and crospovidone/starch 1500 in a high shear granulator and mixed to achieve a uniform powder mix using impeller and chopper.
2. A solution of dl-α-tocopherol solution and triethyl citrate was sprayed onto the powder mix from step #1 to achieve a uniform blend.
3. Colloidal silicon dioxide/Aerosil 200 was added to the blend from step #2 and mixed to achieve a uniform blend using an impeller and chopper.
4. The blend from step #3 was granulated by hot melt extrusion.
5. The granules from step #4 were processed using cryomilling to a mean particle size of 500 μm.

Seal Coating Procedure:
1. Hypromellose was added to dehydrated alcohol in a stainless steel container and mixed to form a uniform dispersion.
2. To the dispersion from step #1, the purified water was added and mixed until a clear solution formed.
3. To the solution from step #2, triethyl citrate was added followed by the addition of colloidal silicon dioxide and mixed to form a homogenous dispersion.
4. The granules were coated using a Wurster fluid bed coater with an inlet air temperature of 40°-50° C., and sufficient air volume for fluidization.
5. When the product temperature reached 30° C., the dispersion from step #3 was sprayed onto the granules while maintaining the product temperature of 28°-30° C. and sufficient air volume for the fluidization, until the target coating weight gain (12.49 mg) was achieved.
6. The coated granules from step #5 were dried.

Example 24: Tablet Composition

Oxycodone hydrochloride/naloxone combination tablets (5 or 15 mg) were manufactured as described below.

TABLE 28

Formulation Composition of Oxycodone Hydrochloride/Naloxone Combination

| Tablet Composition | Tablet 1 mg/unit | Tablet 2 mg/unit |
|---|---|---|
| Over coated Oxycodone hydrochloride granules (#5-8) | 312.00* | 312.00* |
| Viscosity Enhancing Granules | 75.00 | 75.00 |
| Triggering Granules | 304.14 | 304.14 |
| Naloxone Hydrochloride | 4.00 | 12.50 |
| Microcrystalline cellulose | 244.86 | 236.36 |
| Mannitol | 30.00 | 30.00 |
| Hydroxypropyl cellulose | 7.50 | 7.50 |
| Croscarmellose Sodium | 18.75 | 18.75 |
| Magnesium Stearate | 3.75 | 3.75 |
| Tablet weight | 1000.00 | 1000.00 |

*Equivalent weight of over coated active granules for 5 mg or 15 mg

Manufacturing Procedure:
1. A uniform blend of over coated opioid granules, viscosity enhancing granules, triggering granules, naloxone hydrochloride, microcrystalline cellulose, mannitol, hydroxypropyl cellulose, and croscarmellose sodium is made using a V-blender.
2. To the blend from step #1, magnesium stearate is added and blended for 3 minutes using a V-blender.
3. The blend from step #2 is compressed into tablets using a tablet press.

TABLE 29

Formulation Composition of Oxycodone Hydrochloride/Naloxone Combination

| Tablet Composition | Tablet 3 mg/unit | Tablet 4 mg/unit | Tablet 5 mg/unit | Tablet 6 mg/unit |
|---|---|---|---|---|
| Oxycodone Hydrochloride | 5.00 | 5.00 | 15.00 | 15.00 |
| Viscosity Enhancing Granules | 75.00 | 75.00 | 75.00 | 75.00 |
| Triggering granules | 304.14 | 304.14 | 304.14 | 304.14 |
| Naloxone Hydrochloride | 4.00 | 12.50 | 4.00 | 12.50 |
| Microcrystalline cellulose | 152.61 | 152.61 | 142.61 | 142.61 |
| Mannitol | 30.00 | 30.00 | 30.00 | 30.00 |
| Hydroxypropyl cellulose | 7.50 | 7.50 | 7.50 | 7.50 |
| Croscarmellose Sodium | 18.75 | 18.75 | 18.75 | 18.75 |
| Magnesium Stearate | 3.00 | 3.00 | 3.00 | 3.00 |
| Tablet weight | 600.00 | 600.00 | 600.00 | 600.00 |

Manufacturing Procedure:
1. A uniform blend of oxycodone hydrochloride, viscosity enhancing granules, triggering granules, naloxone hydrochloride, microcrystalline cellulose, mannitol, hydroxypropyl cellulose, and croscarmellose sodium is made using a V-blender.
2. To the blend from step #1, magnesium stearate is added and blended for 3 minutes using a V-blender.
3. The blend from step #2 is compressed into tablets using a tablet press.

TABLE 30

Formulation Composition of Oxycodone Hydrochloride/Naloxone Combination

| Tablet Composition | Tablet 7 mg/unit |
|---|---|
| Over coated Oxycodone hydrochloride granules (#5, 6, 7, or 8) | 312.00* |
| Viscosity Enhancing Granules | 75.00 |
| Triggering Granules | 304.14 |
| Over coated Naloxone Hydrochloride Granules (#1 or 2 | 89.70** |
| Microcrystalline cellulose | 159.16 |
| Mannitol | 30.00 |
| Hydroxypropyl cellulose | 7.50 |
| Croscarmellose Sodium | 18.75 |
| Magnesium Stearate | 3.75 |
| Tablet weight | 1000.00 |

*Equivalent weight of over coated active granules for 5 mg or 15 mg
**Equivalent weight of naloxone hydrochloride over coated granules for 4 mg or 12.50 mg Manufacturing Procedure:
1. A uniform blend of over coated active granules, viscosity enhancing granules, triggering granules, naloxone hydrochloride over coated granules, microcrystalline cellulose, mannitol, hydroxypropyl cellulose and croscarmellose sodium is made using a V-blender.
2. To the blend from step #1, magnesium stearate is added and blended for 3 minutes using a V-blender.
3. The blend from step #2 is compressed into tablets using a tablet press.

TABLE 31

Formulation Composition of Oxycodone Hydrochloride/Naloxone Combination

| Tablet Composition | Tablet 8 mg/unit | Tablet 9 mg/unit |
|---|---|---|
| Oxycodone Hydrochloride | 5.00 | 15.00 |
| Viscosity Enhancing Granules | 75.00 | 75.00 |
| Triggering Granules | 304.14 | 304.14 |
| Over coated Naloxone Hydrochloride Granules(#1 or 2) | 89.70** | 89.70** |
| Microcrystalline cellulose | 166.16 | 156.16 |
| Mannitol | 30.00 | 30.00 |
| Hydroxypropyl cellulose | 7.50 | 7.50 |
| Croscarmellose Sodium | 18.75 | 18.75 |
| Magnesium Stearate | 3.75 | 3.75 |
| Tablet weight | 700.00 | 700.00 |

**Equivalent weight of naloxone hydrochloride over coated granules for 4 mg or 12.50 mg Manufacturing Procedure:
1. A uniform blend of oxycodone hydrochloride, viscosity enhancing granules, triggering granules, naloxone hydrochloride over coated granules, microcrystalline cellulose, mannitol, hydroxypropyl cellulose and croscarmellose sodium is made using a V-blender.
2. To the blend from step #1, magnesium stearate is added and blended for 3 minutes using a V-blender.
3. The blend from step #2 is compressed into tablets using a tablet press.

Example 25: In Vitro Overdose Protection (ODP) Studies with 60:40 Opioid Pellets In order to examine the ability of the dosage form to prevent the release of its active when taken in doses above therapeutically effective amounts (e.g., three or more dosage units), taken in a manner inconsistent with the manufacturer's instructions, in a manner not prescribed, or overdosed, an in vitro dissolution test was conducted using a USP Apparatus II at pH 1.6. A pH of 1.6 was chosen to simulate the acidic environment of the stomach, and a single-unit study was compared with a five-unit study. Each unit represents a 30 mg oxycodone hydrochloride dosage form containing functional coated Opioid Pellets and Triggering Granules. In this Example, a functional coating with a ratio of OPADRY® cellulose acetate to EUIDRAGIT® E PO of 60:40 was used.

Experimental Procedure:
1. For each unit, 412.60 mg of functional coated Opioid Pellets 1 were combined with 350.00 mg of Triggering Granules 2 and placed in a capsule.
2. The capsule from step #1 was added to 250 mL of dissolution medium adjusted to a pH of 1.6.
3. Samples were withdrawn at 5, 10, 15, 30, 60, and 120 minutes for the single unit study and at 5, 10, 15, 30, 60, 120, and 240 minutes for the five unit study.
4. The samples obtained from step #3 were analyzed for the percent release of oxycodone by HPLC.

Example 26: In Vitro Overdose Protection (ODP) Studies with 80:20 Opioid Pellets In order to examine the ability of the dosage form to prevent the release of its active when taken in doses above therapeutically effective amounts (e.g., three or more dosage units), taken in a manner inconsistent with the manufacturer's instructions, in a manner not prescribed, or overdosed, an in vitro dissolution test was conducted using a USP Apparatus II at pH 1.6. A pH of 1.6 was chosen to simulate the acidic environment of the stomach, and each unit represents a 30 mg oxycodone hydrochloride dosage form containing functional coated Opioid Pellets and Triggering Granules. In this Example, a functional coating with a ratio of OPADRY® cellulose acetate to EUDRAGIT® E PO of 80:20 was used. The data suggest that a ratio of OPADRY® cellulose acetate to EUDRAGIT® E PO of 80:20 in the functional coat provided superior ODP properties to a dosage form containing an opioid, e.g., oxycodone hydrochloride.

Experimental Procedure:
1. For each unit, 412.60 mg of Functional Coated Opioid Pellets 2 was combined with 350.00 mg of Triggering Granules 2 and placed in a capsule.
2. The combination from step #1 was added to 250 mL of dissolution medium adjusted to a pH of 1.6.
3. Samples were withdrawn at 5, 10, 15, 30, 60, and 120 minutes for the single unit, two unit, three unit, and five unit studies.
4. The samples obtained from step #3 were analyzed for the percent release of oxycodone by HPLC.

Example 27: In Vitro Overdose Protection (ODP) Studies with Opioid Formulation Containing 15 mg of Oxycodone Hydrochloride In order to examine the ability of the dosage form to prevent the release of its active when taken in doses above therapeutically effective amounts (e.g., three or more dosage units), taken in a manner inconsistent with the manufacturer's instructions, in a manner not prescribed, or overdosed, an in vitro dissolution test was conducted using a USP Apparatus II at pH 1.6 for 30 minutes followed by pH 6.8 for 120 minutes. In order to mimic physiological conditions, the total volume of the dissolution medium was kept at 250 ml at pH 1.6 acid medium, and 300 ml at pH 6.8.

1. Oxycodone hydrochloride tablet (Tablets 1, 3, or 5) was added to a 250 ml acid-adjusted dissolution medium at pH 1.6, and the dissolution of the tablet was measured for 30 minutes.
2. 50 mL of 60 mM phosphate buffer was added to the solution from step #1, and the dissolution of the tablet was measured for an additional 120 minutes.
3. Samples were withdrawn from the solutions of steps #1 and #2 at intervals.
4. The samples obtained from step #3 were analyzed, using HPLC, for the percent release of oxycodone.
5. pH of the dissolution medium from step #1 (experiments with the oxycodone hydrochloride tablets of the presently disclosed subject matter) was measured at 2 minutes, 5 minutes, and 10 minutes after introduction of the tablet(s).
6. Steps #1-5 were repeated for addition of 3 and 6 dosage units (3 and 6 tablets).

The results showed that a single tablet had no appreciable effect on variation of pH with time (at 2, 5, and 10 minutes); however, with multiple tablets (3 and 6 tablets), the pH was greater than 5 within 2 minutes. The rapid rise in pH with multiple tablets can be attributed to the amount of pH modifier present in the pH triggering granules, and the rapid disintegration of the tablet. As a result of the rise in pH above 5 within 2 minutes, the pH-dependent polymer EUIDRAGIT® E PO, which acts as a pore former in the functional coating, becomes insoluble, thus changing the release mechanism from pore-mediated transport to true diffusion.

Example 28: In Vitro Abuse Deterrent Studies (Resistance to Grindability)

In order to examine the abuse resistance (e.g., ability to withstand grinding) of Opioid Granules, an in vitro physical manipulation test was conducted for various opioids, e.g., oxycodone, hydromorphone, and hydrocodone. In general, the API distribution follows PSD across sieve fractions as API stayed "locked-in" with the granules. The data demonstrated that even after grinding, the weight % of fine particles (i.e., particle size of below 125 µm; "fines fraction") remains very low, thereby inhibiting or preventing the abuser from snorting the opioid, even after tampering with the dosage form by grinding.

The results corroborate that the opioid granules have crush resistant properties and the majority of granules produced after grinding are in the size range of 250-500 µm. Simply from the size perspective, these granules are harder to snort compared to fine powder with a particle size of less than 250 µm. Furthermore, the majority of API resides with the larger granules, thereby reducing the effective amount of drug that can be snorted. If an abuser is still able to snort the particles, the dissolution rate of the API will be much slower due to the pH-sensitive coating and the viscosity enhancing polymer, thus drastically lowering the effective amount of drug delivered to the abuser (and required to achieve euphoria).

Grinding Procedure for opioid granules:
1. Four grams of opioid (e.g., oxycodone hydrochloride, hydromorphone hydrochloride, and hydrocodone bitartrate granules) granules were crushed in a Mortar and Pestle for 5 minutes or ground in a Hamilton Beach Coffee Grinder (Model #80365) for 2 minutes.
2. The powder was analyzed by sieve analysis using the following mesh sizes: 10 (2000 µm), 18 (1000 µm), 35 (500 µm), 60 (250 µm), 120 (125 µm), 230 (63 µm), and 425 (32 µm).
3. API distribution across all sieve fractions was determined by analyzing the API content in each sieve fraction by HPLC method using external reference standard.

Example 29: Naloxone Lipid Formulations

TABLE 32

Composition of Naloxone Lipid Formulations

| Composition | Lipid Formulation 1 mg/dose | Lipid Formulation 2 mg/dose | Lipid Formulation 3 mg/dose |
|---|---|---|---|
| Naloxone | 2.50 | 2.50 | 2.50 |
| Capmul MCM | 35.59 | NA | NA |
| Labrasol | NA | 47.45 | NA |
| Capmul PG-8 | NA | NA | 35.59 |
| Kolliphor EL | 11.86 | NA | 11.86 |
| Vitamin E | 0.05 | 0.05 | 0.05 |
| Total | 50.00 | 50.00 | 50.00 |

Manufacturing Procedure:
1. The lipid vehicle is taken in a suitable container and Vitamin E is added.
2. The temperature of the lipid solution is maintained at 40° C. using a water bath/hot plate.
3. Naloxone is slowly added to the lipid solution and mixed until a clear solution is obtained.
4. Once formed, the clear solution is allowed to cool to room temperature.

Example 30: Naloxone Pellets Manufactured by Extrusion

TABLE 33

Composition of Naloxone Pellets

| Composition | Formulation 1 mg/dose | Formulation 2 mg/dose |
|---|---|---|
| Naloxone lipid formulations | 50.00 | 50.00 |
| Microcrystalline cellulose | 100.00 | 75.00 |
| Syloid XDP | NA | 25.00 |
| Total | 150.00 | 150.00 |

Manufacturing Procedure 1:
1. The naloxone lipid formulation from Example 29 is sprayed to adsorb onto microcrystalline cellulose or to a blend of microcrystalline cellulose and SYLOID® XDP taken in a collette (mixer/granulator) and mixed for 5 minutes.
2. To the blend from step #1, the required amount of water/suitable solvent is added until a mass suitable for extrusion is obtained.
3. The pellets (~1000 μm) produced by extrusion are subjected to spheronization and dried overnight at 40° C. in an oven.

Manufacturing Procedure 2:
1. The naloxone lipid formulation from Example 29 is sprayed to adsorb onto microcrystalline cellulose or to a blend of microcrystalline cellulose and SYLOID® XDP taken in a collette (mixer/granulator) and mixed for 5 minutes.
2. The pellets (~1000 μm) produced by hot-melt extrusion are subjected to spheronization and dried overnight at 40° C. in an oven.

Example 31: Naloxone Pellets Comprising Amorphous Solid Dispersion (ASD) of Naloxone

TABLE 34

Composition of Naloxone Amorphous Solid Dispersion Formulations

| Composition | ASD Formulation 1 (% w/w) | ASD Formulation 2 (% w/w) | ASD Formulation 3 (% w/w) |
|---|---|---|---|
| Naloxone | 20.00 | 20.00 | 20.00 |
| Kollidon VA 64 | 75.00 | NA | NA |
| Hypromellose acetate succinate (HPMCAS-LF) | NA | 75.00 | NA |
| Eudragit L 100-55 | NA | NA | 75.00 |
| Vitamin E-TPGS | 5.00 | 5.00 | 5.00 |
| Solvent | | | |
| Acetone | 100.00 | 100.00 | 90.00 |
| Water | NA | NA | 10.00 |
| Total | 200.00 | 200.00 | 200.00 |

Manufacturing Procedure:
1. Amorphous solid dispersion (ASD) formulations are made by dissolving naloxone, Kollidon VA 64/HPMCAS-LF/Eudragit L 100-55 and Vitamin E-TPGS in acetone or acetone:water mixture.
2. The ASD formulations from step #1 are coated onto cellets using a Wurster fluid bed coater with an inlet air temperature of 40°-50° C. and sufficient air volume for fluidization.
3. When the product temperature is reached to 30° C., ASD formulations from step #1 are sprayed onto cellets while maintaining the product temperature of 28°-30° C. and sufficient air volume for the fluidization.
4. Coated cellets from step #3 are dried.
5. The drug layered cellets are optionally further coated with at least one functional coat.

Example 32: Seal Coating of Naloxone Pellets/Cellets

Naloxone pellets/cellets from Examples 30 and 31 are coated with a seal coat.

TABLE 35

Composition of Seal Coating of Naloxone Pellets/Cellets

| Composition | (% w/w) | mg/dose |
|---|---|---|
| Naloxone pellets/cellets | 83.33 | 150.00 |
| METHOCEL® E5 Premium LV | 14.82 | 26.67 |
| Triethyl citrate | 1.48 | 2.66 |
| CAB-O-SIL® | 0.37 | 0.67 |
| Solvent system for coating | | |
| Purified water* | 20.00 | NA |
| Dehydrated alcohol* | 80.00 | NA |
| Total | 100.00 | 180.00 |

*Removed during process

Coating Procedure:
1. METHOCEL® E5 is added to a stainless steel container containing dehydrated alcohol and mixed until it disperses uniformly.
2. To the dispersion from step #1 purified water is added and mixed until a clear solution is formed.
3. Triethyl citrate followed by CAB-O-SIL® is added to the solution from step #3 and mixed until a homogeneous dispersion is formed.
4. Homogeneous dispersion from step #3 is coated onto pellets/cellets using a Wurster fluid bed coater with an inlet air temperature of 40°-50° C. and sufficient air volume for fluidization. When the product temperature reaches 30° C., the dispersion from step #3 is sprayed onto pellets/cellets while maintaining the product temperature of 28°-30° C. and sufficient air volume for the fluidization until the target coating weight gain is reached.
5. The coated pellets/cellets from step #4 are dried.

Example 33: Functional Coating/Enteric Coating of Naloxone Pellets/Cellets

Seal coated naloxone pellets/cellets are coated with a functional coat.

TABLE 36

Composition of Functional Coating of Naloxone Pellets/Cellets

| Composition | (% w/w) | mg/dose |
|---|---|---|
| Seal-coated naloxone pellets/cellets | 76.92 | 180.00 |
| EUDRAGIT® L100-55 | 19.98 | 46.75 |
| PEG 6000 | 0.10 | 0.24 |
| Talc | 3.00 | 7.01 |
| Solvent system for coating | | |
| Acetone* | 40.00 | NA |
| Isopropyl alcohol* | 60.00 | NA |
| Total | 100.00 | 234.00 |

*Removed during process

Coating Procedure:
1. EUDRAGIT® L100-55 is added to the solution of acetone and isopropyl alcohol in a stainless steel container and mixed until a clear solution formed.
2. To the solution from step #1 polyethylene glycol (33% PEG solution in purified water) is added followed by talc and continued mixing until a homogenous dispersion is formed.
3. The seal coated pellets/cellets are further coated using a Wurster fluid bed coater with an inlet air temperature of 40°-50° C. and sufficient air volume for fluidization. When the product temperature reaches 30° C., the dispersion from step #2 is sprayed onto the seal coated pellets/cellets while maintaining the product temperature of 28°-30° C. and sufficient air volume for the fluidization until the target coating weight gain is reached.

4. The coated pellets/cellets from step #3 are dried.

Example 34: Over Coating of Naloxone Pellets/Cellets

Functional coated naloxone pellets/cellets are coated with an over coat.

TABLE 37

Composition of Over Coating of Naloxone Pellets/Cellets

| Composition | (% w/w) | mg/dose |
|---|---|---|
| Functional coated naloxone pellets/cellets | 86.67 | 234.00 |
| Methocel E5 Premium LV | 10.66 | 28.80 |
| Triethyl citrate | 1.07 | 2.88 |
| Talc | 1.60 | 4.32 |
| Solvent system for coating | | |
| Purified water* | 20.00 | NA |
| Dehydrated alcohol* | 80.00 | NA |
| Total | 100.00 | 270.00 |

*Removed during process

Coating Procedure:
1. Methocel E5 is added to dehydrated alcohol in a stainless steel container and mixed until it disperses uniformly.
2. To the dispersion from step #1 the purified water is added and mixed until a clear solution forms.
3. To the solution from step #2 triethyl citrate is added followed by the addition of talc and continued mixing until a homogenous dispersion forms.
4. The pellets/cellets are coated using a Wurster fluid bed coater with an inlet air temperature of 40°-50° C. and sufficient air volume for fluidization. When the product temperature reaches 30° C., the dispersion from step #3 is sprayed onto the pellets/cellets while maintaining the product temperature of 28°-30° C. and sufficient air volume for the fluidization until the target coating weight gain is reached.
5. The coated pellets/cellets from step #4 are dried.

Example 35: Oxycodone Hydrochloride/Naloxone (5 mg/2.5 mg) IR Tablet Composition

TABLE 38

Formulation Composition of Oxycodone Hydrochloride/Naloxone (5 mg/2.5 mg) IR Tablets

| Composition | mg/dose | mg/dose |
|---|---|---|
| Over-coated oxycodone hydrochloride granules | 312.00 | 351.00 |
| Over-coated naloxone pellets/cellets | 270.00 | 270.00 |
| Mannitol | 30.00 | 30.00 |
| Microcrystalline cellulose | 356.75 | 317.75 |

TABLE 38-continued

Formulation Composition of Oxycodone Hydrochloride/Naloxone (5 mg/2.5 mg) IR Tablets

| Composition | mg/dose | mg/dose |
|---|---|---|
| Hydroxypropyl cellulose | 7.50 | 7.50 |
| Croscarmellose sodium | 18.75 | 18.75 |
| Magnesium stearate | 5.00 | 5.00 |
| Total | 1000.00 | 1000.00 |

Manufacturing Procedure:
1. A uniform blend of over coated oxycodone hydrochloride granules, over coated naloxone pellets/cellets, mannitol, microcrystalline cellulose, hydroxypropyl cellulose, and croscarmellose sodium is made using a V-blender.
2. To the blend from step #1, magnesium stearate is added and blended for three minutes using a V-blender.
3. The blend from step #2 is compressed into tablets using a tablet press.

Example 36: Oxycodone Hydrochloride/Naloxone (5 mg/2.5 mg) IR Capsule Dosage Form

TABLE 39

Formulation Composition of Oxycodone Hydrochloride/Naloxone (5 mg/2.5 mg) IR Capsules

| Composition | mg/dose | mg/dose |
|---|---|---|
| Over-coated oxycodone hydrochloride granules | 312.00 | 351.00 |
| Over-coated naloxone pellets/cellets | 270.00 | 270.00 |
| Total | 582.00 | 621.00 |

Manufacturing Procedure:
1. A uniform blend of over coated oxycodone hydrochloride granules, over coated naloxone pellets/cellets is made using a V-blender.
2. Based on the fill weight, the blend from Step #1 is filled into capsules.

Example 37: Oxycodone Hydrochloride/Naloxone (5 mg/2.5 mg) IR Capsule Dosage Form Over-coated oxycodone hydrochloride granules are compressed into a first tablet population. Over coated naloxone pellets/cellets are compressed into a second tablet population. The two tablet populations are filled into capsules.

TABLE 40

Formulation Composition of Oxycodone Hydrochloride/Naloxone (5 mg/2.5 mg) IR Capsules

| Opioid Tablet Components | mg/dose | mg/dose |
|---|---|---|
| Over-coated oxycodone hydrochloride granules | 312.00 | 351.00 |
| Microcrystalline cellulose | 100.00 | 201.00 |
| Hydroxypropyl cellulose | 2.50 | 3.50 |
| Croscarmellose sodium | 5.00 | 7.50 |
| Magnesium stearate | 2.50 | 3.00 |
| Naloxone Tablet Components | | |
| Over coated naloxone pellets/cellets | 270.00 | 270.00 |
| Microcrystalline cellulose | 98.00 | 150.00 |

TABLE 40-continued

Formulation Composition of Oxycodone Hydrochloride/Naloxone (5 mg/2.5 mg) IR Capsules

| Opioid Tablet Components | mg/dose | mg/dose |
|---|---|---|
| Hydroxypropyl cellulose | 2.50 | 3.50 |
| Croscarmellose sodium | 5.00 | 7.50 |
| Magnesium stearate | 2.50 | 3.00 |
| Total | 800.00 | 1000.00 |

Manufacturing Procedure:
1. A uniform blend of over coated oxycodone hydrochloride granules, microcrystalline cellulose, hydroxypropyl cellulose, and croscarmellose sodium is made using a V-blender.
2. To the blend from step #1, magnesium stearate is added and blended for 3 minutes using a V-blender and then compressed into tablets using a tablet press.
3. Similarly, a uniform blend of over coated naloxone pellets/cellets, microcrystalline cellulose, hydroxypropyl cellulose and croscarmellose sodium is made using a V-blender.
4. To the blend from step #3, magnesium stearate is added and the mixture is further blended for 3 minutes using a V-blender, and then compressed into tablets using a tablet press.
5. Tablets from step #2 and step #4 are filled into capsules.

The invention claimed is:

1. A multi-particulate, solid, oral, immediate release, opioid and naloxone combination dosage form with overdose protection properties comprising:
   Opioid Particulates comprising a therapeutically effective amount of oxycodone hydrochloride embedded in a polymer matrix, wherein the Opioid Particulates are coated with an acid labile coat;
   Triggering Particulates comprising an alkaline agent; and
   Naloxone Particulates comprising naloxone hydrochloride, wherein the Naloxone Particulates are enteric coated,
   wherein the ratio of oxycodone hydrochloride to naloxone hydrochloride is about 1:2.5,
   wherein the naloxone is present in an amount of between about 4 mg and about 12.5 mg,
   wherein, when three or more units of the dosage form are consumed together by a subject, the alkaline agent from the Triggering Particulates increases the gastric fluid pH to release naloxone hydrochloride from the enteric coated Naloxone Particulates and increase oral bioavailability of naloxone hydrochloride by saturating first-pass metabolism, thereby making available a pharmacologically effective amount of naloxone to block binding of oxycodone hydrochloride to central opioid receptors
   for about 20 minutes to about 90 minutes.

2. The dosage form of claim 1, wherein the pharmacologically effective amount of naloxone hydrochloride comprises a plasma concentration of from about 0.7 ng/ml to about 2 ng/ml.

3. The dosage form of claim 1, wherein the enteric coated Naloxone Particulates provide dose-dependent oral bioavailability of naloxone hydrochloride comprising an increase in oral bioavailability of naloxone hydrochloride per dosage unit, when three or more units of the dosage form are consumed together.

4. The dosage form of claim 1, wherein oxycodone hydrochloride is embedded in a polymer matrix comprising a cationic copolymer based on dimethylaminoethyl methacrylate, butyl methacrylate, and methyl methacrylate.

5. The dosage form of claim 1, wherein the enteric coated Naloxone Particulates comprise an enteric coating of at least one polymer selected from the group consisting of a copolymer of methacrylic acid and methyl methacrylate (1:1), a copolymer of methacrylic acid and methyl methacrylate (1:2), a copolymer of methacrylic acid and ethyl acrylate (1:1), hydroxypropyl methylcellulose acetate succinate, hydroxypropyl methylcellulose phthalate, cellulose acetate phthalate, crosslinked polyacrylic polymers, and polyvinyl acetate phthalate.

6. The dosage form of claim 1, wherein naloxone hydrochloride is not coreleased with oxycodone hydrochloride when one or two dosage units are consumed together.

\* \* \* \* \*